United States Patent
Williams

(10) Patent No.: US 9,877,361 B2
(45) Date of Patent: Jan. 23, 2018

(54) PHOTOTHERAPY SYSTEM AND PROCESS INCLUDING DYNAMIC LED DRIVER WITH PROGRAMMABLE WAVEFORM

(71) Applicant: Richard K. Williams, Cupertino, CA (US)

(72) Inventor: Richard K. Williams, Cupertino, CA (US)

(73) Assignee: Applied BioPhotonics Ltd, Hong Kong (CN)

( * ) Notice: Subject to any disclaimer, the term of this patent is extended or adjusted under 35 U.S.C. 154(b) by 838 days.

(21) Appl. No.: 14/073,371

(22) Filed: Nov. 6, 2013

(65) Prior Publication Data

US 2014/0128941 A1    May 8, 2014

Related U.S. Application Data

(60) Provisional application No. 61/723,950, filed on Nov. 8, 2012.

(51) Int. Cl.
    *A61N 5/06*      (2006.01)
    *A61B 18/18*     (2006.01)
    *H05B 33/08*     (2006.01)

(52) U.S. Cl.
    CPC ............... *H05B 33/08* (2013.01); *A61N 5/06* (2013.01); *H05B 33/0803* (2013.01);
    (Continued)

(58) Field of Classification Search
    CPC ........ A61N 5/06; A61N 5/0616; A61N 5/062; A61N 2005/0626; A61B 18/18; A61B 2018/00636; A61B 2018/00696; H05B 33/00; H05B 33/08; H05B 33/0803; H05B 33/0824; H05B 33/0835; H05B 33/0881
    (Continued)

(56) References Cited

U.S. PATENT DOCUMENTS 6,443,978 B1 * 9/2002 Zharov ............... A61N 5/0616
    606/13
6,663,659 B2 * 12/2003 McDaniel ........... A61B 18/203
    128/898

(Continued)

FOREIGN PATENT DOCUMENTS

CN      101959554 A      1/2011
WO      9507731 A1      3/1995
(Continued)

*Primary Examiner* — Ahmed Farah
(74) *Attorney, Agent, or Firm* — Patentability Associates; David E. Steuber

(57) ABSTRACT

A phototherapy or photobiomodulation process employing the application of electromagnetic radiation (EMR) to a living organism, typically a human being. The EMR is generated by one or more strings of LEDs and is programmed to emit one or more wavelengths, typically in the visible and infrared portions of the spectrum, the EMR in each wavelength being delivered in pulses having specified on-times, off-times, photoexcitation frequencies, duty factors, phase delays, and power amplitudes. A system for providing such EMR includes a microcontroller having a pattern library of algorithms, each of which defines a particular sequence of synthesized pulses, and an application pad, preferably flexible, containing the LED strings.

50 Claims, 53 Drawing Sheets

(52) U.S. Cl.
  CPC ..... *H05B 33/0827* (2013.01); *H05B 33/0866* (2013.01); *A61N 2005/0626* (2013.01); *A61N 2005/0651* (2013.01)

(58) Field of Classification Search
  USPC .................................... 607/88–92; 606/9–12
  See application file for complete search history.

(56) References Cited

U.S. PATENT DOCUMENTS

| | | | | |
|---|---|---|---|---|
| 8,334,662 | B2* | 12/2012 | Jin ..................... | H05B 33/0818 315/291 |
| 8,779,696 | B2* | 7/2014 | Williams ............ | H05B 33/083 315/169.1 |
| 9,351,364 | B2* | 5/2016 | Williams ............ | H05B 33/083 |
| 9,451,664 | B2* | 9/2016 | Jin ..................... | H05B 33/0818 |
| 2006/0229690 | A1* | 10/2006 | Shanks ................ | A61N 5/0616 607/89 |
| 2009/0177253 | A1 | 7/2009 | Darm et al. | |
| 2011/0125231 | A1 | 5/2011 | Ripper et al. | |
| 2013/0147375 | A1* | 6/2013 | Williams ........... | H05B 33/0827 315/192 |
| 2014/0276248 | A1* | 9/2014 | Hall .................... | A61N 1/0432 601/2 |
| 2014/0361698 | A1* | 12/2014 | Pereira .............. | H05B 33/0809 315/193 |

FOREIGN PATENT DOCUMENTS

| | | |
|---|---|---|
| WO | 2009089177 A1 | 7/2009 |
| WO | 2010078581 A1 | 7/2010 |

\* cited by examiner

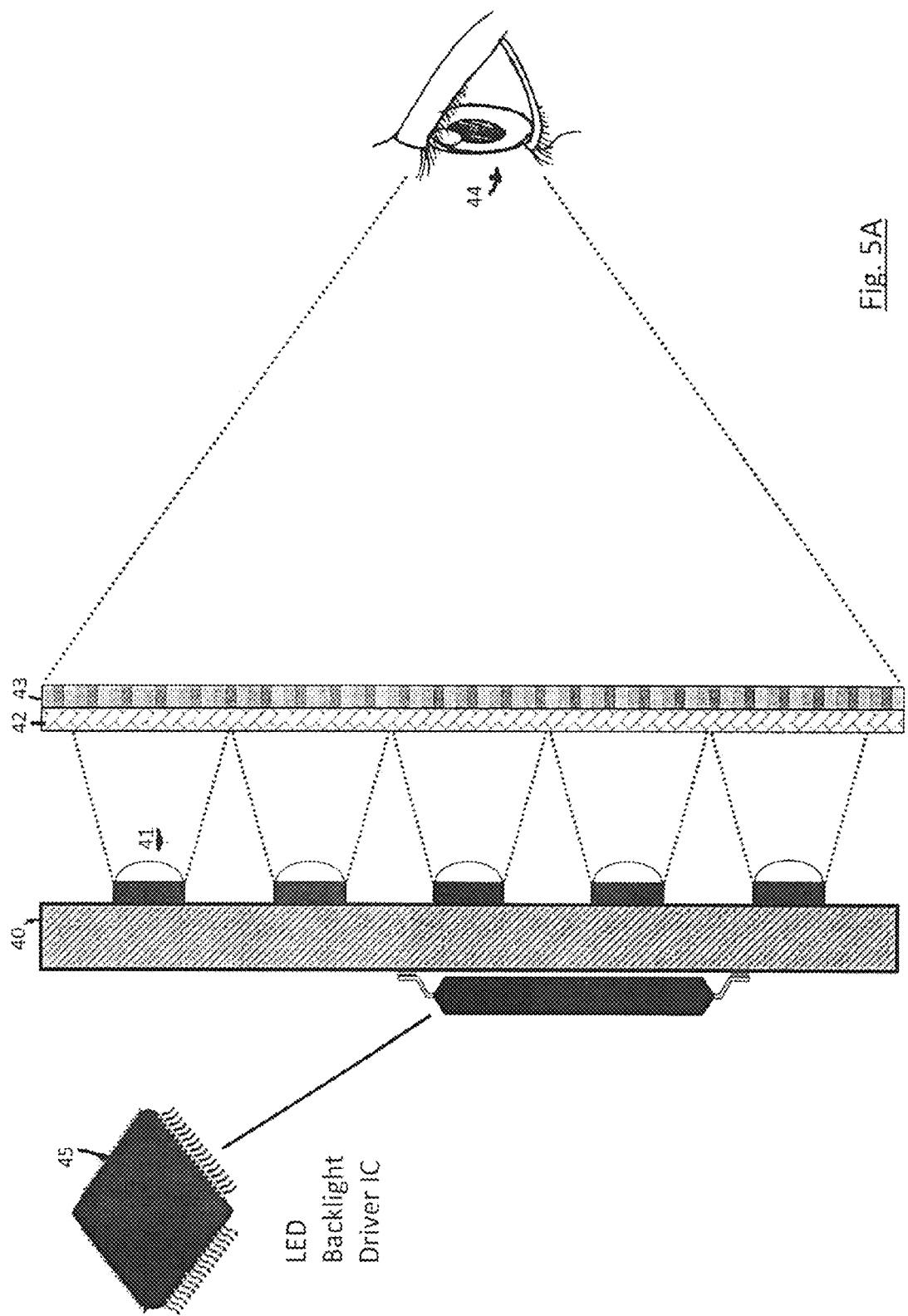

| Hierarchy | Example | Illustration | Systemic Photobiological Response |
|---|---|---|---|
| Organism | *Homo Sapiens* (human) | 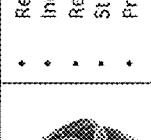 | • Reduction of injury & chronic pain (nervous system)<br>• Post concussion recovery of cognitive abilities (brain, nerves)<br>• Peripheral neuropathy recovery of tactile sensation (nerves)<br>• Improved immune response, suppress autoimmune dysfunction<br>• Decreased muscle spasms, tightness, improved motion (muscular)<br>• Sense of wellness, relaxation, reduced tension (psychosomatic) |
| Organ | Brain, Spinal Cord, Nerves (nervous system) | 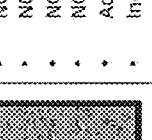 | • Reduced swelling & inflammation, arthritic attacks (immune)<br>• Increased circulation, dilation of blood vessels (circulatory)<br>• Repair nerve damage from concussion, diabetes, poisoning (nerves)<br>• Strengthens immune system countering chemo, radiation, AIDs<br>• Promotes tissue repair post burn, gunshots, cuts, suppress infection<br>• Increased lymphatic system activity, balances hormonal levels |
| Tissue | Neocortex (neural) | 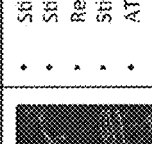 | • NO (nitric oxide) promotes new capillary formation, tissue regrowth<br>• NO stimulates collagen & fibroblastic growth in tissue repair<br>• NO stimulates blood flow and oxygen delivery to damaged tissue<br>• NO suppresses pain signals in nerves (opiates without side effects)<br>• Acetylcholine activates heart vasodilation, gastrointestinal peristalsis<br>• Increased phagocytosis (leucocytes scavenging dead/damaged cells) |
| Cell | Brain, Nerves (neuron) | 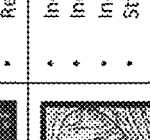 | • Stimulates tissue granulation, connective tissue projections (healing)<br>• Stimulates acetylcholine release in specific nerves, circulation<br>• Releases NO (nitric oxide) from hemoglobin promoting tissue repair<br>• Stimulates platelet & leucocyte production, immune response<br>• ATP stimulates cell nutrient & oxygen delivery, remove wastes faster<br>• Removes ATP inhibitors (e.g. in optic nerves), stimulates recovery |
| Organelle | Mitochondria (animal) | | • Increased in ATP (adenosine triphosphate), photosynthesis (animal)<br>• Increased cellular energy output, molecular vibrational activity<br>• Increased biochemical reaction rates, intercellular charge transport<br>• Stimulates DNA to RNA transcription, protein & enzyme synthesis<br>• Increases intracellular catalyst concentrations (CCO, $H_2O_2$, NO, etc.)<br>• Increases generation rate of DNA repair enzymes (DNA polymerase) |

Fig. 8D

PHOTOTHERAPY SYSTEM AND PROCESS INCLUDING DYNAMIC LED DRIVER WITH PROGRAMMABLE WAVEFORM

CROSS-REFERENCE TO RELATED APPLICATION

This application claims the priority of Provisional Application No. 61/723,950, filed Nov. 8, 2012, which is incorporated herein by reference in its entirety.

SCOPE OF INVENTION

This invention relates to biotechnology for medical applications, including photobiomodulation and phototherapy.

BACKGROUND OF INVENTION

Introduction

It is well known that electromagnetic radiation, a fundamental energy permeating the entire universe, affects living organisms in a wide variety of ways. Depending on the frequency or wavelength of the radiation and on its intensity or power level, electromagnetic radiation, also known as EMR, may be beneficial or hazardous to living creatures.

Although radio waves and low power microwaves used in cell phones are largely considered benign, deep UV (ultraviolet light) and x-rays are known to be carcinogenetic and potentially life threatening to living creatures even at moderate doses. Still other frequencies, such as visible light, are beneficial and necessary to organisms, helping power earth's biosphere by enabling photosynthesis in plants and bacteria at the base of our planetary food chain. EMR has also become an indispensible tool used in radio frequency and microwave communication, and in the infrared portion of the spectrum for imaging and night vision. Unwanted electromagnetic radiation is often referred to as EMI or electromagnetic interference.

In electronics, meeting government established standards for the emission of electromagnetic noise and avoiding unwanted interference with other electrical devices is referred to as EMC, or electromagnetic compatibility. Other government standards apply to the maximum accepted power level emitted by a device (e.g. the brightness of a laser pointer or an industrial laser, or the maximum power level of a microwave oven or a microwave communications tower), and especially for any apparatus involving ionizing radiation such as alpha particle and x-ray sources or nuclear material.

Physicists today regards EMR as a spectral continuum (collectively the electromagnetic spectrum) describing a single type of energy based on the electromagnetic force in nature, varying by its frequency (alternatively by its wave length or wave number) and by its brightness, flux density or intensity. The electromagnetic spectrum 1 shown in FIG. 1 described (from left to right) in bands of decreasing wavelength (and increasing frequency) includes AC power distribution at the longest wavelengths (not shown), followed by radio, microwave, infrared, visible light, ultraviolet, x-rays, gamma-rays, and beyond that, cosmic rays (not shown).

Of particular importance to humans, the visible spectrum of light (or visible band 3) ranges from 750 nm to 400 nm varying monotonically in color from red to orange, yellow, green, blue, and to purple (as seen in a rainbow). The combination of these colors produces white light especially important for color vision. Visible light is also important in plants and algae for powering photosynthesis. Chloroplasts, organelles within plant cells, use chlorophyll to capture sunlight and to convert it into energy using the process of photosynthesis. Since the chlorophyll absorbs red, blue, and violet light, it makes plants appear green in color.

Light wavelengths in the band adjacent to visible light longer than 750 nm and shorter than 1 mm are referred to as the infrared band 2, with those closest to visible light referred to as "near" infrared or NIR and longer wavelengths as long infrared and far infrared. Long infrared light in the 8- to 15-µm range is used for infrared imaging 6 in medical and security applications.

Light wavelengths in the adjacent band shorter than 400 nm and longer than 10 nm are referred to as the ultraviolet band 4 with those closest to visible light referred to as near UV and the shortest wavelengths in the hand as extreme UV or deep UV. Just beyond the ultraviolet band, the X-ray band 5 comprises soft X-rays down to wavelengths of 0.1 nm and hard X-rays beyond that. Soft X-rays are used in security applications 7 for cargo and passenger inspection while shorter wavelength X-rays are used in X-ray crystallography, in radiography 8, and in computerized tomography or CT scans.

All EMR is the propagation of energy through space and in matter achieved through a time-varying electric field and a corresponding complementary magnetic field created through the movement or vibration of charged particles. Since the time-varying electric field induces a corresponding time-varying magnetic field, and conversely the time-varying magnetic field induces an electric field, EMR can travel without any medium, even in the vacuum of space. Its ability to penetrate matter depends on the absorption and scattering properties of the matter at each particular EMR wavelength.

Traveling in space or in matter, EMR is able to manifest itself as either a particle or a wave (but not both at the same time). When EMR manifests itself as a particle it is commonly referred to as a "photon", while when it behaves in a wavelike manner it is often referred to as "light waves". The term "light", then, is used in two ways—in the general sense to mean any electromagnetic radiation in the spectrum, and in the specific case to mean only visible light and its spectral neighbors ultraviolet light and infrared light.

When EMR does come in contact with matter, it may be reflected, pass through the matter or be absorbed altogether, affecting the EMR and often changing the matter too. EMR's interaction with matter may manifest itself with particle like behavior governed by classical physics (first historically in the "Compton Effect"), as a wave exhibiting any combination of classical wave-like phenomena such as reflection, refraction, or interference, or by quantum mechanical effects such as quantized energy band transitions, molecular transformations, or quantum mechanical tunneling. Such interactions between matter and EMR have been harnessed for a large number of commercial, scientific, and medical applications.

Interactions of EMR and matter have been used extensively in scientific research, especially in imaging and analytics. X-ray diffraction allows for precise analysis of crystalline morphology and even played a crucial role in the discovery of DNA. EMR is also used extensively for medical imaging. Today, X-rays are routinely employed in radiography 8 to identify broken bones and dental cavities and in CT scans to identify tumors and tuberculosis. Imaging can also be performed using infrared light 6 often to analyze tissue where X-ray analysis is inconclusive or inconvenient. Advanced research also includes new hand held IR imaging devices that can identify carcinoma in tissue during surgery, particularly useful in identifying and removing cancerous cells in the border tissue during a mastectomy, avoiding the need for costly delays waiting for lab results and the repeat surgeries that result from the delayed lab analysis.

EMR also plays an important and growing therapeutic role in medicine. In some cases EMR is used to kill foreign or unhealthy cells while in other examples EMR is used to stimulate healing, promote immune response, reduce pain, and alleviate local inflammation.

Perhaps the best-known and oldest therapeutic use of EMR is radiation therapy 9, applied primarily in the treatment of cancer. Because such radiological protocols involve exposing a patient to ionizing radiation in the X-ray band 5, patients often suffer serious side effects from radiation poisoning that compromise the medical benefit by lowering a patient's quality of life. The goal of radiation therapy is to achieve targeted cellular destruction of the cancerous cells without damaging or killing a significant number of normal cells. Research continues in localizing the radiation to minimize the collateral damage to normal cells. In many cases, however, it is simply a matter of statistics—a race to destroy most of the cancer before the treatment kills the patient.

Another therapeutic protocol of EMR using less energetic photons than X-rays employs ultraviolet light 4 to remove unwanted antigens and bacteria from the skin. One common example of UV phototherapy is the anti-bacterial use of ultraviolet light 11 locally applied by dermatologists to treat skins rashes and irritations, in essence to "sunburn" whatever may be present on a patient's skin causing a rash or itching. Its use is often indicated even when the actual cause of an irritation cannot be confirmed.

In general, to destroy or otherwise inhibit the growth of mutated, pre-cancerous, cancerous, or un-normal cells requires the concentration of EMR into a narrow bandwidth and a focused area to avoid damaging healthy cells. Applying a focused beam to treat large areas is problematic—especially once metastasis has commenced. Research in using beams of focused energy to perform targeted cellular destruction spans the spectrum from the far infrared to hard x-rays.

EMR is also used for therapies not targeting cellular destruction, but instead to promote natural healing processes within the body. In thermotherapy 10, long wave infrared heating either through lamps or LEDs is used to raise a patient's body temperature to that similar to temperatures experienced from mild exercise. Research shows thermotherapy benefits patients suffering from severe cardiovascular disease unable to exercise by improving cardiovascular flow over large areas and volumes of the circulatory system.

Another EMR therapy, herein referred to as photo-optical stimulation 12, is used to counter depression and anxiety in people by visually stimulating a patient's eyes with artificial colored or white light (essentially emulating sunlight or portions thereof) to enhance their mood and provide a sense of wellbeing. Such photo-optical stimulation treatments are especially important for residents of Polar Regions where extended periods of darkness prevail for the majority of winter days, and where alcoholism and suicide rates greatly exceed that of the general population globally. Photo-optical stimulation treatments have also been used to counter severe jet lag and to restore and help regulate sleeping patterns.

Photobiomodulation

Referring again to FIG. 1, phototherapy 14, the emerging medical field to which the apparatus of this disclosure relates, herein is broadly defined as the therapeutic application of light to beneficially affect cells and tissue through photobiomodulation and the photoexcitation of No-molecules.

Photobiomodulation, the electrochemical response of cells and tissue to direct illumination by ultraviolet, visible and infrared light, represents a physical mechanism by which energy is imparted directly into a cell by photons to produce any number of photobiological responses, including forming ATP (a molecular source of energy), accelerating intracellular and intercellular chemical reactions, stimulating DNA transcription and RNA translation (protein synthesis), increasing intracellular catalyst concentrations, and beneficially affecting the cell and its host. Depending on the wavelength of the impinging light, photobiomodulation has been observed in virtually every living creature on earth from bacteria to complex organisms, including animals, mammals, and even HOMO sapiens. Since, in many cases, photobiomodulation stimulates the formation of ATP and initiates protein synthesis, it means (at the right frequencies of light) photosynthesis occurs not only in bacteria and in plants, but also in animals.

One of the early observations of photobiomodulation was reported in 1967 by a researcher studying the biological effects of infrared laser light on animals. Convinced the laser light caused cancer, the researcher shaved mice then irradiated half of the population with low-level infrared light only to discover not only did the mice not contract cancer, but much to the researcher's surprise, the irradiated mice's hair grew back at a greatly accelerated pace.

The report was largely forgotten until later and quite accidentally) photobiomodulation was essentially re-discovered by NASA during the space shuttle program, observing astronauts exposed to infrared light from a plant grow lamp healed normally when those from prior missions absent the grow lamp did not heal normally. Further research identified mice poisoned with methanol and treated with infrared light retained most of their vision while the control group went completely blind. The study identified methanol molecules which normally attach to the adenosine triphosphate (ATP) chemical bonding sites in the optical nerve (and essentially starve the nerve tissue for energy) are dislodged and replaced by ATP generated by photobiomodulation of infrared light. The significance of this study was its early identification of ATP and its role in the photobiological process.

Molecular studies on bacteria and plankton subsequently revealed that light (especially in the visible red and near infrared portion of the spectrum 13) is absorbed directly by a biomolecule cytochrome C oxidase (CCO). The CCO molecule acts as an intracellular battery charger converting adenosine monophosphate (AMP) into adenosine diphosphate (ADP), and then into adenosine triphosphate (ATP). If metaphorically. CCO is the battery charger, then ATP is a cell's battery—the battery powering all the other electrochemical reactions within the cell itself.

Studies on mice and human patients found photobiomodulation of injured tissue or organs resulted in cellular repair, tissue regrowth and accelerated healing, improved immune response, reduced tissue inflammation, lower secondary infection risk, and faster recovery from injury or illness. In human trials, patients also reported reduced pain and improved health following only a few phototherapy treatments. In patients suffering from peripheral neuropathy, i.e. the death of nerves in limbs common in diabetes sufferers, partial recovery of their sense of touch was also noted. Numerous refereed professional journals (e.g. journal of Lasers in Medical Science) and various textbooks are available today summarizing the discovery of photobiomodulation and its prospects for therapeutic treatments, i.e. for "phototherapy" [Charles T. McGee, "Healing Energies of Heat and Light" Medipress, Coeur d'Alene, 2000].

To date, photobiomodulation and its potential therapeutic effects have been studied for over four decades. Despite exciting, almost unbelievable early results, decades passed without doctors or scientists finding a practical or commercially viable means by which to bring phototherapy to market, due to limitations in understanding and more so in the technology of the day.

As shown in FIG. 1, phototherapy may be performed using either incoherent light 17 or by lasers 15. Initially, incoherent light from the sun and later from lamps was used, in part because of its broad-spectrum 17A and its ability to cover a large area 17B. Lamps however were found to be unwieldy, consuming large amounts of power and producing more heat than light. Subjects complained of overheating and researchers suffered burns from handling the hot incandescent bulbs. Other studies especially in the USSR, focused on applying ceramic infrared lamps adapted from industrial ovens and heaters, into phototherapy. These efforts concentrating primarily in the long wavelength portion of the spectrum include both beneficial phototherapy as well as targeted cellular destruction. Later, scientists also attempted treatments using gas discharge lamps ands noble gasses but were limited by their inability to control the radiated wavelengths.

Research then turned to lasers 15 operating at much cooler temperatures than bulbs and beneficially producing more light than heat. At first it was thought that coherent light would impart an added advantage in penetration depth and treatment efficacy but it was soon discovered that the small spot size 16B of a laser made the treatment of large areas such as a whole organ or large muscle problematic. Further studies also revealed that optical coherence was almost immediately lost from scattering in the top layers of the skin anyway, so that deep penetrating light was not coherent even when emanating from a coherent source. Moreover, gas and dye lasers were costly, fragile, large, heavy, power hungry, and inconvenient to transport. Other studies revealed that too narrow of a frequency-spectrum 16B typical of laser light might adversely reduce phototherapy treatment efficacy.

While the advent of the semiconductor laser diode helped lower the potential cost of laser phototherapy, the small spot size of laser diodes combined with a characteristically narrow bandwidth remain problematic. Moreover, laser medical devices continue to pose a potential safety risk to both patients and clinicians and require strict compliance with an ever-changing set of governmental regulations. As such, the broad scale commercial deployment of phototherapy devices based on the use of laser diodes still face numerous challenges.

In contrast, the recent commercial availability of relatively low-cost bright LEDs offers a more promising means by which to engineer a practical phototherapy device. Unlike laser diodes, LEDs are rapidly emerging as the preferred source of light to be employed in a virtually unlimited range of applications. Today LED lighting exclusively provides the backlight and camera flash in virtually every mobile phone and smartphone sold. LEDs also facilitate backlighting for the newest generation LCD HDTVs offering "green" (i.e. energy efficient) operation and enhanced image contrast. Since 2010, the LED began expanding into general lighting applications including automobile headlamps, tail lamps and cabin lighting; into streetlights, and even into commercial and residential lamps replacing inefficient incandescent bulbs and obsoleting hazardous mercury-contaminated compact fluorescent lamps (CFLs).

With its ubiquitous use driving high production volumes, the resulting economy of scale benefits, supplier competition, and new technology continue to drive LED costs lower, further enabling the LED's competitive advantage in the global marketplace. Moreover, the LED's exceptional safety record prompted the United States government to further relax LED safety regulations, distinguishing the LED as a separate and distinct category from lasers and laser diodes, authorizing unrestricted use provided an LED's power output does not exceed the FDA's guideline of 300 mW/cm$^2$.

LED Flashlight and Torchlights

One requirement for effective LED phototherapy is an electro-optical design capable of maintaining a consistent LED current for extended treatment durations, e.g. at least 60 minutes or longer. Low-cost LED driver circuitry and designs used in flashlights, torchlights, and many phone backlights, however, lack the necessary features and capability to adequately control LED brightness over such extended durations, or to distribute light uniformly. They also lack the ability to perform a number of important functions useful in customizing treatments to specific medical conditions, e.g. by modulating LED excitation to vary its operating frequency. FIG. 2, for example, illustrates a conventional low-cost LED driver where four series connected batteries 20a through 20d power one or more parallel strings of LEDs 26a through 26n with each string comprising "m" series connected LEDs.

Counter 23a and inverter 23b, collectively as digital controller 23, digitally oscillate at a fixed clock frequency by repeatedly switching MOSFETs 27a through 27n on and off, in turn toggling on and off LED currents $I_{LED1}$ through $I_{LEDn}$ in the LED strings 26a through 26n. By varying the pulse width and corresponding duty factor D of the LED current conduction time by controller 23, strobe operation of the LEDs is able to facilitate fixed frequency PWM brightness control.

Unfortunately, a fundamental problem with the circuit as shown is that it powers the LED strings with a voltage source, not current sources. LEDs prefer, i.e. behave better, being driven by constant current sources. Voltage source drive cannot balance the current evenly among the LED strings 26a through 26n because the LED forward voltages do not match one another, varying stochastically with manufacturing and also varying dynamically with operating current and brightness. Series ballasting resistors 24a through 24n are included in an attempt to balance the current more evenly among the LED strings but they still do not guarantee matching of current or LED brightness.

Unlike current source drive, using a voltage source and a resistor allows the LED currents and brightness to change with the power supply voltage, i.e. with the decay in the battery voltage. As shown in FIG. 3, as the battery voltage $V_{batt}$ 30 declines, the potential difference between it and the LED string voltage $V_{LED}$ 31 declines in proportion. Since the LED current in any given string is given by $$I_{LED} = (V_{batt} - V_{LED})/R$$

then any change in $V_{batt}$ over time will manifest itself as a time dependent change in LED brightness. When $V_{batt}$ approaches $V_{LED}$ during the battery's decay, the LEDs eventually turn off and cease to illuminate. LED strings with a higher forward voltage will dim faster and turn off sooner than lower forward voltage strings causing inconsistent LED brightness over time and poor luminous uniformity as well.

Returning to FIG. 2, in order to prevent flicker resulting from switching noise and current transients among channels, capacitors 25a through 25n are added for filtering. Low dropout (LDO) linear regulator 21 and filter capacitor $C_{reg}$ 22 are also included to provide a consistent voltage $V_{driver}$ to supply digital controller 23 despite variations in the output voltage $V_{batt}$ of battery pack 20 during discharge and with LED current transients. While LDO 21 could also be used to power LED strings 24a through 24n, the extra voltage drop across the LDO adversely affects the device by diminishing the peak LED brightness, increasing power dissipation, and resulting in the LEDs shutting off sooner than they would otherwise.

In the design, the maximum number of series connected LEDs "m" depends on the LED forward voltage, the battery chemistry and the resulting battery voltage $V_{batt}$. If battery 20 comprises a rechargeable LiIon chemistry each cell exhibits a nominal voltage of 3.6V and $V_{batt}$=14.4V. If red LEDs are used with a forward voltage of 1.6V each, then "m" may be chosen for 8 or 9 LEDs. If infrared LEDs are employed, each LED has a forward drop of 2.2V so that "m" is limited to 5 or 6 series LEDs. If strings of red LEDs are alternated the string-to-string voltage and current mismatch problem will be further exacerbated. The LED torchlight drive shown simply cannot accommodate such mismatches in voltage and current, and therefore mixing LED types is problematic.

In consumer devices, however, alkaline batteries are far more common than expensive rechargeable LiIon cells. In such cases, each cell starts at approximately 1.5V but gradually decays to 1V per cell, with the battery voltage ranging from slightly over 6V and decaying to 4V and beyond. During the discharge, the LED brightness will decline constantly during use. At 4.2V, the LEDs no longer illuminate and the batteries must be replaced to continue use.

Attempt to regulate the LED voltage by introducing a voltage regulator between battery pack 20 and the LED strings only makes the problem worse because the converter itself, consumes power further shortening battery life. If the converter is another LDO similar to LDO 21, the voltage drop across the LDO actually shortens the battery life. If an expensive boost converter is employed producing a fixed voltage higher than $V_{batt}$, a new problem occurs. Since the forward drop across LED strings varies stochastically with manufacturing, at higher operating voltages and correspondingly, with a larger numbers of series connected LEDs, variations in LED voltage can be substantial, especially during the entire manufacturing life span of a product.

To insure every LED string always has sufficient voltage to illuminate at specified current the fixed voltage output from a boost converter must exceed the highest string voltage expected in the course of manufacturing. This design approach naturally results in a "high" supply voltage—one higher than needed for normal units having LED voltages near the statistical mean. The unused excess voltage produces heat in the driver circuit in resistors 24a through 24n and in MOSFETs 27a through 27n, lowering efficiency and shortening battery life. In LED strings having LED voltages below the mean, i.e. at the low end of the distribution, the extra voltage can become excessive, even causing overheating in the drive circuit. If the LED current is also varied, the problem becomes further exacerbated because the LED string voltage is also a function of operating current.

Mechanical design represents another significant limitation of LED torchlight designs. FIG. 4A illustrates an artist's conceptualization of LED torchlight 35 typical to this genre of phototherapy products. The torchlight or "wand" has a handle portion and an LED portion comprising an array of LEDs 35a. The LED array is stiff and inflexible with the LEDs essentially coplanar mounted on a circuit board housed within wand 35. Other versions embed the LEDs within a hairbrush.

The first problem of this design is the practical consideration of treatment time. Phototherapy achieves photobiomodulation by introducing a sufficient number of photons into tissue to change the electrochemistry of cells in the treated tissue. The maximum rate photons can be introduced into tissue is practically limited to the highest LED brightness to avoid skin burns and to comply with government regulations. Considering these aspects, minimum treatment times are in the range of 20 minutes to 60 minutes depending on the tissue being treated. Times shorter than the prescribed amount are completely ineffective, analogous to plugging a phone into a battery charger for only a couple of minutes. In such a short duration, the electrochemistry of a cell, like a battery, does not normalize and energy is not absorbed in any beneficial way.

Holding a wand on your skin in one specific place for 60 minutes without moving it is just not possible. Any movement changes the treatment conditions. As shown in the leftmost example of FIG. 4A, when LED wand 35 is held above the skin at a distance, photons spread over a large area but are primarily absorbed by the outer epithelial layers of skins, barely penetrating into the subdermal tissue 37. Slightly moving the wand 35 as in the middle graphic results in an entirely different therapy volume, being smaller in area and deeper in penetration. The right most case shows close proximity treatment, illuminating a surface area no larger than that of the LED array 35a but penetrating deep into subdermal layers 37 To cover a large area at close proximity, a patient would be required to hold the wand in a fixed position for long durations multiple times until all the area was treated. Such an exhaustive procedure is simply not practical especially for patients suffering duress from illness or pain. Likewise, no clinic can afford to hire a nurse to sit with a patient during the entire treatment just to hold LED wand 35 in place.

Expanding the size of wand 35 doesn't solve the area problem either. Making the LED area 35a larger further exacerbates the issue of achieving uniform penetration depth over large areas, especially because most treatment areas on a patients involve curved surfaces, e.g. a leg, arm, neck, side, etc. As shown in FIG. 4B, illuminating curved body surfaces with a stiff planar LED array results in a continuously variation distance between LED and skin, resulting in a large variation in photon penetration depth 38. As illustrated, the portion of planar LED array closest to the skin in the center of the array will penetrate deeper than the edges.

The tighter the curvature of the treated body part, the worse the uniformity problem becomes, with arms and legs and fingers suffering the poorest illumination uniformity.

Combining the low cost LED torchlight drive circuitry with a flat wand or flashlight illuminator shape renders such consumer oriented completely impractical to use and ineffectual in their result. Given these severe design issues, such consumer "gadgets" cannot be considered as real phototherapeutic devices or as prior art apparatus or method for achieving photobiomodulation or delivering phototherapeutic treatments.

HDTV Backlight Drivers

State-of-the-art for the electronic drive of LED arrays today is best exemplified by integrated circuits (IC) for LED backlighting of large LCD (liquid crystal display) panels, especially those used in LED backlit HDTVs (high definition televisions). While the end application, design, operation, and software programming of these systems have been specifically designed and created for driving white LEDs in LED backlit HDTVs, the hardware and IC implementation of such systems is vastly better than the torchlight driver circuitry used in present day phototherapy devices and consumer gadgetry.

FIG. 5A illustrates the basic elements of a LED backlit HDTV comprising a liquid crystal display (LCD) panel 42, a color filter 43, and a LED backlight including an array of white LEDs 41 and LED backlight driver IC 45. TV viewers 44 observe color 2D or 3D images on the LCD panel by seeing light produced by the array of white LEDs 41 penetrating some fraction of the pixels, i.e. picture elements, in liquid crystal display panel 42 and passing through color filter 43. LCD panel 42 acts like an adjustable window-blind offering 256 or more "grey scale" levels of light transmissivity ranging from black (opaque) to full brightness (transparent) and every intermediate brightness. The combination of black, white, and grey pixels forms two-dimensional (2D) images on the display as seen simultaneously by both left and right eyes of observer 44.

Transmitted light passes through color filter 43 with the light from any given LCD pixel passing only through one of three colors—red, green, or blue. Because white light emanating from white LED 41 contains all the colors of the rainbow, color filter 43 is able to filter each pixel into one color only, either red, blue or green, For example, a red color filter actually absorbs all the colors except red light, removing blue green, violet, etc., to give the light a red color.

The combination of all three colored pixels, one red, one blue and one green, can then be used to recreate images with virtually any color in millions of shades and brightness levels. Such a display is referred to as a RGB color LCD. The data sent to each red, green, and blue pixel are processed by a video processor IC and set to a combination of row and column drivers, managed by a complex digital video timing controller. A new picture is loaded and rescanned at a fixed period known as the vertical synchronization or Vsync pulse which typically occurs a rate of 60 Hz in older TV models and at 120 Hz or 240 Hz in today's newest high performance HDTVs.

Synchronized to the LCD image and to the Vsync pulse, LED backlight driver 45 controls the brightness of the array of white LEDs 41 using pulse width modulation (PWM) brightness control operating a fixed clock frequency and updated once every Vsync pulse. The backlight may be uniform in brightness operating at a single duty factor D and adjustable in brightness for the entire display. Uniform backlight brightness of an LCD backlight is referred to a global dimming control. Alternatively, the backlight may be broken into tiles or segments with each tile illuminated to the proper brightness corresponding to the image in that portion of LCD panel 42 located directly above the backlight tile. By varying the LED brightness in conjunction with the image, e.g. where dark portions of the image are illuminated by a dimmer LED backlight, power is saved and image contrast enhanced. Using local dimming, blacks look blacker, and bright images look brighter, for the first time enabling the means for "mega-contrast" performance in LCDs comparable to that of power hungry plasma displays.

Local dimming in LED backlit LCDs is achieved by "current control" of LED string currents using ground-connected current sources, commonly known as "current sinks" as shown in FIG. 5B. These current sinks 56*a* through 56*n* individually respectively control the current in LED strings 57*a* through 57*n*. Each current sink includes feedback (schematically represented by a current sense loop and analog input to each dependent current source) to dynamically adjust gate drive of the transistors comprising said current sink in order to maintain a preprogrammed value of sink current independent of voltage. Each current sink 56*a* through 56*n* is toggled on and off by digital signals 58*a* through 58*n* respectively.

These digital signals are output from LED driver circuit 55 comprising LED driver ASIC 56 a set of digital buffers needed to drive the line capacitance of signals 58*a* through 58*n* distributed across the LED backlight board. Switched at a fixed frequency, the digital signals 58*a* through 58*n* each vary independently in duty factor D to adjust the corresponding current and brightness of each LED string 57*a* through 57*n*. Global dimming and overall brightness control is performed by operating each LED string at the same duty factor D. Operating each string at its own unique duty factor $D_1$ through $D_n$ performs local dimming in response to instructions received from video scalar IC 54 communicating to LED driver 55 through digital SPI bus 59*a*. In some cases the video scalar IC 54 communicates to a microcontroller (not shown), interpreting and in turn instructing LED driver 55 regarding the proper drive for each LED string for local dimming.

As shown, switch mode power supply 52 and filter capacitor 53*c* power all the LED strings at a regulated voltage $+V_{LED}$. White LEDs are generally constructed using wide bandgap materials to produce blue light. The blue light is subsequently converted into white light by phosphor in the LED lens. Because white LEDs employ wide bandgap materials, the voltage drop across white LEDs is quite high, typically 3.5V to 4V per LED. This means the output of SMPS 52 is often high voltage, ranging from 60V when in, the number of series connected LEDs, is below 15, to over 200V for larger values of m.

The voltage rating of capacitor 53*c* should be scaled accordingly with its capacitance value Creg3, sufficient to stabilize the regulator's control loop and adequate to support the worst-case LED transients without dropping out of regulation. Individual ripple filtering capacitors on each LED string (like those shown in FIG. 2) are not needed in this design because current sinks 56*a* through 56*n* maintain the individual LED currents ILED1 through ILEDn despite fluctuations in voltage arising from transient voltage drops or string-to-string voltage mismatch. In battery powered applications such as a notebook computers Vin is typically in the range of 15 to 20V, SMPS 52 typically comprises a boost converter and Vlogic and Vdriver are regulated using LDO linear regulators 50 and 51.

In monitors and HDTVs, the input voltage is typically the AC-mains, either 110 VAC or 220 VAC, and SMPS 52 is generally an isolated flyback converter. In such cases SMPS 52 often includes a second output, typically 24 VDC or 12 VDC, sued to power LDOs 50 and 51.

As shown in FIG. 6A, PWM brightness control in 2D HDTVs if performed using a fixed frequency clock pulse to generate a programmable duty-factor-controlled LED (output) current waveform. A microcontroller, video processor IC, or timing generator IC generates a vertical sync signal Vsync 60 having a period $T_{sync}$ typically corresponding to a frequency of 60 Hz, 120 Hz, or 240 Hz. The lowest of these frequencies, i.e. 60 Hz, was chosen historically to be the lowest frequency that was sufficiently fast that the human eye could not see the screen image change or flicker. More recently double or quadruple Vsync frequencies have been used to reduce image blur and to facilitate 3D displays. The Vsync pulse acts as the main clock in an LCD or HDTV as it is used in a variety of functions including the instruction to load video data from the video processor into the LCD column drivers, to advance the LCD scan by one row, and to load information into the LED backlight driver control registers.

In an LED backlit HDTV offering brightness control, a second clock 61 is generated and synchronized to the Vsync clock 60 but operating at a higher frequency. For example in a HDTV offering 4096 levels or 12-bits of dimming control, the second clock, sometimes referred to as a grey scale clock or GSK, runs at a frequency $f_\theta$ that is 4096 times faster than the Vsync pulse rate, i.e. having a grey scale clock period of $T_\theta$=Tsync/4096. By employing programmable counters in an LED driver IC, the average LED brightness can be varied from 0% to 100% in 4096 steps either locally or globally, each step representing approximately 0.0244% variation in backlight brightness.

This backlight brightness control and dimming feature can be implemented without the need to change LED conduction current. In the graph for Current Reference 62, the value of LED current in any channel set by the precision Current Reference 62 remains constant at a user programmable value 62a equal to $I_{ref}$ throughout. Instead of changing currents, the duty factor D is varied dynamically to adjust backlight brightness. Referring again to FIG. 6A, the LED on-time is initially operated at an specific on-time $t_{on1}$ resulting in a 66% duty factor shown by curve 65a where $$D_1 = t_{on1}/T_{sync} = 66\%$$

meaning during each Tsync period prior to time $t_1$, LED (Output) Current 63 operates two-thirds of the time in an on-state 64a conducting a current equal to $\alpha I_{ref}$ and one-third of the time 64b in an off-state at zero current. Described in terms of the programmable counter and Clock 61 switching at frequency $f_\theta$=4096/Tsync, the on-time and off-time for 66% duty factor operation is 2730 clock pulses and 1366 clock pulses respectively. The average LED current and therefore LED brightness shown by curve 65a represents a level 66% that of the pulsed current value $\alpha I_{ref}$.

Between time $t_1$ and time $t_2$, the brightness control changes to a duty factor of 50% as shown by average value 65b, so that $$D_2 = t_{on2}/T_{sync} = 50\%$$

and where $t_{on2}$ digitally represents 2048 clock pulses, or half the number of the period's 4096 pulses. Similarly between time $t_2$ and time $t_3$, is the brightness control increases to a duty factor of 75% as shown by average value 65c, where $$D_3 = t_{on3}/T_{sync} = 75\%$$

and where $t_{on3}$ digitally represents 3072 clock pukes, or three-quarters of the period's 4096 pulses. After time $t_3$ the average duty factor 65d drops to only 12% or 491 pulses per period. Backlight operation at such low duty factors typifies sleep mode operation where a display is dimmed dramatically to reduce power consumption, save battery life, or improve a display's green power rating.

FIG. 6B shows the waveforms for the same display changing operation from 2D mode into 3D mode. Three dimensional image display in HDTVs, also known as 3D mode, involves alternately displaying two images, one for the left eye, the other for the right eye, and switching the images at a sufficiently high rate that the eye cannot see the alternating images. The left and right images are separated using glasses worn by the viewer that only allow the left eye to see the left eye image and only allow the right eye to see the right eye image. This may be accomplished using passive glasses comprising two different polarizing filters and by changing the polarization of the display image in alternating fashion to direct the image to the corresponding eye. Alternatively, active glasses comprising LCD shutters synchronized to the display images may be used to control which eye sees which image.

In any event, because only one eye sees the display's image at a time, the duration by which the image is displayed must be half the time of that in 2D mode. To avoid the perception of flicker the image must be scanned at twice the normal Vsync. For example if a HDTV normally operates a 60 Hz Vsync rate, then in 3D mode the display and the backlight must operate at 120 Hz. If a HDTV normally operates at 120 Hz in 2D mode, in 3D mode the Vsync rate is doubled to 240 Hz.

As shown prior to time $t_7$, the Vsync pulse occurs at a fixed rate with a period $T_{sync}$ for normal 2D mode operation, after which, the Vsync rate doubles to a pulse with period $T_{sync}/2$. At time $t_7$, Grey scale Clock 61 also doubles in frequency from $f_\theta$ (2D mode)=4096/$T_{sync}$ to a rate $f_\theta$ (2D mode)=4096/$T_{sync}$. Although the clock rate doubles, since the programmable counter relies on the clock, the duty factor stays constant. For example, between time $t_6$ and time $t_7$, the brightness control has a duty factor of 50% as shown by average value 65f, whereby $$D_7 = t_{on7}/T_{sync} = 50\%$$

After the frequency doubles at the onset of 3D operation, $t_{on8}$ is reduced to half the value of $t_{on7}$, i.e.

$$t_{on8} = t_{on7}/2$$

But likewise, $T_{sync3D}$ is reduced to $T_{sync}/2$ so that $$D_8 = t_{on8}/T_{sync3D} = (t_{on7}/2)/(T_{sync}/2) = D_7 = 50\%$$

So changing the Vsync frequency has no bearing on the PWM duty factor or PWM brightness, as shown by duty factor curves 65f and 65g. But because in 3D mode only eye is seeing the display image at a time, the human mind perceives the brightness as half that of normal brightness. To compensate for this effect, the brightness of the LED backlight must doubled in 3D mode from $\alpha I_{ref}$ to a value of $2\alpha I_{ref}$. In other words, the brightness of the LED pulses doubles in brightness in 3D mode but since only one eye sees them at a time, there appears to be no change of brightness compared to 2D mode.

A TV backlight driver IC capable of performing all these operations is illustrated schematically in FIG. 7 comprising channel drivers 69a through 69n and control section 69z (collectively as LED driver 69) driving LED strings 57a through 57n powered by SMPS 52. In this system, video information from video scalar IC 54 is transferred via SPI bus 59a to microcontroller 67. Microcontroller 67 interprets this video information and passes it to the control section 69z of LED driver IC 69, specifically via SPI bus interlace 59b. The SPI bus then distributes the information to decoders 74a through 74n using digital bus 73 which instructs the individual channel drivers on drive conditions including timing and biasing. For high speed data transmission with a minimal number of interconnections, digital bus 73 represents some combination of serial and parallel communication. Since the bus is dedicated to the LED driver, such a bus may conform to its own defined standards and is not subject to complying with any pre-established protocol as SPI bus 59a and 59b are.

This digital information from digital bus 73, once decoded by decoders 74a through 74n, is next passed to digital data registers, i.e. data latches, present within each individual channel driver 69a through 69n. In the schematic of FIG. 7, the decoded data includes a 12 bit word defining up to 4096 increments in duty factor D, for brightness control, a 12 bit word defining up to 4096 increments in phase delay φ used to compensate for propagation delays across a panel and to minimize power supply inrush currents, and a 8 bit word Dot for setting the LED currents used in current calibration to improve backlight uniformity (i.e. dot correction) and used to switch between 2D and 3D display modes.

For example, synchronous to each vertical sync pulse on Vsync line 60, decoder 74a loads a 12-bit word into D register 75a, a 12-bit word into φ register 76a, and a 8-bit word into Dot register 77a contained within individual LED drive channel 69a. In similar fashion and synchronous to Vsync pulse on line 60, decoder 74b loads a 12-bit word into D register 75b, a 12-bit word into phase delay φ register 76b, and a 8-bit word into Dot register 77b contained within individual LED drive channel 69b. The same process occurs simultaneously for all n channels, i.e. from channel drivers 69a through 69n.

Once the data from decoder 74a is loaded in duty factor D register 75a and phase delay φ register 76a, counter 78a begins to count pulses present on Clock $f_\theta$ line 61, the output of counter 78a determined the timing of precision gate bias circuit 70a to toggle current sink MOSFET 71a on and off. By controlling the timing of conduction of current $I_{LED1}$ flowing in LED string 57a including its duty factor D, i.e. its on time each Vsync period, the brightness of LED 57a is precisely controlled. The bit data loaded into Dot register 77a is simultaneously interpreted by D/A converter 79a to set the reference current $\alpha I_{ref}$ feeding precision gate bias circuit 70a. This reference current sets the analog magnitude of LED current $I_{LED1}$ flowing in MOSFET 71a and in LED string 57a whenever the particular channel is toggled on and conducting. It has no bearing of the MOSFET's current when counter 78a toggles the particular 69a channel off. The same process occurs simultaneously for all n channels, i.e. from channel drivers 69a through 69n.

The value of reference current $\alpha I_{ref}$ is set in any given channel driver in two ways. Firstly the value of $I_{ref}$ is set by a precision resistor $R_{set}$ present in each channel driver 69a through 69n. A precision trimmed voltage reference $V_{ref}$ present within LED driver IC 69 (but not shown) is converted into the precision reference current $I_{ref}$ by the value of the resistor $R_{set}$ such that $I_{ref} = V_{ref}/R_{set}$. The resistor $R_{set}$ may be integrated provided that it is trimmed for absolute accuracy during manufacturing, or may comprise a discrete precision resistor, one per channel, externally connected to each channel of LED driver IC 69. While the value of $R_{set}$ could conceivably be varied from channel-to-channel, it is generally preferable to use precisely the same value of $R_{set}$ in every channel to maximize the channel-to-channel matching and to vary the channel reference current through the digitally controlled value of the parameter α, as determined by the digital value stored in the Dot register of every channel.

For example in channel driver 69a, the 8-bit word stored in Dot register is converted into one of 256 levels for the multiplier α, allowing the current in MOSFET 71a and in LED string 57a to be set anywhere from 0% to 100% $·I_{ref}$ in 256 steps, i.e. in increments of 0.39% per step whenever MOSFET 71a is on and conducting. The same operation occurs in all channel drivers 69a through 69n, enabling digital control of LED current in every LED string 57a through 57n via digital bus 73.

It should be noted that in an LED backlit HDTV it is preferable to change LED brightness using the digital PWM dimming method and counters 78a through 78n than it is to use Dot registers 77a through 77n changing the corresponding value of $\alpha I_{ref}$ in each channel, primarily because the color temperature of white LEDs is a function of current. Running the LED strings across the display at dramatically different currents can adversely result in color aberrations in the display image.

To maintain the proper current in every LED string including the LED string with the highest forward drop, current sense feedback circuits CSFB 72a through 72n have been included to determine in real time which string exhibits the highest voltage and to use that information as feedback to SMPS 52 to set its output $+V_{LED}$ to a voltage just slightly higher than the LED string with the highest forward voltage.

The CSFB circuits are connected in daisy chain fashion, i.e. in series "head to toe", with the input 73b into CSFB circuit 72a coming from the output of CSFB circuit 72b, the input 73c into CSFB circuit 72b coming from the output of CSFB circuit 72c (not shown), and so on. Each CSFB circuit passes the lower of its input voltage or the voltage on the drain of the corresponding current sink MOSFET in the channel to its output, until the last CSFB circuit 72a has an output 73a representing the lowest drain voltage in the IC (and hence the highest forward voltage LED string) provided as the CSFB feedback signal to SMPS 52. The first CSFB circuit in the string CSFB 72n must have its input tied to the highest convenient voltage, e.g. $V_{logic}$ or $V_{driver}$.

Since, however, all the LED strings in a LCD backlight for color HDTVs are white LEDs, probably from the same manufacturer and even the same production batches, the variation in forward voltage of the LED strings primarily results from natural stochastic variability in the LEDs' manufacture, not from functional differences in the types of LEDs being driven.

SUMMARY OF BACKGROUND

In conclusion, prior attempts to adapt LED technology for photobiomodulation and medically for phototherapy suffer from grossly inadequate flaws in their mechanical and electrical design. The LED driver circuitry used to implement early attempts at phototherapy essentially comprise constant voltage drive LED torchlights unable to maintain consistent LED operation under conditions of changing voltages, LED currents, or fault scenarios. Operating essentially as fixed frequency lamp dimmer circuitry, they also lack the ability to facilitate pattern sequencing and waveform synthesis—sequences and waveforms potentially beneficial in maximizing photobiomodulation and the therapeutic benefit therewith.

Similarly inadequate, the hardware of present day LED arrays suffer from mediocre mechanical design resulting in poor reliability from excessive wire interconnections in the LED array and an inability to maintain a constant position or conform the shape of an LED array to a patient for a consistent optical penetration depth, especially during treatments necessarily exceeding tens of minutes, or longer.

While constant current LED backlight driver ICs for HDTVs electrically include better functionality for driving large arrays of LEDs than the aforementioned LED torchlight designs, their features are specifically engineered to address issues in illuminating LCD displays including synchronization to video display timing signals and the ability to adapt in brightness in response to video content—functions completely irrelevant to implementing a phototherapeutic device. Moreover, in their present form, such HDTV backlight drivers do not enable or even anticipate the need for generating complex waveforms, performing algorithmic sequencing, synthesizing varying frequencies, or driving inhomogeneous LEDs, ones of differing construction, wavelength and forward voltages.

What is needed is a new design for LED phototherapy implemented to deliver the highest degree of photobiomodulation uniformly and consistently for extended durations, ideally with extensive program flexibility and features controllable by the attending physician.

BRIEF SUMMARY OF THE INVENTION

In the phototherapy process of this invention, defined patterns (e.g., square-wave pulses) of electromagnetic radiation (EMR) having one or more wavelengths, or spectral bands of wavelengths, are introduced into a living organism (e.g., a human being). The radiation is normally within the infrared or visible parts of the EMR spectrum. EMR of a single wavelength may be used, or the pattern may include EMR having two, three or more wavelengths. Rather than consisting of radiation of a single wavelength, the EMR may include spectral bands of radiation, often represented as a range of wavelengths centered on a central wavelength, e.g., $\lambda \pm \Delta\lambda$. The pulses may be separated by gaps, during which no radiation is generated, the trailing edge of one pulse may coincide temporally with the leading edge of the following pulse, or the pulses may overlap such that radiation of two or more wavelengths (or spectral bands of wavelengths) may be generated simultaneously.

The EMR is preferably generated by light-emitting diodes (LEDs) that are arranged in serial "strings" connected to a common power supply. Each LED string may comprise LEDs designed to generate radiation of a single wavelength or band of wavelengths. The LEDs may be embedded in a flexible pad that designed to fit snuggly against a skin surface of a human body, allowing the target tissue or organ to be exposed to a uniform pattern of radiation.

Each of the LED strings is controlled by a channel driver, which in turn is controlled by a microcontroller. The microcontroller includes a "pattern library" of algorithms each of which defines a particular process sequence of pulses of the EMR generated by the LED strings. Using a display, keyboard or other input device, a doctor or clinician can select the particular algorithm (process sequence) that is suited to the condition or disease being treated.

BRIEF DESCRIPTION OF THE DRAWINGS

FIG. 5A is a cross sectional view of a white LED backlight used in LED HDTVs as seen by the human eye.

FIG. 8D is a chart showing the hierarchical impact of animal photobiomodulation in Homo Sapiens.

DESCRIPTION OF THE INVENTION

Principles of Photobiomodulation

Photobiomodulation involves the controlled delivery of photons into living cells and tissue stimulating a biochemical response. When applied to medical science, the use of photobiomodulation to produce a beneficial or therapeutic result is herein referred to as "phototherapy". A number of variables can affect photobiomodulation, including the organism, tissue, cell, or organelle being illuminated; the wavelength(s) of the light used, the absorption depth and scattering properties of the light at the impinging wavelength in the targeted and intervening tissue; the power, timing, duration, and frequency of the photoexcitation, including the potential sequencing of multiple wavelengths, the specific biochemical reaction being affected, and in therapeutic cases the nature of the injury or condition requiring treatment.

Figure 8A:
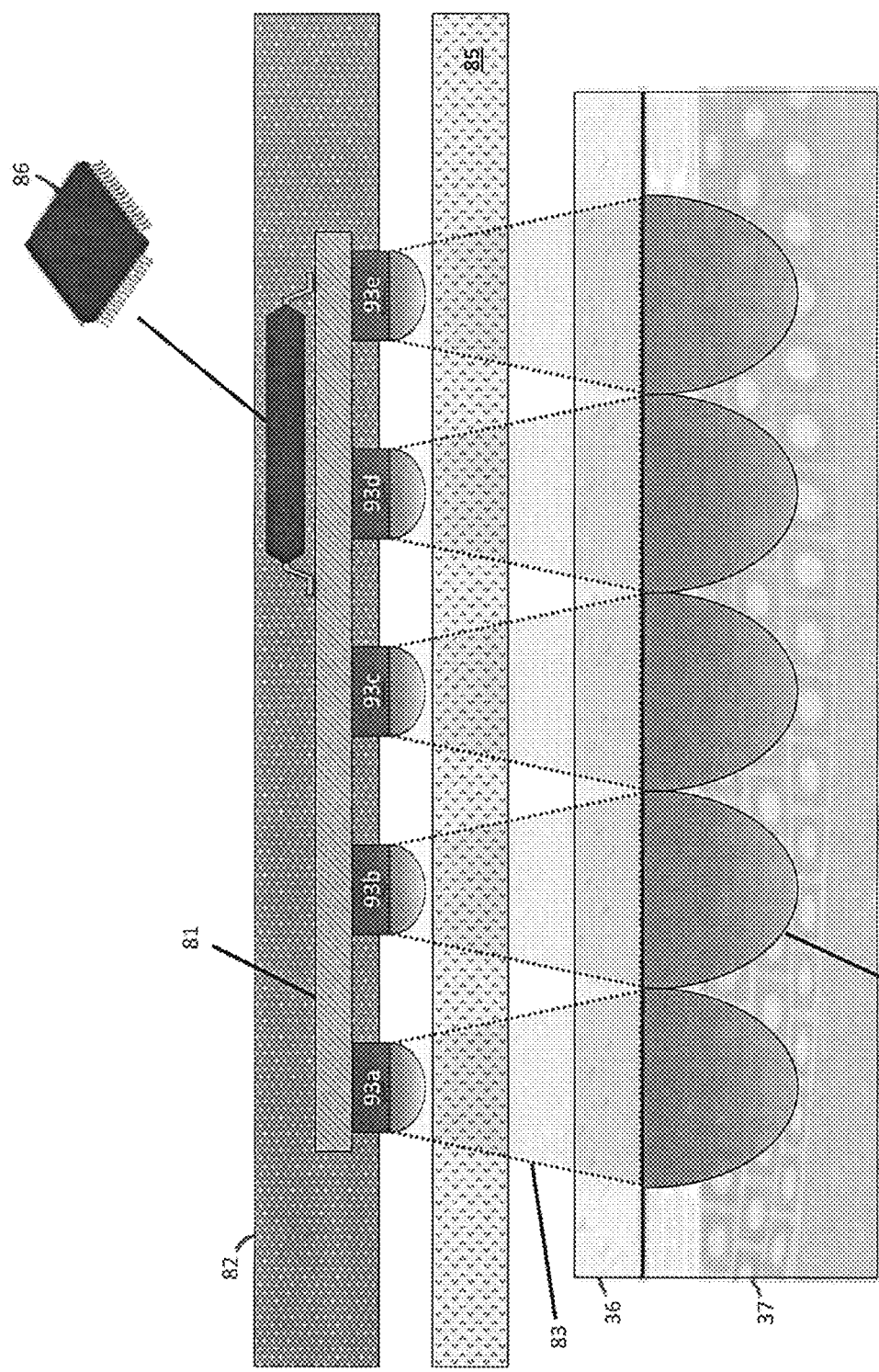
FIG. 8A is a schematic illustration of an LED pad illuminating epithelial tissue.

FIG. 8A schematically illustrates in cross section, the elements of a phototherapy delivery system, including a flexible circuit board 81, an LED array 93a through 93e, a flexible, biologically inert encapsulant 82, a flexible aseptic hygienic barrier 85, and an LED driver IC 86. The LED array 93a through 93e and its enclosure, collectively herein as an LED "pad", ideally should be sufficiently flexible and bendable to fit snugly against a patient without damaging the interconnecting conductors or electronic components within the pad. Light 83 then illuminates epithelial and epidermal tissue layers 36 and 37 accordingly, as shown by illumination and absorption profile 84. In the LED pad as shown, encapsulant 82 may cover the lenses of LEDs 93a through 93e provided it is sufficiently thin and transparent at the LED wavelength not to block the LEDs' light output.

Note: As used herein, the terms "LED driver IC" and "LED driver" are used interchangeably to refer to an IC that contains circuitry for controlling multiple channels, each channel being represented by an LED string. The term "channel driver" is used to refer to the circuit within an LED driver IC that is used to control a single LED string (channel).

Figure 8B:
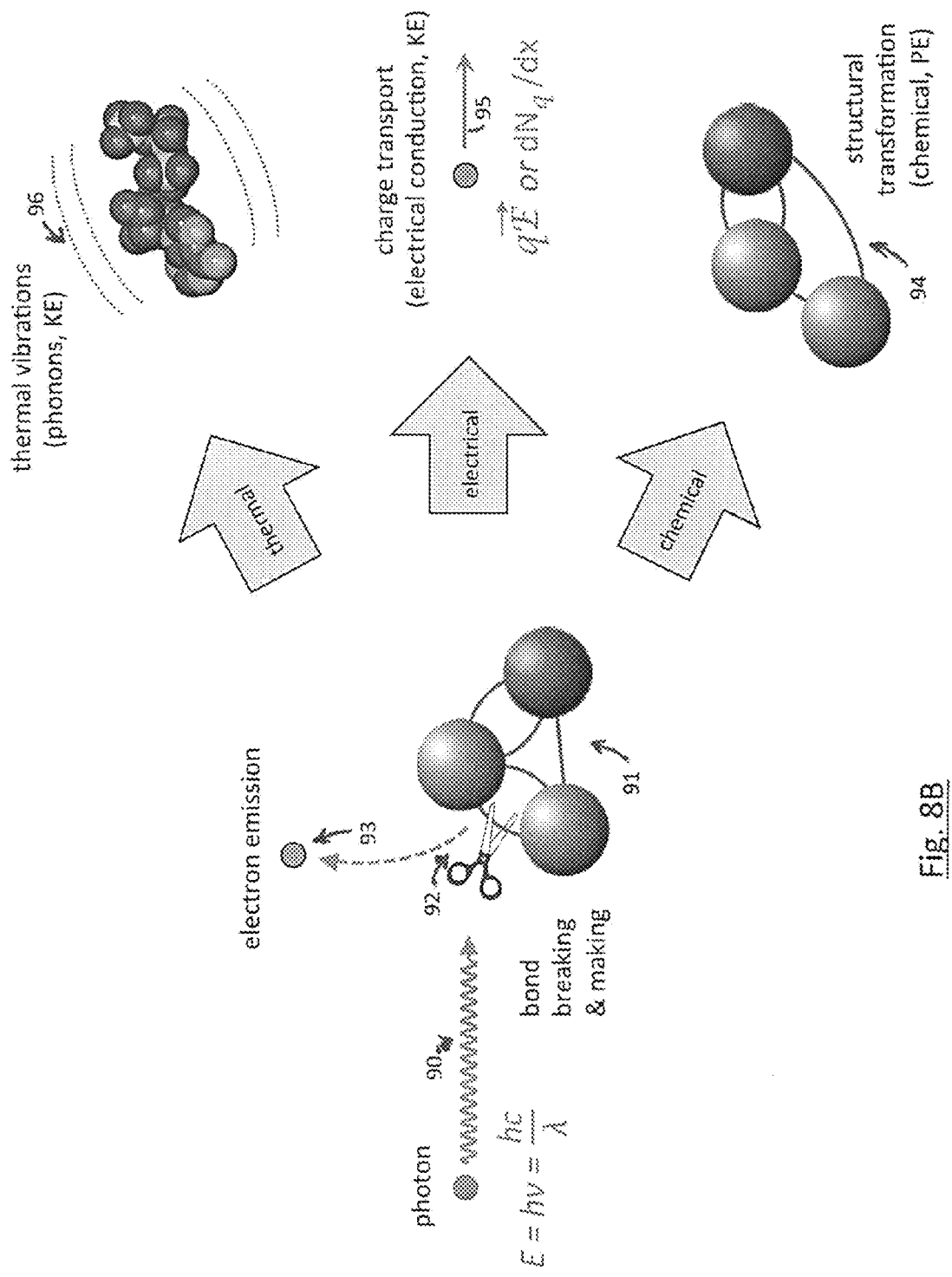
FIG. 8B is a graphical depiction of the physical mechanisms of photobiomodulation.

Photobiomodulation starts with photoexcitation of atoms and molecules, represented pictorially in FIG. 8B where an impinging photon 90 having a wavelength λ and a corresponding EMR frequency ν (denoted by the Greek letter ν, or "nu") strikes a molecule 91, breaking chemical bonds 92 and making new bonds, and potentially ejecting charges 93. The absorbed energy 90 may be divided into any combination of changes in the kinetic energy (KE) and potential energy (PE) in the system including structural transformations of molecules into higher or lower energetic states 94, charge transport 95 either by drift conduction qE in a local electric field or diffusion conduction dNq/dx due to concentration gradients, and/or by thermal vibrations 96 of molecules from heating or in quantum dynamical terms by phonons. These photon-induced or "photo-excited" reactions can happen involving any number of molecules within the cell.

Figure 8C:
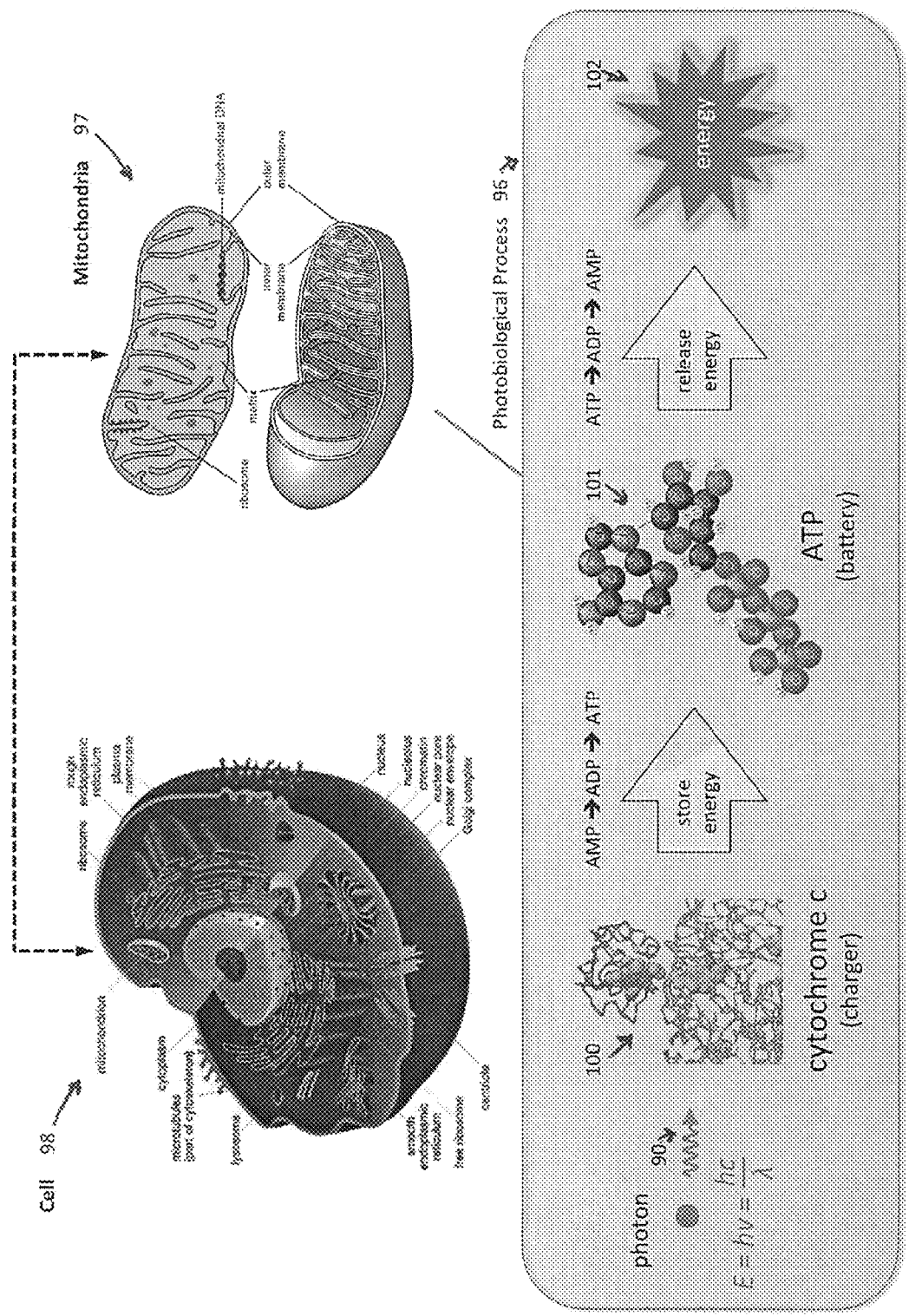
FIG. 8C depicts photosynthesis (ATP generation) in animal cells.

Some of the reactions may involve purely inorganic components while others involve organic molecules, or both. As represented in FIG. 8C, at least one confirmed photobiological process 96, the impinging photons 90 are absorbed by cytochrome-c oxidase (CCO) 100 which functions within mitochondria 97 as a battery charger, pumping adenosine monophosphate (AMP) into a higher energy state adenosine diphosphate (ADP), and ultimately pumping ADP to the highest energy state molecule adenosine diphosphate or ATP 101. For its ability to store energy, CCO 100 is sometimes referred to as a proton pump. Alternatively, if we consider ATP 101 as a battery at a cellular level, then CCO 100 could be considered the battery charger. Conversely, when ATP 101 breaks down into ADP or AMP it releases significant energy 102, over 6 k-calorie per mole.

As an organelle in an animal cell 98, mitochondria 97 provides energy in a symbiotic relationship, where cell 98 provides a beneficially protective environment for mitochondria 97. Using CCO 100, mitochondria 97 can convert sugars, the byproduct of digestion, into energy or through photobiological process 96, it can absorb light to generate ATP 101.

The energy generation resulting from photobiomodulation of mitochondria results in a cascade of biochemical, electrical and thermal effects affecting an organism at every level, from the organelle and cell, to tissue, organs and the entire organism (including homo sapiens). Reported effects are tabulated in FIG. 8D including exemplary illustrations 103 of the affected cell, tissue, organ or systems along with specific descriptions of observed photobiological responses 104. In particular note that the activation of ATP leads to enzymatic activity, the creation of intercellular catalysts and the onset and acceleration of DNA transcription, RNA translation and protein synthesis, i.e. photosynthesis in animals. One byproduct, nitric oxide (NO), is found to be key in promoting tissue repair and granulation, forming new capillaries and dilating arteries to increase blood flow and cellular oxygenation, while repairing nerves, blocking pain, and modulating immune response to suppress infection and inflammation. While these mechanisms are beyond the full scope of this disclosure, the referenced articles may provide added insight into these biochemical and cytological mechanisms.

Another important consideration in photobiomodulation is that of photoexcitation frequency. Not to be confused with the wavelength of the light $\lambda$ and its corresponding electromagnetic frequency $v_{EM}$, the photoexcitation frequency $f_{synth}$ describes the repeated period whereby a bio-organism exposed to EMR shows the ability to cyclically absorb greater amounts of energy than at other frequencies. In physics, these resonant frequencies are a naturally occurring property of matter absorbing and releasing energy in periodic fashion. Such resonant frequencies are typically orders of magnitude orders of magnitude slower than the oscillating frequency of the infrared and visible light itself, corresponding to atomic level transitions—transitions occurring at frequencies and having corresponding energy levels similar to the wavelengths of light that an atom absorbs or emits.

Since biochemical molecules, organelles, cells, tissues, organs and organisms all have mass and are held together by chemical and mechanical forces, then all these forms of biological matter must necessarily exhibit vibrational movement and resonance, each with its own characteristic frequency. Primarily because of the masses involved, organs and tissues resonate at much lower frequencies than the vibration of molecules and of atoms within a molecule.

In animals, the operation of numerous organs such as the heart, muscles, the nervous system and the brain also operate involving electrical or electrochemical processes. These electrical signals also operate at certain specific frequencies and also can exhibit resonance, primarily involving electrochemical oscillations rather than thermal vibrations. In the 1960s Nogier et al. first discussed the influence of period electrical signals stimulating human tissue with micro-currents. Later the USSR was also to conduct experiments using ceramic lamps to induce photoexcitation at controlled frequencies, but the work remained largely unpublished.

While the dynamics are still poorly understood, clearly any device intended to stimulate photobiomodulation should be capable of controlling not only the brightness and wavelength of light, but also the frequency of any periodically repeating pattern of photoexcitation.

Impact of Spectral Bandwidth on Photobiomodulation

Herein, the electronic control of photons for the purpose of photobiomodulation is referred to as "biophotonics". To design and construct a biophotonic apparatus to perform phototherapy with maximum efficacy, it is important to examine the physical mechanisms of photoexcitation consistent with the limited empirical evidence existing today.

The band theory of solids normally used to model the behavior of solid state electronics and semiconductor devices, once adapted for molecules and molecular bonds, can provide additional insight to the mechanisms occurring during photoexcitation of living cells, organelles, and the molecules contained within. A similar method was employed insightfully by Linus Pauling in his landmark book "The Nature of the Chemical Bond," [Cornell University Press, Ithaca, N.Y., 1939, $3^{rd}$ edition 1960] and is still used today in biochemistry and in the study and development of organic semiconductors. While the topics discussed in this disclosure are not specifically related to the molecules considered in the cited textbook, a similar methodology of analysis using energy bands and electron orbitals is insightful in explaining observed results and in optimizing phototherapeutic strategies.

Figure 9A:
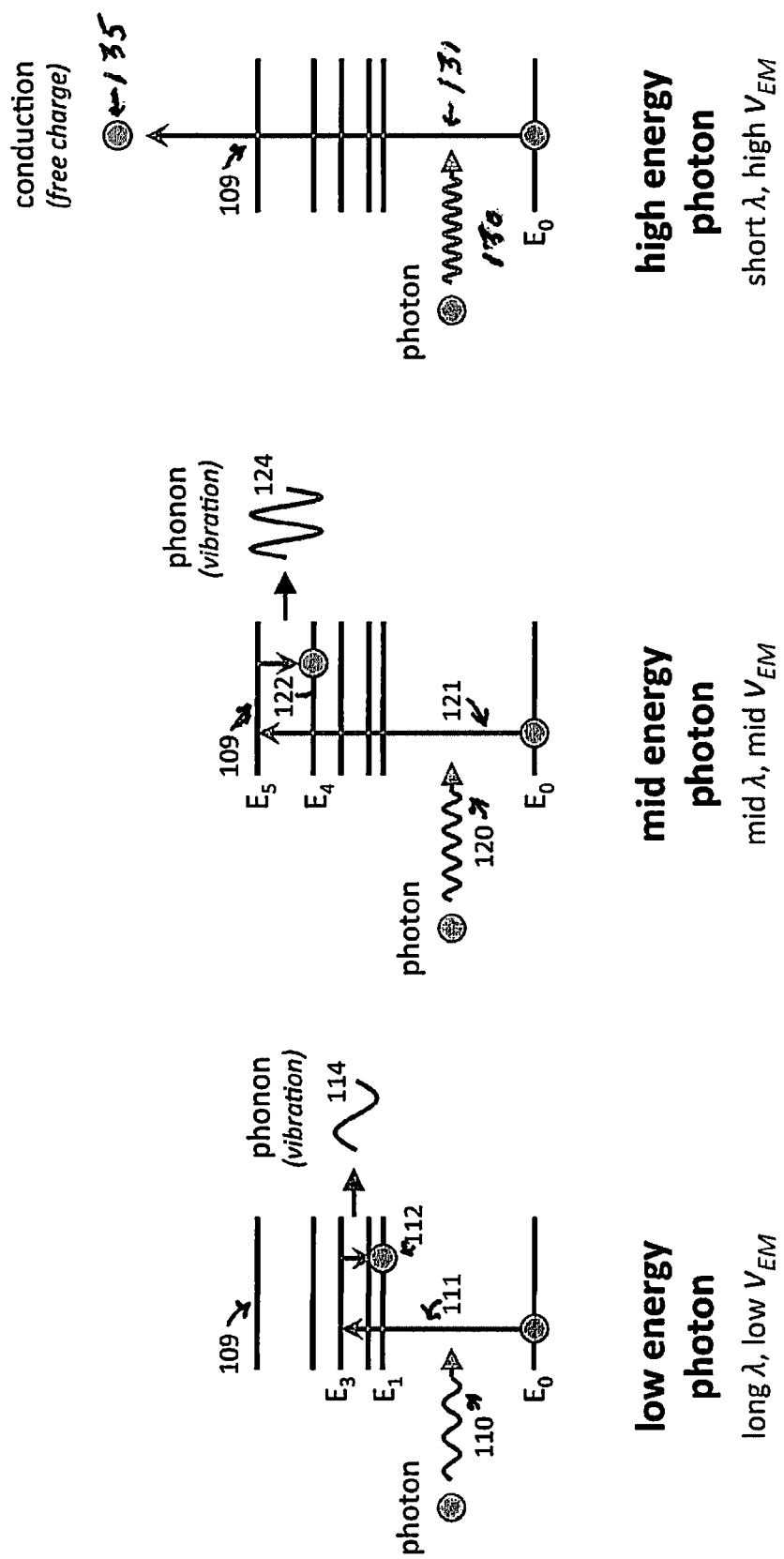
FIG. 9A is an energy band schematic representation of photoexcitation of molecules.

FIG. 9A illustrates three possible interactions of EMR with matter. In the graphics, the rectangular lines or energy bands 109 represent various potential energy states of a molecule in various forms with $E_0$ being the ground or lowest energy state, $E_1$ at a higher energy state, $E_3$ at even a higher energy, and so on. In an individual atom, these bands represent discrete energy levels and the dot represents charge present at that energy level similar to that proposed by Niels Bohr in at the beginning of the $20^{th}$ century (the so-called Bohr atom). The band theory was later adapted to groups of interacting atoms in a crystal, replacing discrete energy level with bands of allowed energy states separated by energy gaps $E_g$ where no stable quantum energy level is present. When matter absorbs light of sufficient energy to overcome these energy band gaps, charges experience a corresponding energy transition from a ground state to an elevated energy state or band.

For example in the leftmost graphic, when a photon hits the material represented by bands 109, a charge at the ground state $E_0$ jumps 111 to an excited state $E_3$. To manifest this transition, the impinging photon must carry energy greater than the bandgap or the quantum transition 111 will not occur. The energy E carried by the photon, as described by A. Einstein, is proportional to its frequency, as given by the well known relation $E=hv=hc/\lambda$ with $v=v_{EM}$ being the frequency of the EMR, $\lambda$ its wavelength, h being Planck's constant, and c being the speed of light. Provided that the photon energy E exceeds the minimum energy needed to effect a change in the potential energy of the molecule, shown mathematically as $E>Eg$, then transition 111 will occur. After the charge jumps up to the $E_3$ state, it falls back to a lower energy state $E_1$. Since this smaller transition does not involve significant energy, a phonon 114 (a quantum of vibrational energy) is released, contributing to molecular vibration and heating.

If instead of interpreting this diagram as energy bands in a crystal, we now consider the energy bands as representing energetic states of one or more interacting molecules, the process of energy absorption and energy re-release can be understood in a similar, albeit metaphoric, manner. Referring again to FIG. 9A, the left graphic involving a lower energy photon excites the molecule into state 112, one of the lower allowed energetic states and results in phonon 114. The middle graphic represents a case where the impinging photon 120 has a higher energy than photon 110, and results in photoexciting the molecule 121 to state $E_S$ only to collapse back to stable state 122 and release a phonon 124 in the process.

In the rightmost graphic, an even higher energy photon 130, having a higher frequency $v_{EM}$ and shorter wavelength $\lambda$ than photon 110 or photon 120, imparts so much an energy 131 that it breaks the molecule apart releasing a free charge 135, which is able to conduct freely within a cell or to engage in intercellular charge transport.

Figure 9B:
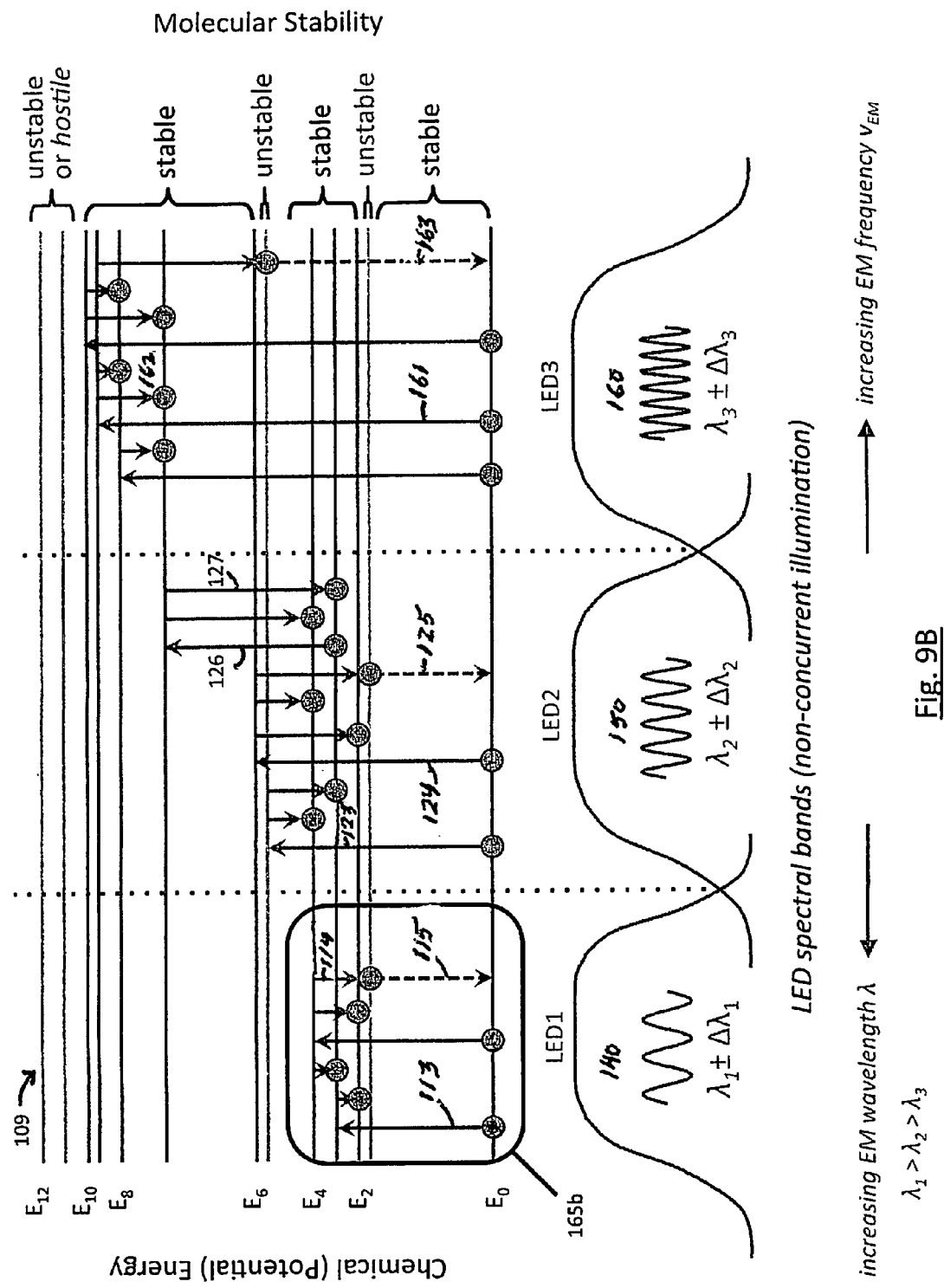
FIG. 9B is an energy band schematic representation of photobiomodulation for various light wavelengths.

FIG. 9B expands the described phenomenological energy band analysis to a collection of molecules and their interaction with photons having not a single wavelength but representing a spectral band of frequencies and wavelengths. In the graph, the vertical axis represents the chemical potential energy (PE) of the molecules represented by energy bands 109, which have a variety of energetic states $E_0$ to $E_{12}$. The horizontal axis describes the relative frequency (and wavelength) of impinging photons, with the left side of the graph representing lower EMR frequencies $v_{EM}$ (and hence increasing EMR wavelengths $\lambda$) and the right side representing higher EMR frequencies $v_{EM}$ (decreasing EMR wavelengths $\lambda$). The transitions represent the many and varied interactions of molecules with different wavelength photons.

As shown, photons emitted from an array of light emitting diodes LED1 do not comprise a single wavelength but a spectral band of frequencies and wavelengths 140 having a nominal value $\lambda_1$ and varying above and below by some amount $\pm\Delta\lambda_1$, i.e. comprising a spectral band $\lambda_1 \pm \Delta\lambda_1$. Since $E = hv_{EM} = hc/\lambda$, then spectral band 140 not only represents a range in frequencies and wavelengths but in corresponding photon energies. Similarly, the light emitted from arrays of light emitting diodes LED2 and LED3 do not comprise single wavelengths, but spectral band 150 with wavelengths $\lambda_2 \pm \Delta\lambda_2$ and spectral band 160 with wavelengths $\lambda_3 \pm \Delta\lambda_3$ respectively, where $\lambda_1 > \lambda_2 > \lambda_3$. For example, an array of light emitting diodes LED1 may constitute a center wavelength $\lambda_1 = 875$ nm and a spectral bandwidth varying from 860 nm to 890 nm, so that $\lambda_1 \pm \Delta\lambda_1 = 875$ nm±15 nm in the infrared band. Similarly an array of light emitting diodes LED2 may comprise a spectrum $\lambda_2 \pm \Delta\lambda_2 = 740$ nm±15 nm in the near infrared band, and LED3 may comprise $\lambda_3 \pm \Delta\lambda_3 = 670$ nm±15 nm in the long wavelength portion of the visible red spectrum.

The spread $\Delta\lambda$ in the spectrum of an array of LEDs results from two stochastic, i.e. random, physical mechanisms. First, in the manufacture of LEDs, the consistency of the bandgap for bandgap engineered materials and the presence of defects, dislocations and unintended impurities affects the light wavelengths emanated from each individual LED. Second, the center values of all the LEDs in the array collectively exhibit a statistical distribution even if each LED only emitted a single wavelength of light. Since these two random effects have physically independent origins, then the statistical standard deviation $\sigma_\lambda$ adds in quadrature, i.e. where $\sigma_\lambda = \text{SQRT}[\sigma_1^2 + \sigma_2^2]$ and where $\sigma_1$ and $\sigma_2$ represent the standard deviation within an individual LED and in a collection of LEDs. The total spectral width $\pm\Delta\lambda$ of an array of LEDs can be statistically approximated by the three-sigma distribution, so that $\pm\Delta\lambda = \pm 3\sigma_\lambda$.

Photoexciting the molecules having energy bands 109 exclusively with wavelengths 140 from an array of light emitting diodes LED1 results in a collection of energy transitions 165b including exemplary transitions 113, 114, and 115. Note that not every energy state is stable. For example, energy state $E_1$ may under certain ambient conditions of temperature, humidity, pH, etc. be unstable. Exciting the molecule into that state immediately or after some duration of time results in the molecule collapsing back (arrow 115) to its ground state $E_0$. Two important observations can be made from this analysis: first, that the spectral band emanating from an array of LEDs invokes not one, but a number of molecular reactions and energy transitions; and second, that with its long wavelengths, array of light emitting diodes LED1 is incapable of photoexciting molecules to any potential energies above $E_4$.

In a similar manner, an array of light emitting diodes LED2 having shorter wavelengths 150 photoexcites a number of reactions including those represented by arrows 123, 124, 122, 125, 126 and 127. These reactions and state changes, while overlapping some energy transitions 165b, tend to involve higher energy levels than reactions photoexcited from an array comprising longer wavelength LED1 light emitting diodes. For example, an array of light emitting diodes LED2 invokes transitions up to energy level $E_7$ whereas an array of light emitting diodes LED1 results in transitions that never exceed energy level $E_4$. Some levels, such as $E_5$ may in fact be unstable where transitions to such states collapse back to the ground state $E_0$ for the affected molecule.

An array of light emitting diodes LED3 having the shortest wavelengths 160 and therefore the highest photon energies, invokes the highest energy transitions 161, 162, 163 up to energy level $E_{10}$, well beyond the reactions and energy transitions induced by photoexcitation from arrays of light emitting diodes LED2 or LED1. The highest energy state photoexcited from an array of light emitting diodes LED3, specifically $E_{10}$, is below energy levels $E_{11}$ or $E_{12}$ triggering hostile or severe molecular instability.

Figure 9C:
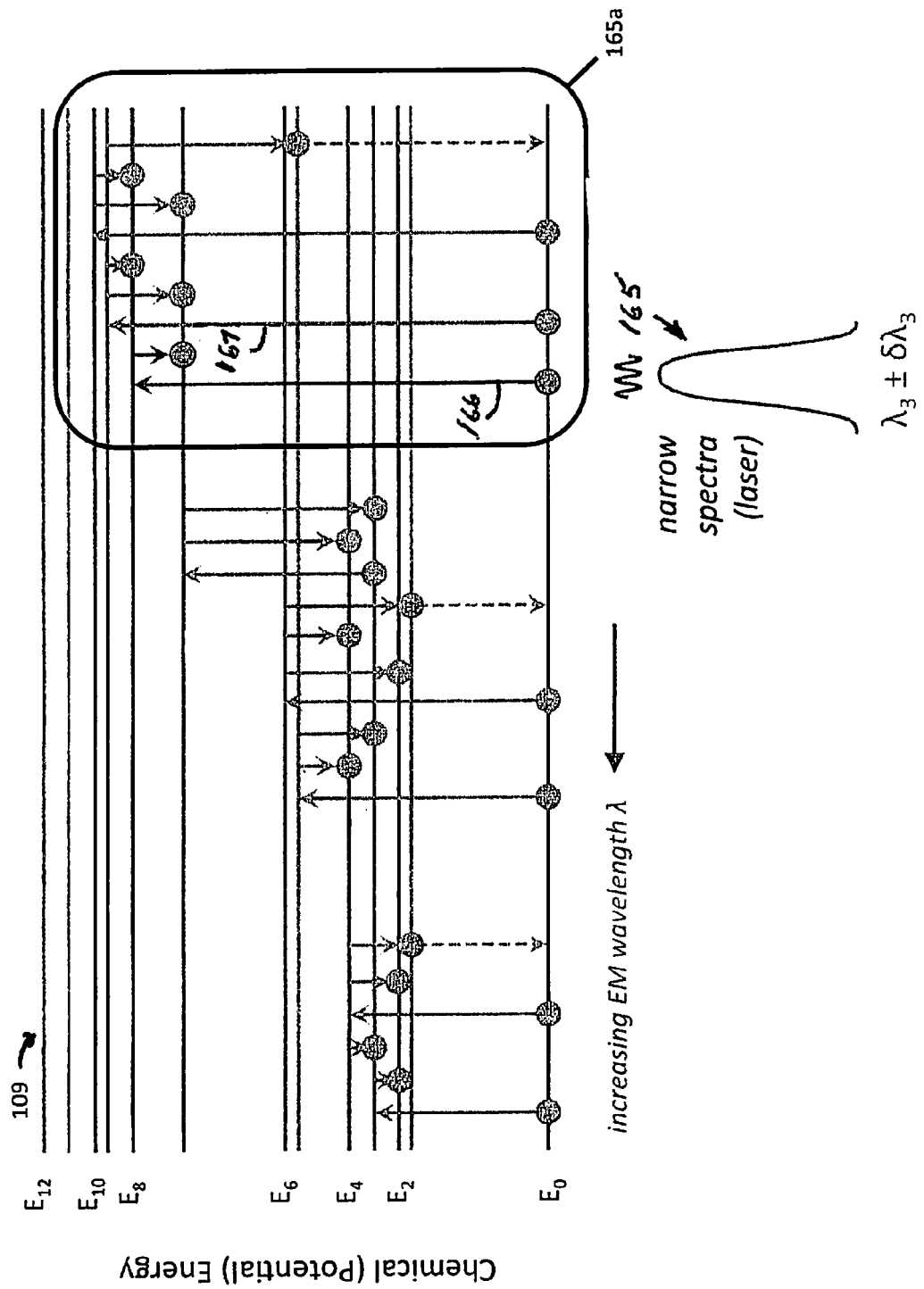
FIG. 9C is a schematic representation of narrow band photobiomodulation

FIG. 9C illustrates the impact of very narrow bandwidth photoexcitation 165. In this case the impinging EMR has a very bandwidth $\lambda_3 \pm \delta\lambda_3$ where $\delta\lambda_3$ is roughly an order of magnitude narrower than $\Delta\lambda_3$, i.e. where $\delta\lambda_3 \ll \Delta\lambda_3$. For example, instead of $\lambda_3 \pm \Delta\lambda_3 = 670$ nm±15 nm, an example of a narrow bandwidth illumination is $\lambda_3 \pm \delta\lambda_3 = 670$ nm±1.5 nm. Such narrow bandwidth is typically emanated from lasers and not from LEDs. Even though the center wavelength is the same value $\lambda_3$ as an array of light emitting diodes LED3, the resulting reactions and transitions 165a using a narrow bandwidth laser are dramatically fewer than the reactions and transitions resulting from using array of light emitting diodes LED3. Too few reactions, shown here only to comprise transitions 166 and 167, can negatively impact the magnitude of photobiomodulation, reactions that rely on a plethora of catalytic and biochemical interactions. In phototherapy, treatments involving narrow bandwidth EMR invoke minimal photobiomodulation suffering reduced therapeutic benefit compared to that of broader spectrum LEDs.

Although narrow spectrum photoexcitation exhibits lower efficacies in stimulating cell repair than broader spectra, such protocols hold promise in targeting and destroying specific unwanted cells, organisms, or pathogens infecting a host. Selective targeting for cellular destruction rather than cell and tissue repair is a subject beyond the scope of this disclosure.

Figure 9D:
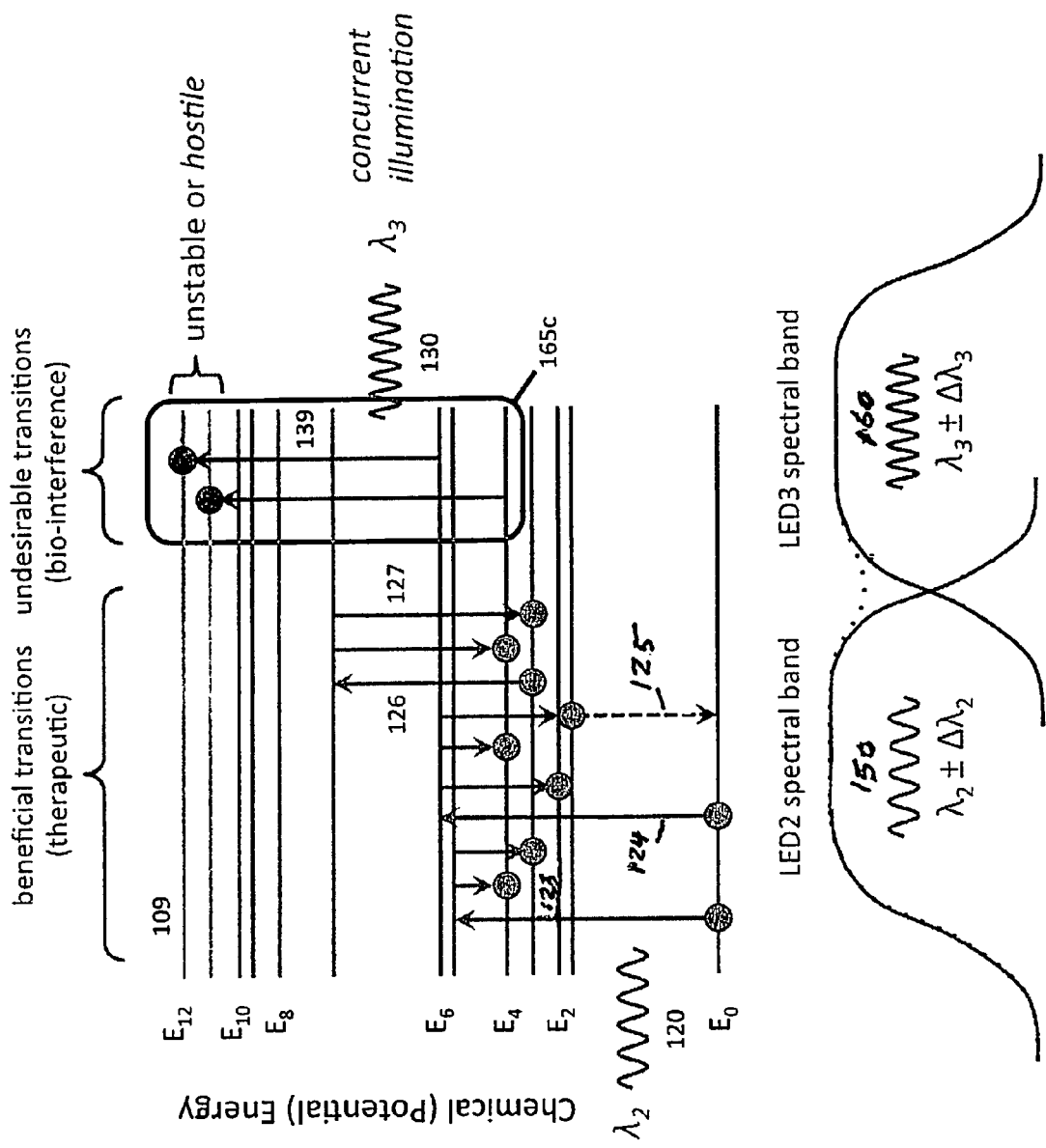
FIG. 9D is an energy band schematic representation of bio-interference in broadband photobiomodulation.

While overly narrow bandwidth photoexcitation may be ineffective in stimulating therapeutic benefits, overly broad bandwidth photoexcitation may also be ineffective and even detrimental. FIG. 9D illustrates one mechanism by which simultaneous photoexcitation by arrays having two bandwidths of light emitting diodes may produce undesirable results. As described previously, a collection of molecules with energy hands 109 photoexcited by an array of light emitting diodes LED2 with a spectral band 150 and wavelengths $\lambda_2 \pm \Delta\lambda_2$ stimulates a variety of transitions 123, 124, 125, 126, 127 and others, herein collectively described as "beneficial" or therapeutic transitions. If however simultaneous to the array of light emitting diodes LED2 being illuminated, the same molecules are photoexcited by array of light emitting diodes LED3 having its spectral band 160 and wavelengths $\lambda_3 \pm \Delta\lambda_3$ the result may include transitions not present when light emitting diodes arrays LED2 or LED3 are used independently and not concurrently.

These unexpected and undesirable transitions 165c occurring from the concurrent illumination and photoexcitation from both LED2 and LED3 arrays of light emitting diodes include stimulating transitions to unstable and even hostile states as exemplified by transition 139. The formation of hostile energy states $E_{11}$ and $E_{12}$, in turn may depending on ambient conditions lead to the impairment or destruction of biochemically beneficial molecules. Mechanisms leading to undesirable transitions 165c include optical wave interference producing spatially dependent crests and valleys in the energy distribution in cells and tissue, two step transitions where spectral band 150 photoexcites a molecule to energy band $E_4$ or $E_6$ and spectral band 160 further photoexcites the molecules to hostile energy bands $E_{11}$ and $E_{12}$, catalytic effects making energetically unfavorable reactions more likely, etc.

The term "hostile" state is not meant to imply the resulting molecule is toxic, mutagenic or carcinogenic to the cell, but that the transition counters the formation or activation of beneficial molecules that would otherwise be formed by photobiomodulation stimulated from the phototherapy treatment. The result is primarily a reduction in benefit from the photoexcitation manifested therapeutically as diminished efficacy. This diminished efficacy is herein referred to as molecular "bio-interference". Mechanistically, bio-interference from undesirable transitions 165c represents the breaking apart or biochemical deactivation of beneficial molecules, the impairment of the formation of beneficial molecules, the formation of catalysts that impair the formation or activity of beneficial molecules, the formation of molecules that change the surrounding pH adversely affecting chemical reactivity of beneficial molecules, and any mechanism diverting impinging energy otherwise involved in the formation of beneficial molecules.

One possible scenario where the concurrent application of arrays of differing wavelength LEDs will likely avoid significant bio-interference is in spectral "blending". In spectral blending, arrays of light emitting diodes comprising two LED types and having different spectral bands are concurrently illuminated but where one LED array is dimmed to a power level (brightness) that is small fraction of the other. For example if an array of LEDs comprising LED2 having a spectral band $\lambda_2 \pm \Delta\lambda_2$ is powered at full brightness (at a duty factor $D_2 = 100\%$) and a second array of LEDs comprising LED3 having a spectral band $\lambda_3 \pm \Delta\lambda_3$ is powered to a brightness one tenth that of the LED2 array (i.e. where duty factor $D_3 = 10\%$), the statistical likelihood of significant bio-interference is minimal because only a small fraction of photons are even capable of invoking undesirable transitions. No evidence exists today that blending offers any photobiomodulation benefit, but conceivably a low population of "hostile" catalysts may in limited concentrations offer benefits in suppressing the formation of other even more hostile molecules. An analogous example in nature is that organisms exposed to normal ambient levels of ionizing radiation are often more robust than those completely insulated from all ionizing radiation, in part because the radiation suppresses foreign invaders and kills weaker cells so a stronger cell population can flourish.

Figure 9E:
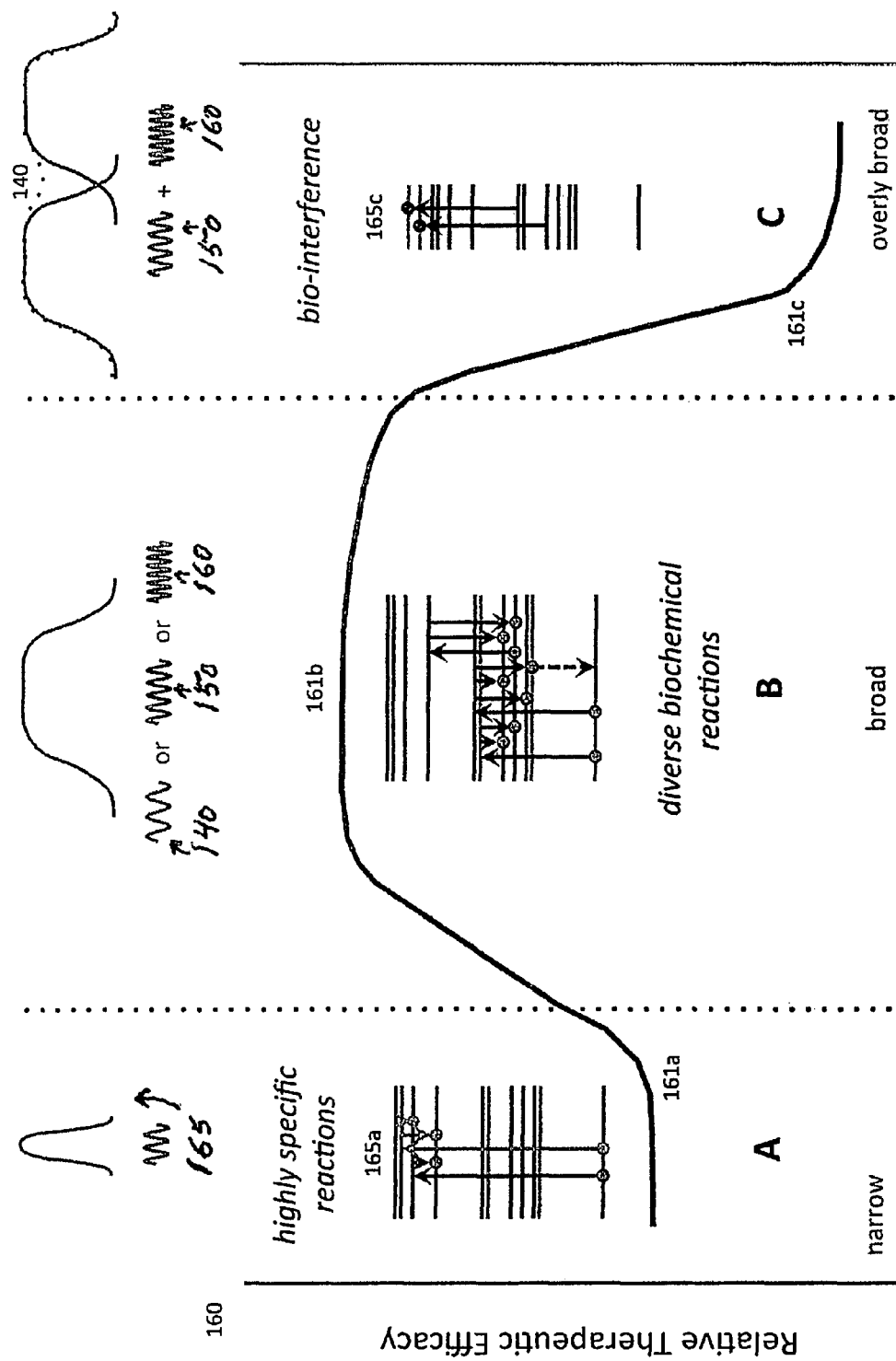
FIG. 9E is an energy band description of observed relative therapeutic efficacy as a function of spectral bandwidth.

Considering all the aforementioned mechanisms, the behavior and importance of spectral bandwidth on photobiomodulation and its impact on the therapeutic efficacy of photoexcitation is summarized in FIG. 9E comprising a graph with an abscissa measuring the relative spectral bandwidth ($\lambda_{max} - \lambda_{min}$) and the ordinate representing the relative therapeutic efficacy, i.e. a measure of the degree of beneficial photobiomodulation. The graph is predicated on the assumption that the impinging frequencies can be absorbed by the targeted cells and the EMR is not blocked or absorbed by any intervening tissue present between the targeted cells and the light source.

That caveat aside, region B illustrates illumination of tissue using relatively broad spectral bandwidth EMR, e.g. in the range of tens of nanometers, where photoexcitation results in diverse biochemical reactions and high therapeutic efficacy 161b. Such a condition may be achieved independently using arrays of light emitting diodes LED1, LED2 or LED3 with corresponding spectral bands 140, 150 or 160, respectively, by not concurrently in combination. Region C representing illumination from broad spectral bandwidth EMR, e.g. an order of magnitude broader than region B, exhibits a diminished therapeutic efficacy 161c due to bio-interference resulting from overly broad spectra photoexcitation. Such a condition can arise from concurrent illumination from arrays of LED2 and LED3, i.e. the simultaneous presence of spectral bands 150 and 160, or from wide spectrum light from heat lamps, sun lamps, and unfiltered sunlight.

Region A illustrates illumination of tissue using very narrow spectral bandwidth EMR, e.g. in the range of a few nanometers or less, produces few and highly specific biochemical reactions too limited to invoke substantial photobiomodulation or significant therapeutic results. Such a condition is typical to illumination by laser light—EMR by its very nature tuned to a narrow bandwidth. Because of the highly specific reactions, it relative therapeutic efficacy 161a in stimulating cellular repair is therefore diminished but may still be better than using overly broad spectral bandwidth light. Pragmatically speaking, laser light also suffers from a small spot size compared to the area illuminated by LEDs. That said, narrow bandwidth photoexcitation, albeit at higher power levels, may be used to invoke targeted destruction of cells, organelles or biochemical molecules.

While the phenomenological description of the impact of spectral bandwidth on photobiomodulation described herein is extrapolated from the band theory of solids, the resulting curve of therapeutic efficacy versus spectral bandwidth is consistent with our own empirical data, measurement, and observation. The result is also consistent with the early studies performed by NASA where sunlight and broad spectrum light from incandescent lamps were found to be less efficient at stimulating healing than narrow spectrum light from infrared lasers.

While phototherapy efficacy today is measured by visual inspection of treated tissue and by patient interviews, in the future, at least in the infrared spectrum, it may be possible to image, i.e. "see", molecular interactions in real time during photobiomodulation, conceivably using the same infrared light being used for photoexciting the tissue or cells.

The conclusion of this section is that, in general, LEDs exhibit a spectrum of wavelengths better suited for photobiomodulation and for phototherapy than lasers, but that various spectrum LEDs, if desired, should be used sequentially rather than concurrently to avoid bio-interference adversely limiting phototherapy efficacy. Common sense also dictates that photobiomodulation of any specific organ, tissue, cell or organelle requires that any intervening tissue (e.g. blood, water, fat) does not block or absorb significant portions of the wavelength of EMR being applied, and that a combination of various wavelengths are needed for photoexcitation of different organs and tissues.

An apparatus properly designed for maximizing the efficacy of medical phototherapy must therefore deliver a plurality of light wavelengths in a variety of sequences using an array of light sources covering a relatively large area. Ideally these sequences and LED settings should be adjustable and programmable to facilitate the maximum in user flexibility, especially important in capturing and perpetuating the learning of clinicians and attending physicians. While the primary function should comprise a sequential application of differing wavelength LEDs, the apparatus should still be adaptable to include concurrent LED illumination (blending) and even laser treatments, should specific beneficial therapies later be discovered.

Dynamic LED Driver Operation

A medical phototherapy apparatus should comprise a number of elements including a flexible aseptic pad containing multiple strings of individually controlled LEDs having differing wavelengths, a controller and LED driver circuit with to flexible interface capable of programmable waveform synthesis and adjustable sequencing, a dynamic power supply, and optionally a battery power source. The variables requiring electronic control in a medical phototherapy apparatus include

- Independent control of the current in each string of LEDs
- Independent control of the brightness of each string of LEDs using PWM dimming
- Independent control of the switching frequency of each LED string
- Independent control of the phased turn-on of LED strings
- A dynamically adjusted voltage regulator maintaining requisite LED currents with minimal power loss
- Flexible sequencing of LED strings
- Detection of LED faults with a choice of response options Independent control of LED strings may be accomplished using dedicated hardware and custom integrated circuits or by using a bus-controlled driver IC interfaced to a programmable microcontroller. The advantage of the latter choice is that a microcontroller offers user flexibility in implementing specific LED control algorithms while bus-controlled LED driver ICs, originally developed, for HDTV backlighting (as described earlier in this disclosure) are now commercially available at reasonable prices. Regardless of the hardware platform, the LED drive system for medical phototherapy must support algorithmic control of waveform synthesis in order to offer physicians their choice in therapeutic strategies and protocols.

Figure 10A:
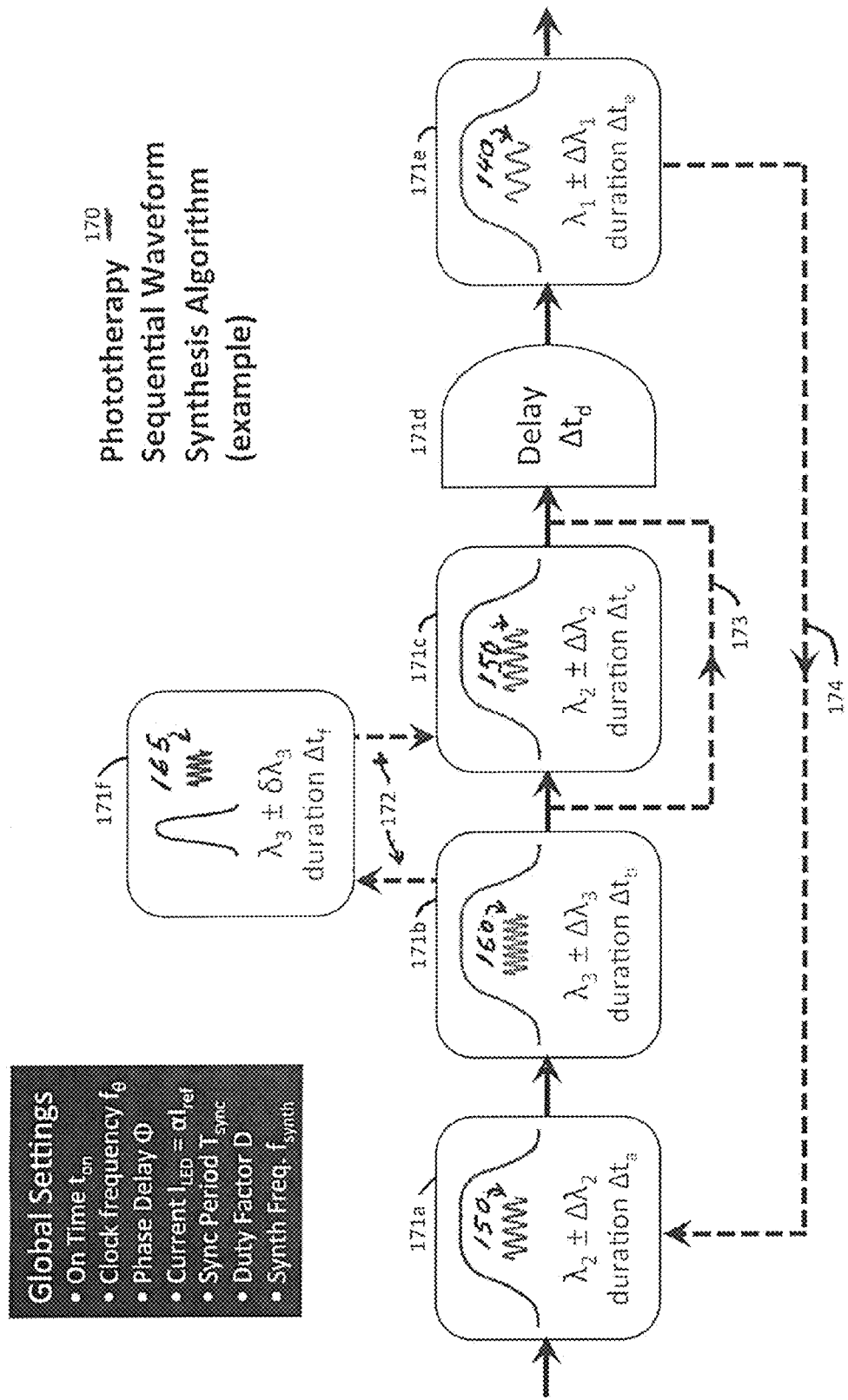
FIG. 10A is a flow chart of an exemplary dynamic phototherapy protocol comprising sequential operation of LED strings of differing wavelengths.

FIG. 10A illustrates one example of a sequential waveform synthesis algorithm for phototherapy. As shown, in algorithm 170 only one wavelength LED array is illuminated at a time consistent with the prior discussion for maximizing photobiomodulation and phototherapy efficacy. In this example, a number of operating conditions are preset to fixed conditions including the LED brightness set by duty factor D (Controlled by $t_{on}$ and $T_{sync}$), LED sequencing to minimize power supply turn-on and inrush currents set by phase delay $\varphi$, the sync and system clock frequencies set by $T_{sync}$ and $f_\theta$ respectively, and the LED current $\alpha I_{ref}$ set by $I_{LED}$. The digital representation of the variables $t_{on}$, $\varphi$, and $I_{LED}$ are stored in digital registers for each channel and dynamically programmable through a digital bus interface bus.

In the FIG. 10A example, the sequence starts with photoexcitation 171$a$ where an LED array with spectral band 150 comprising wavelengths $\lambda_2 \pm \Delta\lambda_2$ is illuminated for duration $\Delta t_a$ followed by photoexcitation 171$b$ where an LED array with spectral band 160 comprising wavelengths $\lambda_3 \pm \Delta\lambda_3$ is illuminated for duration $\Delta t_b$. In photoexcitation 171$c$ the LED array with spectral band 150 comprising wavelengths $\lambda_2 \pm \Delta\lambda_2$ is once again illuminated, this time for a duration $\Delta t_c$. After a timed delay 171$d$ of duration $\Delta t_d$, an LED array with spectral band 140 comprising wavelengths $\lambda_1 \pm \Delta\lambda_1$ is illuminated 171$e$ for duration $\Delta t_e$ as a final step in the sequential waveform synthesis algorithm 170.

As indicated by arrow 174, after the entire sequence is complete, it may be repeated any number of times as programmed. During the first sequence, or during every repetition, or during only some repetitions photoexcitation 171$c$ may be bypassed, i.e. skipped (arrow 173). Alternatively during some, all, or none of the cycles, laser photoexcitation 171$f$ with spectral narrow spectral band 165 comprising wavelengths $\lambda_3 \pm \delta\lambda_3$ is illuminated for duration $\Delta t_f$ between photoexcitations 171$b$ and 171$c$. Even with the same center wavelength $\lambda_3$, the narrow spectral band 165 (e.g. emanating from an array of lasers) represents a tighter spectral distribution than spectral band 160 produced by an array of LEDs, i.e. mathematically as $\delta\lambda_3 \ll \Delta\lambda_3$. In waveform synthesis algorithm 170, any duration $\Delta t_a$, $\Delta t_b$, $\Delta t_c$, $\Delta t_d$, $\Delta t_e$, or $\Delta t_f$ may dynamically be adjusted to any value, including zero.

Figure 10B:
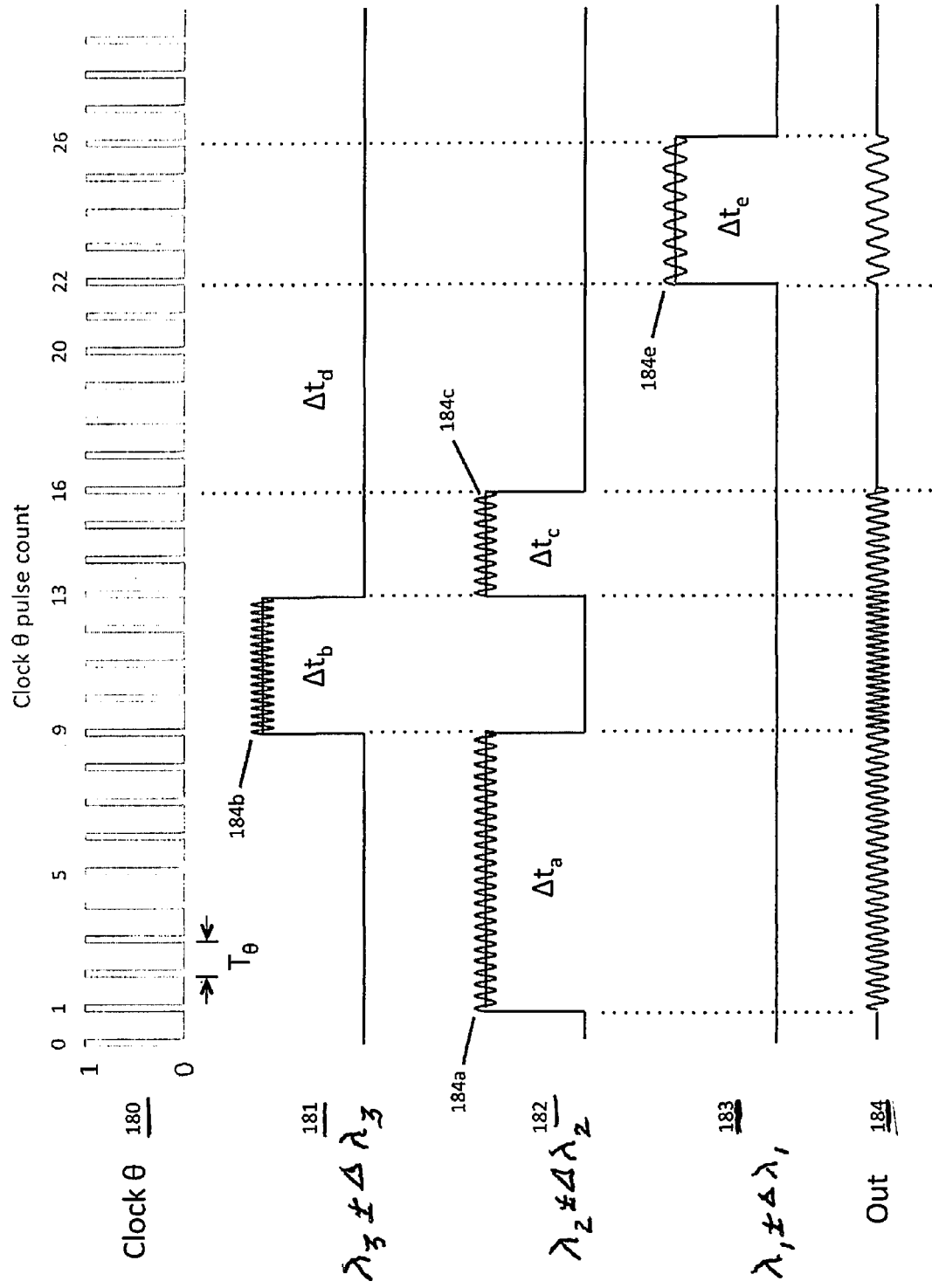
FIG. 10B is a timing diagram of the exemplary dynamic sequential phototherapy protocol shown in FIG. 10A.

FIG. 10B illustrates the output resulting from the main sequence of waveform synthesis algorithm 170 and the various elements used in its construction. Waveform synthesis, in this case square wave pulses, is performed using separate programmable counters for LED strings comprising the various wavelength LEDs, namely $\lambda_1$, $\lambda_2$, and $\lambda_3$ with each distinct digital counter counting clock pulses from Clock $\theta$. Timing diagram 180 for Clock $\theta$ illustrates a continuous string of digital clock pulses each of period $T_\theta$. While the example illustrates the time intervals $\Delta t$ lasting on a few clock pulses for simplicity's sake, in practice the $\Delta t$ intervals likely last from minutes to tens of minutes and may include a repeated pattern of waveforms synthesized with programmed controlled synthesized frequencies $f_{synth}$. The procedure for waveform synthesis is described later in this disclosure.

Clock $\theta$ may be used to generate a second slower clock known as the Sync signal (not shown) or alternatively both Clock $\theta$ and the Sync pulse may be generated from a common digital oscillator and associated timers. In an alternative embodiment, the Clock $\theta$ and the Sync pulse may be generated from different oscillators operating at different frequencies, but synchronized using phased-lock-loop (PLL) circuitry, a method well known to those skilled in the art of digital clocked logic.

The counter used for toggling LED strings having wavelength $\lambda_1$ on and off as shown in timing diagram 181, counts a series of pulses (e.g. 9 pulses as shown) lasting for a duration $\Delta t_a$ keeping the $\lambda_1$ LED strings off while the $\lambda_2$ LED strings are being illuminated. Immediately thereafter the $\lambda_2$ LED strings are turned off and $\lambda_1$ LED strings are turned on causing the LED pad to emit $\lambda_1$ EMR illustrated by sine wave 184$b$ for a duration $\Delta t_b$ (e.g. 4 pulses as shown). The $\lambda_1$ LED channels stay off for the remaining duration ($\Delta t_c + \Delta t_d + \Delta t_e$) shown.

Figure 10C:
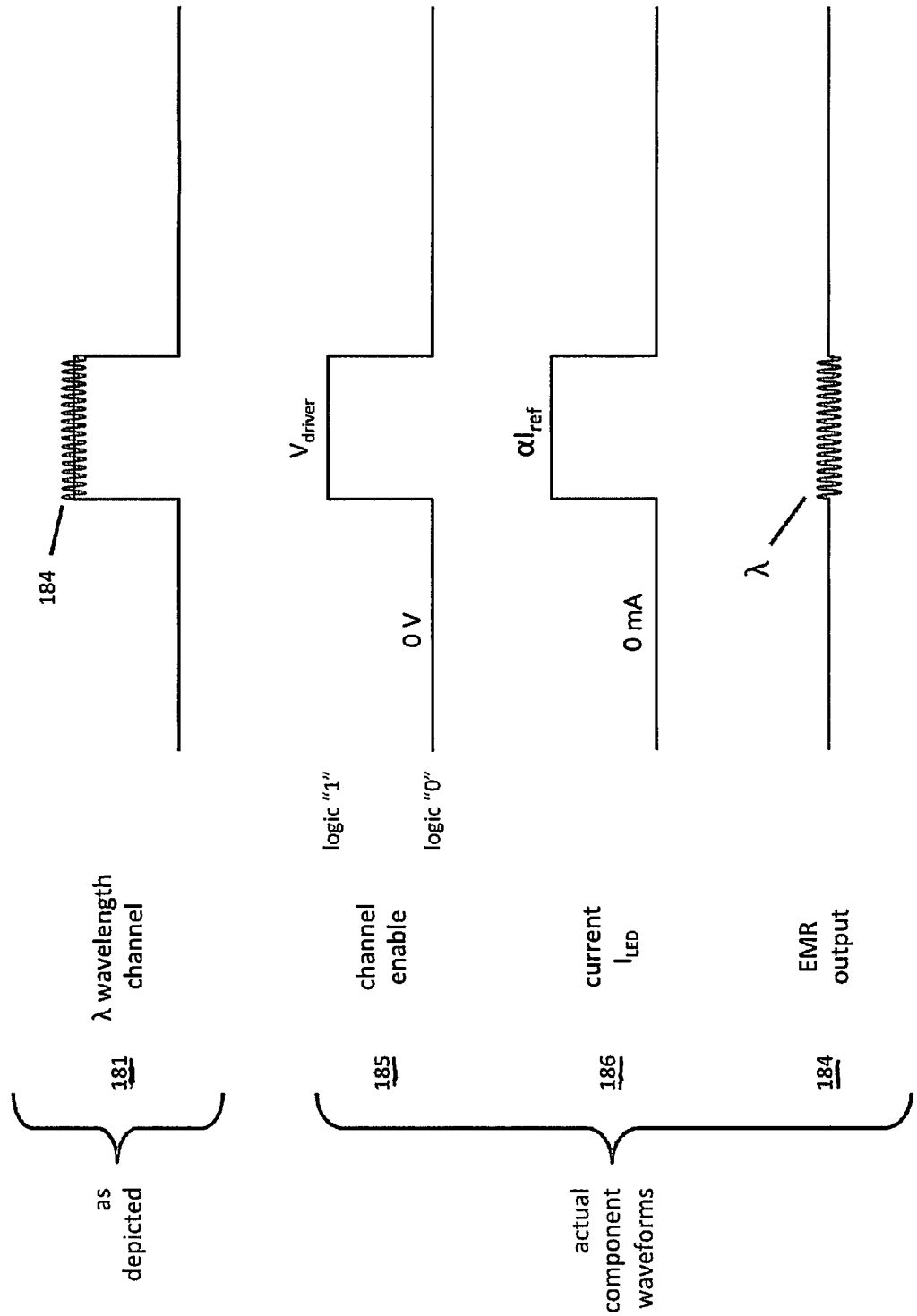
FIG. 10C is an illustration of the details of waveform representation.

For the purpose of clarification, timing diagram 181 (along with timing diagrams 182 and 183), actually depict the superposition of three separate curves. Expanding diagram 181 into its three components in FIG. 10C, waveform 185 depicts a digital "enable" signal having an off-state shown as a digital "0" or a constant voltage of 0V, and an on-state depicted by a digital "1" or a high-logic signal having voltage $V_{driver}$. Illustrated alone, the digital waveform appears as one or more square wave pulses. The same shape waveform 186 also represents the current conduction waveform in any conducting strings of LEDs, having a value of 0mA when the LED string is off and a current $\alpha I_{ref}$ when a string of LEDs is on and conducting. EMR output 184 illustrating a sine wave when the LED is on, conducting and illuminated depicts the EMR emanated from an LED of particular wavelength $\lambda$ illuminated, and a flat line showing no EMR emission when its off For convenience (and for brevity's sake), the three curves are superimposed in the waveforms shown in FIG. 10B and throughout this disclosure. It should be clarified that in the superimposed waveform representation 181, EMR output 184 represents optical power, not an electrical signal, while component waveforms for channel enable 185 and $I_{LED}$ current 186 are purely electrical signals. No sine wave (other than unintended noise) exists in these electrical waveforms.

Furthermore, there is no ambiguity between the optical and electrical signals because of their frequency ranges. An LED's EMR output has an electromagnetic frequency $\nu_{EM}$ in the range of hundreds of megahertz to hundreds of terahertz while the frequency $f_{synth}$ of the synthesized excitation patterns are typically in the audio spectrum, i.e. below 20 kHz, and theoretically cannot exceed the frequency of clock θ, which is at most in the megahertz range, five to eight orders of magnitude lower frequency than EMR 184. For completeness, it should be clear in these and subsequent waveform timing diagrams that the time scale for sine wave 184 is not the same scale as that of the much lower frequency digital waveforms.

Returning to the timing diagrams of FIG. 10B, the counter used for toggling LED strings of wavelength $\lambda_2 \pm \Delta\lambda_2$ on and off as shown in timing diagram 182, turns on after one pulse illuminating $\lambda_2 \pm \Delta\lambda_2$ LED strings and the pad. These strings remain on for duration $\Delta t_a$ while the $\Delta_2 \pm \Delta\lambda_2$ channel counter counts a series of 9 clock pulses after which the $\lambda_2 \pm \Delta\lambda_2$ LED strings are turned off resulting in EMR illustrated by sine wave 184a. Synchronous to $\lambda_2 \pm \Delta\lambda_2$ LED strings being turned off, $\lambda_3 \pm \Delta\lambda_3$ LED strings are turned-on and illuminated After a duration of $\Delta t_b$ comprising 4 clock pulses, the $\lambda_3 \pm \Delta\lambda_3$ LED strings are turned off and the $\lambda_2 \pm \Delta\lambda_2$ LED strings are turned on, causing the LED pad to again emit $\lambda_2 \pm \Delta\lambda_2$ EMR as illustrated by sine wave 184c for a duration $\Delta t_c$ (e.g. for 3 clock pulses). Thereafter, the $\lambda_2 \pm \Delta\lambda_2$ LED channels are turned off and remain off for the remaining duration ($\Delta t_d + \Delta t_e$) shown.

Meanwhile, the counter used for toggling LED strings of wavelength $\lambda_1 \pm \Delta\lambda_1$ on and off as shown in timing diagram 183 remains off for duration ($\Delta t_a + \Delta t_b + \Delta t_c + \Delta t_d$) or 22 clock pulses. Thereafter, the $\lambda_1 \pm \Delta\lambda_1$ LED strings are turned on and the LED pad to emits $\lambda_1 \pm \Delta\lambda_1$ EMR 184e for a duration $\Delta t_e$ or 4 clock pulses, after which the $\lambda_1 \pm \Delta\lambda_1$ LED strings are also turned off. Because no LED string was active during the duration $\Delta t_d$, i.e. over the interval between the 16 and 22 clock pulses, interval $\Delta t_d$ appears as a 6-pulse delay.

The timing diagrams shown illustrate a clocked logic counter based implementation of sequential waveform synthesis algorithm 170 from FIG. 10A, resulting in optical output 184 comprising the sequential illumination of the LED pad by $\lambda_2 \pm \Delta\lambda_2$ LED strings for a duration $\Delta t_a$, $\lambda_3 \pm \Delta\lambda_3$ LED strings for a duration $\Delta t_b$, by $\Delta_2 \pm \Delta\lambda_2$ LED strings again for a duration $\Delta t_c$, a delay of duration $\Delta t_d$ wherein no LEDs are illuminated, and finally by $\Delta_1 \pm \Delta\lambda_1$ LED strings for a duration $\Delta t_e$.

Figure 10D:
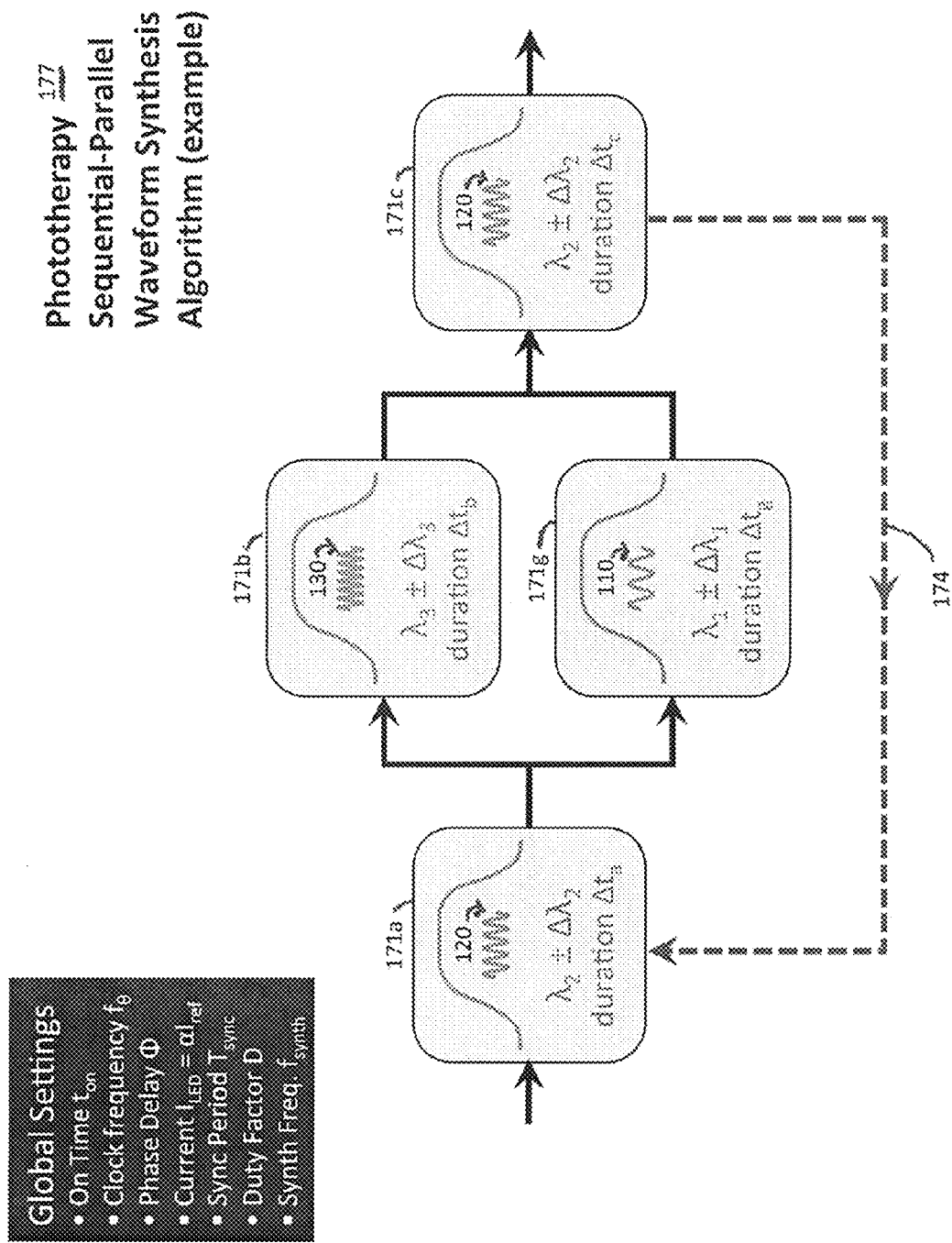
FIG. 10D is a flow chart of an exemplary dynamic phototherapy protocol combining sequential and parallel operation of LED strings of differing wavelengths.

As aforementioned, the importance of sequential operation should not preclude the possibility of mixing more than one wavelength LED concurrently. As a modification of sequential waveform synthesis algorithm 170, an example of sequential-parallel waveform synthesis algorithm 177 shown in FIG. 10D, starts with single wavelength photoexcitation 171a for duration $\Delta t_a$ comprising spectra 150 of wavelengths $\Delta_2 \pm \Delta\lambda_2$. This step is followed by the concurrent illumination of two wavelength LEDs comprising photoexcitation 171b for duration $\Delta t_b$ comprising spectra 160 of wavelengths $\lambda_3 \pm \Delta\lambda_3$ and simultaneously photoexcitation 171g for duration $\Delta t_g$ comprising spectra 140 of wavelengths $\lambda_1 \pm \Delta\lambda_1$. For the purposes of this invention disclosure, the simultaneous application of more than one wavelength of light is referred to herein as "blending". The brightness of each LED may be equal or dissimilar with one being brighter than the other, allowing a range of blends to be manifested. The duration of photoexcitation 171b and 171g need not be the same. i.e. so that $\Delta t_b \neq \Delta t_g$. In such cases, in algorithm 177 photoexcitation 171c does not commence until the longer of the two durations, either $\Delta t_b$ or $\Delta t_g$, is completed. Algorithm 177 is then completed with single wavelength photoexcitation 171c for duration $\Delta t_c$ comprising spectra 150 of wavelengths $\lambda_2 \pm \Delta\lambda_2$. As indicated by arrow 174, the sequence can then be repeated for as long as desired Waveform synthesis algorithms 170 and 177 are not meant to represent an exhaustive description of all the sequential and sequential-parallel sequences possible in phototherapy using multiple wavelength LEDs and lasers, but simply to illustrate by example a number of possible sequences and the operational elements in these sequences. In the examples, LED spectra 140, 150 and 160 are illustrated to have monotonically decreasing wavelengths (and correspondingly increasing frequencies) whereby $\lambda_1 > \lambda_2 > \lambda_3$, but the algorithm is not meant to imply that other combinations should be excluded, e.g. where $\lambda_2 > \lambda_1 > \lambda_3$. Also laser spectra 165 in algorithm 170 was shown to exhibit a center value wavelength $\lambda_3$ the same as LED spectra 160, but other wavelengths such as $\lambda_1$ or even a completely different wavelength $\lambda_x$ may be used instead without altering the meaning or intent of the invention.

Figure 11:
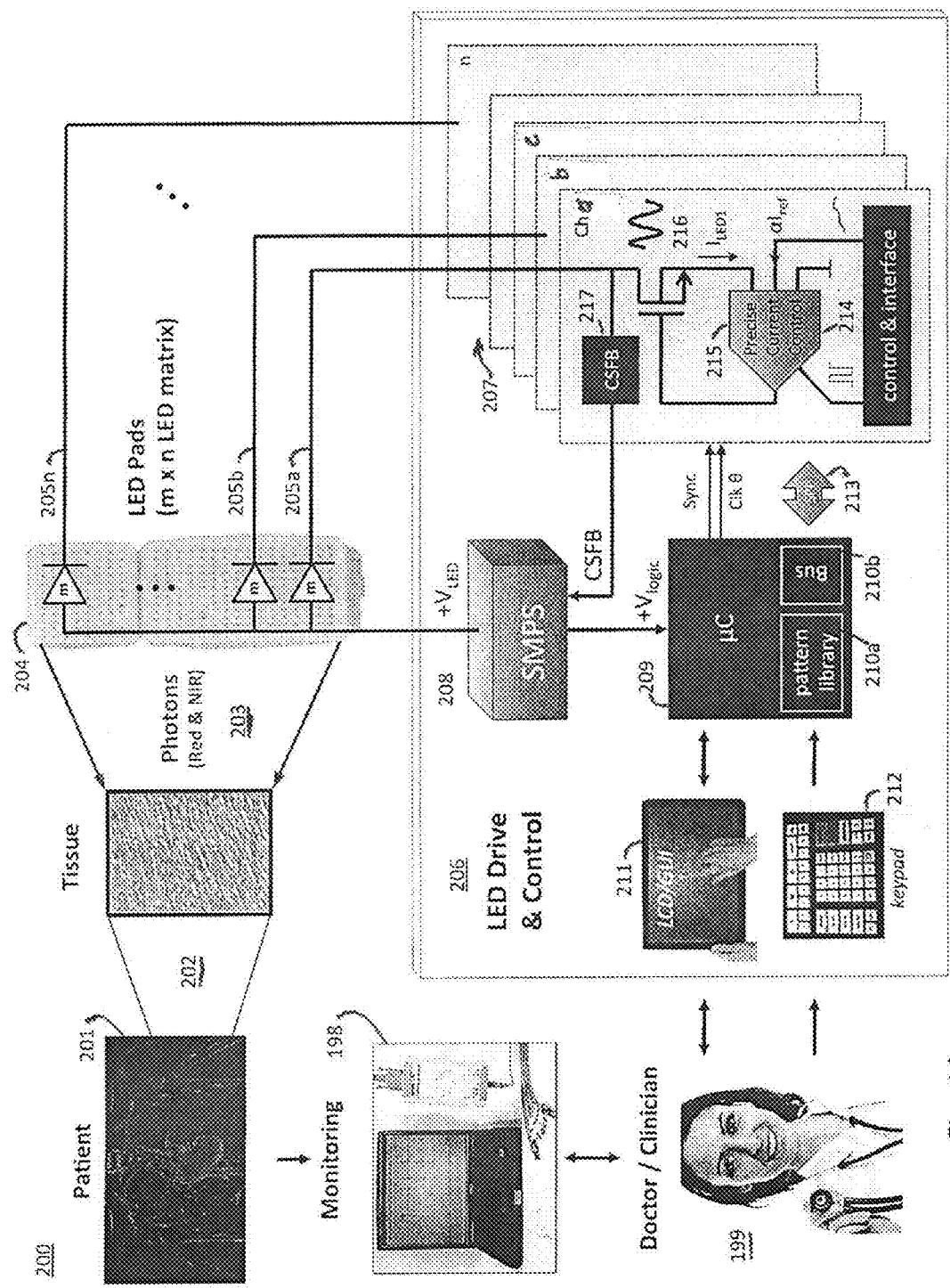
FIG. 11 is a schematic diagram of a dynamic phototherapy system and user interface for programmable waveform synthesis.

Aside from the algorithms needed to realize sequential multi-wavelength phototherapy protocols, a hardware platform, or phototherapy apparatus, is needed facilitating the LED control and waveform generation, the LED array and pad, and a regulated voltage supply to power the LEDs and their drivers. An apparatus able to implement such LED control for photobiomodulation and medical phototherapy is represented in FIG. 11, where LED drive and control apparatus 206 combining a multi-channel LED driver 207 with programmable microcontroller 209, dynamic switching-mode power supply (SMPS) 208, graphics interface 211 and keyboard 212, drives an array comprising LED strings 205a through 205n embedded within aseptic LED pad 204 illuminating tissue 202 of patient 201 with EMR 203 (in this example red and near infrared light) and where a doctor or clinician 199 optionally manages the therapy session while monitoring the patient's condition, before, after, and if desired, during the treatment, on a display 198. Each of LED strings 205a through 205n contains a group of serially-connected LEDs. In one embodiment each of LED strings 205a through 205n contains an equal number "m" LEDs.

Central to LED drive-and-control apparatus 206, microcontroller 209 contains a variety of LED settings and therapeutic algorithms, referred to herein as "pattern library" 210a, stored inside its embedded non-volatile memory. In practice, the programming and LED settings may be permanently stored in a mask ROM, EPROM, in E²PROM or alternatively may be downloaded from a hard disk drive (HDD) and temporarily stored in an SRAM or DRAM. Programming and/or LED settings may also be loaded via USB, Firewire, or Thunderbolt or any other proprietary connectors, over the Internet via Ethernet, or wirelessly via WiFi, Bluetooth, 3G, 4G/LTE, or other wireless protocols.

Microcontroller 209 interfaces to channel drivers 207a through 207n through a digital bus 213, e.g. using a serial peripheral interface (SPI) protocol, implemented in its digital bus port 210b. Within each of its "n" channels, LED driver IC 207 contains a high-voltage current sink MOSFET 216, a current-sense feedback (CSFB) circuit 217, and a precision gate bias and control circuit 215 managed by microcontroller 209 via control and interface 214. Microcontroller 209 also generates the time-based reference clocks Sync and Clk θ that are transmitted over lines 223a and 223b to facilitate waveform generation within channel drivers 207a through 207n. CSFB circuitry 217 delivers a feedback and control signal to SMPS 208 dynamically adjusting the $+V_{LED}$ depending on LED operating currents and requisite voltages.

Figure 12:
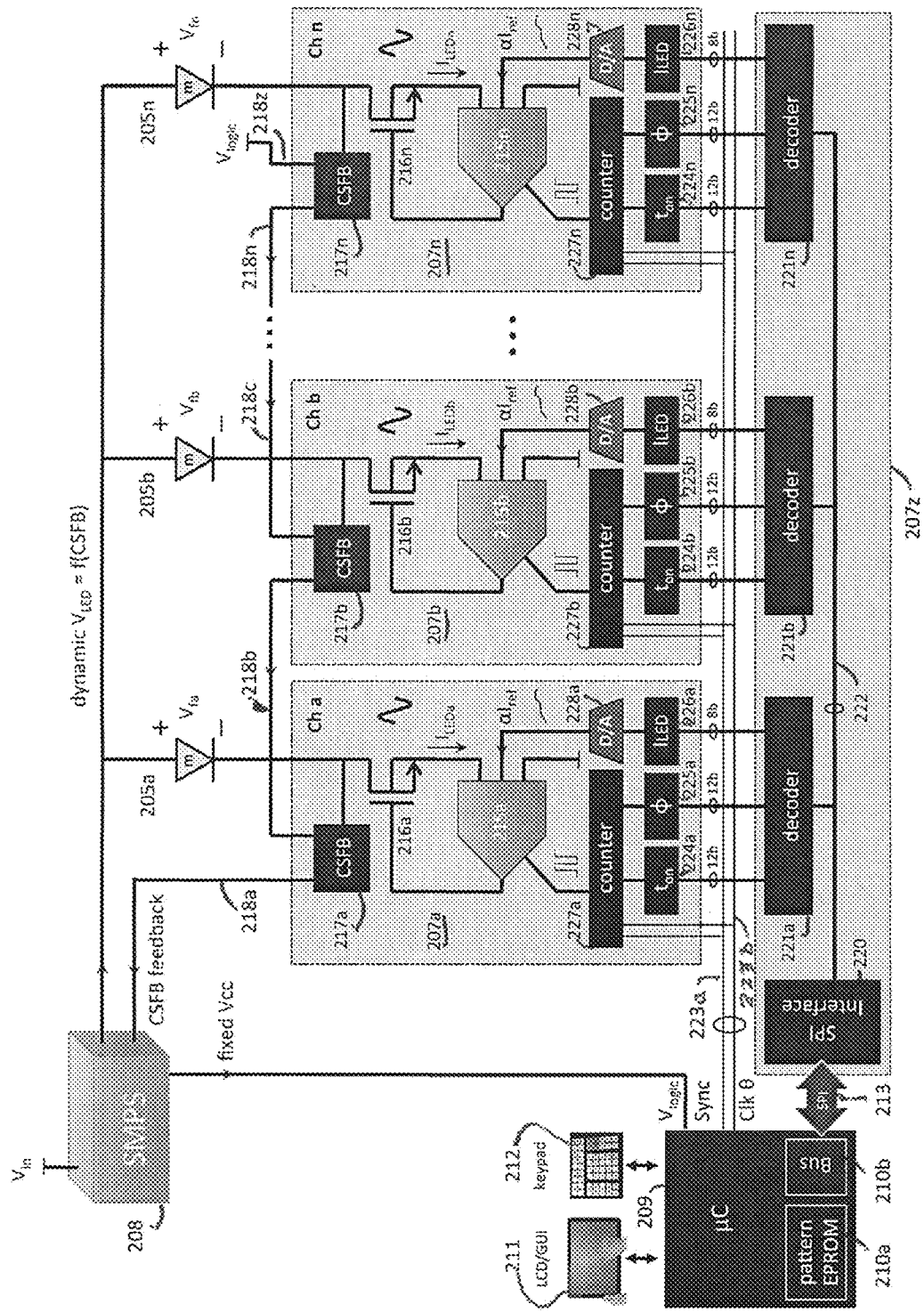
FIG. 12 is a schematic representation of a dynamic phototherapy system with programmable waveform synthesis capability.

One possible implementation of a system for phototherapy LED drive and control 206 is illustrated in greater detail in FIG. 12 comprising control portion 207z and channels a through n comprising channel drivers 207a through 207n driving LED strings 205a through 205n, respectively, where the LED strings 205a through 205n may comprise different types of LEDs having different constructions, dissimilar forward voltages, varying current demands, and emanating different EMR wavelengths $\lambda_1$, $\lambda_2$, $\lambda_3$, $\lambda_4$, etc. LED drivers 207a through 207n are formed on an LED driver IC 207 (FIG. 11), and each of the channel drivers 207a through 207n and its associated LED string represents a channel. The number of channels "n" in the system or within a given driver IC can vary from 1 to 64, with 8 to 16 channels per driver IC being preferable to minimize the number of components while reducing the pin count per IC. A phototherapy apparatus may also utilize more than one driver IC per system. Further information regarding LED drive and control circuitry is disclosed in U.S. Published Application Nos. 2013/0082614 A1, 2013/0099681 A1, and 2013/0147370 A1, each of which was filed on Jan. 9, 2012, and each of which is incorporated herein by reference in its entirety.

To avoid uneven or irregular uniformity in brightness across an LED pad, in a preferred embodiment all "m" LEDs in any given one of LED strings 205a through 205n comprise the same type and wavelength LEDs, selected or sorted for having similar brightness at the same current. For multi-string LED pads having varying types of LEDs in the same pad, strings of any given type and wavelength LED should in a preferred embodiment vary consistently over the n-channels in some regular periodic fashion. For example, in a pad comprising LEDs having wavelength spectra centered around $\lambda_1$, $\lambda_2$, and $\lambda_3$, channels 1, 4, 7, 10, 13 and 16 (or alternatively a, d, g, j, m, and p) comprise strings of $\lambda_1$ type LEDs, channels 2, 5, 8, 11, and 14 (alternatively as b, e, h, k, and n) comprise strings of $\lambda_2$ type LEDs, and channels 3, 6, 9, 12, and 15 (alternatively as c, f, i, l, and o) comprise strings of $\lambda_3$ type LEDs. In a four-wavelength pad, the LED drive system can be arranged in the repeating sequence $\lambda_1$, $\lambda_2$, $\lambda_3$, $\lambda_4$, $\lambda_1$, $\lambda_2$, $\lambda_3$, $\lambda_4$, $\lambda_1$, and ....

The importance of repeating the LED sequence in regular intervals is to provide the most uniform light distribution of any given wavelength LED across a pad without complicating the interconnecting wires to the LED driver IC. If all the like type LEDs were grouped together, e.g. channels 1 through 4 for $\lambda_1$ wavelength LEDs, channels 5 through 8 for $\lambda_2$ type LEDs, etc., interconnection of driver IC 207 to the LED strings 205a through 205n would require many jumpers or an expensive multilayer PCB to connect the LED driver IC to the LEDs.

Contrasting some significant differences between control and drive of LEDs in HDTV backlighting and LED drive in LED phototherapy, the role of the microcontroller in HDTV backlight systems is to act an interpreter, a digital liaison, between the video scalar IC processing video image information, and the backlight controller of the display. In video displays, the knowhow, proprietary algorithms and associated Intellectual property reside in the graphics and video ICs, not in a microcontroller. In fact, the product roadmap for these highly integrated circuits is eventually to eliminate the microcontroller in HDTVs altogether.

In the disclosed phototherapy apparatus, however, the patterns, algorithms, sequences and knowhow in the system for synthesizing waveforms and frequencies used for driving arrays of different types of LEDs is, in a preferred embodiment, not contained in a custom integrated circuit, but instead is contained within the microcontroller or a easily programmable logic device. Moreover, the ability to program and reprogram the controller is key to maintaining flexibility in a rapidly evolving field. Such flexibility is not possible with dedicated and custom integrated circuit systems and solutions. For example in the phototherapy system of FIG. 12, microcontroller 209 contains within its pattern library 210a the waveform synthesis algorithms executed by LED driver IC 207. This waveform information generated by microcontroller 209 is relayed from its internal bus interface 210b to one or more. LED driver ICs, using a high-speed digital bus, in the example via serial peripheral interface (SPI) bus 213. While other digital interfaces may be employed, the SPI bus has become an industry standard in LCD and HDTV backlighting systems, and a common interface for LED driver ICs in large displays (but not in small displays used in handheld electronics).

Using the SPI protocol, each LED driver IC has its own unique chip ID code. All data packets broadcast from microcontroller 209 on SPI bus 213 include this unique chip ID in the header of the data stream as an a type of address—an address employed to direct the data to one and only one LED driver IC, i.e. the target LED driver IC. Only data matching a particular chip ID will be processed by the corresponding target LED driver IC even though all driver ICs receive the same data broadcast. The chip ID is typically hardware-programmed for each LED driver IC with one or two pins on the IC. Using a four-state input where each pin can be either grounded, tied to $V_{logic}$, left open, or grounded through a resistor, a multistate analog comparator interprets the analog level and outputs a 2-bit digital code. Using two pins, a 4-bit binary word (i.e., a binary nibble) uniquely identifies one of $4^2$ or 16 chip IDs. Whenever a data broadcast is received on SPI bus 213 matching the chip ID of any specific LED drive, i.e. the specific IC is "selected", meaning the particular LED driver IC responds to the broadcast instructions and settings. Data broadcasts whose data header do not match a particular LED driver IC's chip ID are ignored. In summary, each LED driver 207 comprising a set of "n" channel drivers is generally realized as a single integrated circuit with its own unique "chip ID" used to direct instructions from the microcontroller 209 directly to that specific IC and to the channel drivers contained within it. The same communication from microcontroller 209 is ignored by all other LED drivers made in integrated circuits without the matching chip ID.

Within control portion 207z of a selected LED driver IC, SPI interface 220 receives the instructions from SPI bus 213 then interprets and distributes this information to decoders 221a through 221n using internal digital bus 222 which instructs the individual channel drivers on drive conditions (including channel by channel timing and LED biasing). For high-speed data transmission with a minimal number of interconnections, internal digital bus 222 comprises some combination of serial and parallel communication. Since the bus is dedicated to the LED driver, such a bus may conform to its own defined standards and is not subject to complying with any pre-established protocol.

This digital information from digital bus 222, once decoded by decoders 221a through 221n, is next passed to digital data registers present in the channel driver within each of channels a through n. For clarity of identification, respective elements within a given channel and its channel driver utilize the same letter designator as the channel for example, CSFB circuit 217 is labeled as 217a in channel a and if shown, as 217b in channel b, while counter 227 is labeled as 227a in channel a and if shown as 227b in channel b. These registers may be realized with S-type or D-type flip-flops, static latch circuitry, or SRAM cells known to those skilled in the art.

In the particular driver IC shown, the decoded data for each channel includes a 12-bit word defining the channel's on-time $t_{on}$, a 12-bit word defining the phase delay $\varphi$, and an 8-bit word defining the LED current, stored respectively in $t_{on}$ registers 224a through 224n, $\varphi$ registers 225a through 225n, and $I_{LED}$ registers 226a through 226n. For example the decoded output of decoder 221a comprising the $t_{on}$, $\varphi$, and $I_{LED}$ data for channel-a is loaded into registers 224a, 225a, and 226a, respectively.

The LED's on-time $t_{on}$ along with the clock signals Clk θ and Sync combine to set the LED's brightness through its corresponding PWM duty factor D, and in waveform synthesis to set the frequency $f_{synth}$ of the synthesized pattern of photoexcitation. Similarly, the decoded output of decoder 221b comprising the $t_{on}$, $\varphi$, and $I_{LED}$ data for channel-b is loaded into registers 224b, 225b, and 226b respectively, and the decoded output of decoder 221n comprising the $t_{on}$, $\varphi$, and $I_{LED}$ data for channel-n is loaded into registers 224n, 225n, and 225n respectively.

These data registers may operate as clocked latches loading data only at predefined times, e.g. whenever a Sync pulse occurs, or may be changed continuously in real-time. Synchronizing the data loading and execution to a clock is known herein as "synchronous" or "latched" operation while operating the latches and counter where the data can be changed dynamically at any time is referred to as "asynchronous" or "non-latched" operation. Latched operation limits the maximum operating frequency but exhibits greater noise immunity than asynchronous operation. In this invention disclosure, waveform synthesis performed by channel drivers 207a through 207n integrated into an IC labeled as LED driver IC 207 under the control of microcontroller 209 can be realized by either method—using either latched or asynchronous methods. In display applications, however, only latched operation is employed because of an LCD image's severe sensitivity to noise.

In non-latched or asynchronous operation, the data received over SPI bus 213 is decoded and immediately loaded into the $t_{on}$, $\varphi$, and $I_{LED}$ registers 224a through 224n, 225a through 225n, and 226a through 226n, Depending on the LED driver IC's implementation, two possible scenarios can occur thereafter. In the first case the count being executed in any given one of counters 227a through 227n is allowed to complete its operation, then the new data is loaded into the counter and the new count commences.

By example, in non-latched operation data freshly loaded from decoder 221a into $t_{on}$, $\varphi$, and $I_{LED}$ registers 224a, 225a, and 226a would wait until the count in counter 227a is completed. After the count is completed the updated data for $t_{on}$ and $\varphi$ in registers 224a and 225a are loaded into counter 227a and simultaneously the updated $I_{LED}$ data in register 226a is loaded into D/A converter 228a changing the bias condition on precision gate drive circuit 215a. After loading the data, counter 227a commences immediately counting pulses on the Clk θ line 223b, first by turning off LED string 205a if it was on, then counting $\varphi$ number of pulses in data register 225a before toggling precision gate bias and control circuit 215a and MOSFET 216a back on. After turning LED string 205a back on, counter 227a then counts $t_{on}$ number of counts loaded from register 224a on Clk θ line 223b before shutting LED string 205a off again. The counter 227a then waits for another instruction.

In the second alternative for non-latched or asynchronous operation behaves exactly the same as the non-latched operation described previously except that whenever an instruction is received via a broadcast on SPI bus 213, the latch is immediately rewritten and simultaneously restarted. Other than cutting short the ongoing count cycle at the time the register data was rewritten, the operating sequence is identical. Regardless of which asynchronous method is used, it takes time to broadcast, decode, and commence operation for each and every channel on a one-by-one basis. In display applications, the delay in writing new data (and changing an LED string's operating conditions) between the first and last channel of an LCD panel may result in flicker and jitter. As such, asynchronous operation is not a viable option in LCD backlighting. In LED phototherapy, however, where a fixed condition may be maintained for minutes, non-latched operation is a viable option especially for generating higher frequency LED excitation patterns, i.e. for higher values of $f_{synth}$.

Unlike in asynchronous operation, where data is updated continually, in latched or synchronous operation LED operating conditions are updated only a predetermined occasions, either synchronized to fixed times, or prescribed events. In latched operation of the circuit shown in FIG. 12, whenever the Sync pulse occurs on line 223a, the data most recently loaded into $t_{on}$ register 224a and $\varphi$ register 225a is loaded into counter 227a. Counter 227a then commences counting the number of phase delay pulses on the Clk θ line 223b before toggling precision gate bias and control circuit 215a on. After completing the count, the counter toggles on precision gate bias and control circuit 215a, biasing the gate of current sink MOSFET 216a to conduct a prescribed amount of current $I_{LED}$ thereby Illuminating LED 205a to desired level of brightness. Counter 227a subsequently counts the number of Clk θ pulses loaded from $t_{on}$ resister 224a until the count is complete, and then toggles precision gate bias and control circuit 215a to shut off current MOSFET 216a and terminate illumination. At this point, depending on the LED driver IC's design, LED 205a may remain off for the remainder of the $T_{sync}$ period, i.e. until the next Sync pulse appears on line 223a, or alternatively repeatedly toggle on and off at the value loaded into duty factor register 224a until the next Sync pulse occurs on line 223a.

On the same $T_{sync}$ pulse, the data most recently loaded into $t_{on}$ register 224b and φ register 225b is loaded into counter 227b. Counter 227b counts the stored number of phase delay pulses φ occurring on the Clk θ line 223b before toggling precision gate bias and control circuit 215b on, biasing the gate of current sink MOSFET 216b to conduct a prescribed amount of current $I_{LEDb}$, thereby illuminating LED 205b to desired level of brightness. Counter 217b subsequently counts the number of Clk θ pulses loaded from $t_{on}$ resister 224b until the count is complete, and then toggles precision gate bias and control circuit 215b to shut off current MOSFET 216b and terminate illumination. At this point, depending on the LED driver IC's design, LED string 205b may remain off for the remainder of the $T_{sync}$ period, i.e. until the next Sync pulse appears, or alternatively repeatedly toggle on and off at the value loaded into duty factor register 224b until the next Sync pulse occurs. A similar process occurs for all n-channels of the LED driver IC.

In latched systems the Sync pulse serves several purposes. First it is an instruction to load the data from the $t_{on}$ and φ registers 224a through 224n and 225a through 225n into the corresponding one of programmable digital counters 227a through 227n. Second it is an instruction to reset the counter and commence counting, first to pass a period of time for phase delay φ, and then to turn on the LED string for the number of clock counts loaded into the corresponding $t_{on}$ register 224a through 224n. Thirdly, it is an instruction to load the value in the $I_{LED}$ register 226a through 226n into the corresponding D/A converter 228a through 228n, precisely setting the analog value of conduction current for that specific channel whenever it is toggled on. Finally it prevents noise from overwriting the data in the data register midstream jumbling the count.

Also triggered by the Sync pulse in latched operation, the bit data loaded into $I_{LED}$ register 226a is simultaneously interpreted by D/A converter 228a to set the reference current $\alpha I_{ref}$ feeding precision gate bias and control circuit 215a. This reference current sets the analog magnitude of LED current $I_{LED1}$ flowing in MOSFET 216a and in LED string 205a whenever the particular channel is toggled on and conducting. It has no bearing on the MOSFET's current when counter 227a toggles the particular 207a channel off. The same process occurs simultaneously for all n channels, i.e. for channel drivers 207a through 207n.

The value of reference current $\alpha I_{ref}$ in any given channel driver is set in two ways. Firstly, a single precision trimmed voltage reference $V_{ref}$ present in channel drivers 207a through 207n along with a precision resistor $R_{set}$ (not shown) sets the value of $I_{ref}$. The resistor $R_{set}$ may be integrated provided that it is trimmed for absolute accuracy during manufacturing, or may comprise a discrete precision resistor, externally connected to the IC that contains LED drivers 207a through 207n. This single reference current is then mirrored to every channel a through n, and as needed may be further trimmed for improved channel-to-channel matching. Secondly, a digitally controlled multiplier α sets the current in each of channels a through n in accordance with the 8-bit word loaded into the corresponding one of $I_{LED}$ registers 226a through 226 n and interpreted by a corresponding one of D/A converters 228a through 228n.

For example in channel driver 207a in channel a, the 8-bit word stored in $I_{LED}$ register 226a is converted into one of 256 levels for the multiplier α, allowing the current in MOSFET 216a and in LED string 205a to be set anywhere from 0% to 100% $\cdot I_{ref}$ in 256 steps, i.e. In increments of 0.39% per step whenever MOSFET 216a is on and conducting. The same operation occurs in each of channel drivers 207b through 207n, enabling digital control of LED current in every LED string 205a through 205n via SPI bus 213.

It should be noted that in an LED backlit HDTV, it is preferable to change LED brightness using PWM dimming rather than by changing the value of the LED current because the color temperature of white LEDs is a function of current. This consideration is not a concern in the disclosed LED phototherapy apparatus. In fact, in LED phototherapy either LED current, PWM brightness control, or a combination of both may be used to set LED brightness. In a preferred embodiment of this invention, however, LED brightness is also set by PWM brightness control, not for purposes of maintaining color temperature of LEDs, but primarily so that the control of LED current can be used for other purposes, specifically for improving safety and facilitating better LED uniformity across a pad. These features in the disclosed invention are described later in this disclosure.

The ability to intelligently and dynamically regulate LED voltage to insure proper biasing of every LED string is another important element of the disclosed phototherapy apparatus. The forward voltage of an LED string varies both with its construction and its current. Since LEDs having different wavelengths require unique and differing construction, their forward voltages are unlikely to match one another as illustrated in the example of FIG. 13.

Defining $V_{\lambda 1}$ as the mean voltage across a string of LEDs emitting a wavelength $\lambda_1$, $V_{\lambda 2}$ as the mean voltage across a string of LEDs emitting a wavelength $\lambda_2$, and $V_{\lambda 3}$ as the mean voltage across a string of LEDs emitting a wavelength $\lambda_3$, and assuming natural variability in manufacturing leads a random (i.e. Gaussian) distribution in forward voltage around its mean of $\pm \Delta V_f$ for LEDs of any given wavelength, then a LED driver used in phototherapy must be able to consistently drive a population of LED voltages comprising the set $V_{\lambda 1} \pm \Delta V_f$, $V_{\lambda 2} \pm \Delta V_f$ and $V_{\lambda 3} \pm \Delta V_f$. If we furthermore arbitrarily define $V_{\lambda 2} > V_{\lambda 1} > V_{\lambda 3}$, then a SMPS must provide a voltage $+V_{LED}$ higher than the highest LED string voltage, mathematically as $$+V_{LED} > (V_{\lambda 2} + \Delta V_{fe}) > V_{\lambda 2} > (V_{\lambda 3} - \Delta V_{fe})$$

Since the highest voltage string is not known a priori, the LED driver IC must be capable of identifying the highest string voltage and to dynamically adjust the LED supply voltage $+V_{LED}$ to a voltage slightly higher than that voltage. Because all the LED strings share a common anode, the LED string with the highest forward drop $V_f$ naturally exhibits the lowest voltage at the cathode of the final LED in the string, i.e. the voltage on the drain of its current sink MOSFET. Each of CSFB circuits 217a through 217n passes the lower of the voltage at its input terminal or the voltage on the drain of the corresponding current sink MOSFET in the channel to its output.

Figure 13:
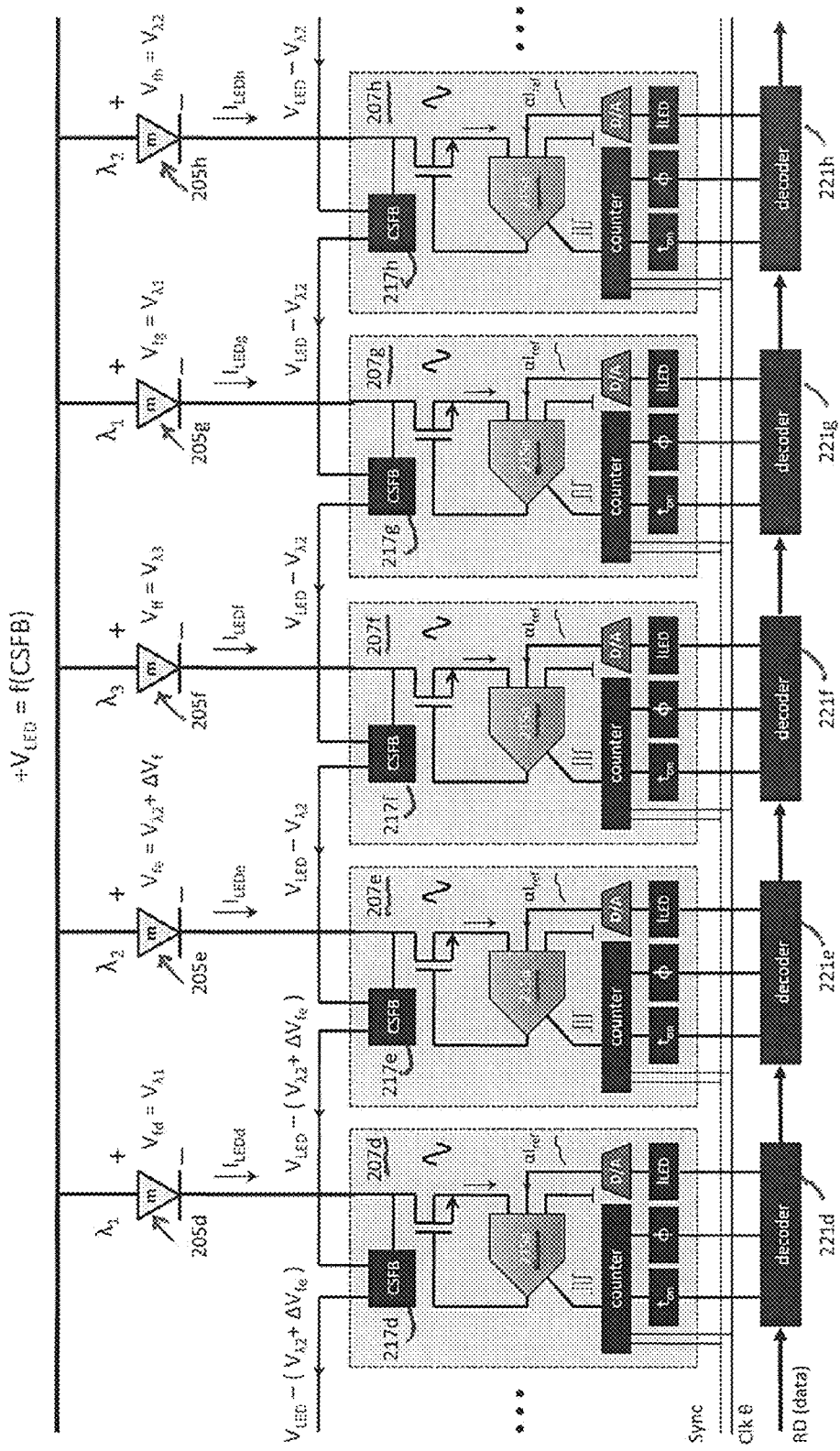
FIG. 13 is a diagram of independent multichannel LED control in a dynamic phototherapy system.

As illustrated in FIG. 13, the CSFB circuits are connected in daisy chain fashion, i.e. in series "head to toe", with the input to CSFB circuit 217d coming from the output of CSFB circuit 217e, the input to CSFB circuit 217e coming from the output of CSFB circuit 217f, and so on. The first CSFB 217n in the chain (not shown) has its input tied to the supply voltage $V_{driver}$ so as to not limit the range of the $+V_{LED}$ output. The last CSFB circuit 217a in the daisy chain (not shown in FIG. 13) drives the input to SMPS 208 ultimately controlling the supply output voltage $+V_{LED}$.

In the example shown in FIG. 13, the output of CSFB circuit 217g outputs a voltage $(V_{LED} - V_{\lambda 2})$. CSFB circuit 217f compares this voltage against the drain voltage of the MOSFET 216f in channel driver 207f, namely ($V_{LED}-V_{\lambda3}$) but since $V_{\lambda2}>V_{\lambda3}$ then ($V_{LED}-V_{\lambda3}$)>($V_{LED}-V_{\lambda2}$) so CSFB circuit 217f outputs the lower voltage, namely ($V_{LED}-V_{\lambda2}$). In the next downstream channel, CSFB circuit 217e compares its input ($V_{LED}-V_{\lambda2}$) against the drain voltage of the MOSFET 216e in channel driver 207e, namely ($V_{LED}-(V_{\lambda2}+\Delta V_{fe})$) but since ($V_{\lambda2}+\Delta V_{fe}$)>$V_{\lambda2}$ then accordingly ($V_{LED}-V_{\lambda2}$)>($V_{LED}-(V_{\lambda2}+\Delta V_{fe})$) so CSFB circuit 217e outputs the lower voltage, namely ($V_{LED}-(V_{\lambda2}+\Delta V_{fe})$). This process continues until CSFB circuit in the last channel (channel a) outputs a voltage to the negative input terminal of SMPS 208. If the negative feedback voltage is decreased, the SMPS 208 responds by increasing its $+V_{LED}$ output. Since the daisy chain of CSFB circuits 217a through 217n in channels a through n outputs the lowest channel voltage (regardless of the order in which the CSFB circuits are connected) then the $+V_{LED}$=f(CSFB) will automatically adjust to supply the minimum needed voltage to power the highest voltage LED string, even if the LEDs are not running at the same currents.

Controlling which channels are conducting is simply a matter of loading the specific register the appropriate data. There are three ways to turn off the current in any given channel in an LED driver IC. First, some LED-driver-ICs have a digitally controlled toggle register to make it convenient to turn a channel on and off independent of its value of D or of its current $\alpha I_{ref}$. Second, the channel to be turned off can be loaded with an on time $t_{on}$=0. Third, the channels to be biased off have their $I_{LED}$ data register 231 set for $\alpha$=0.

Figure 14A:
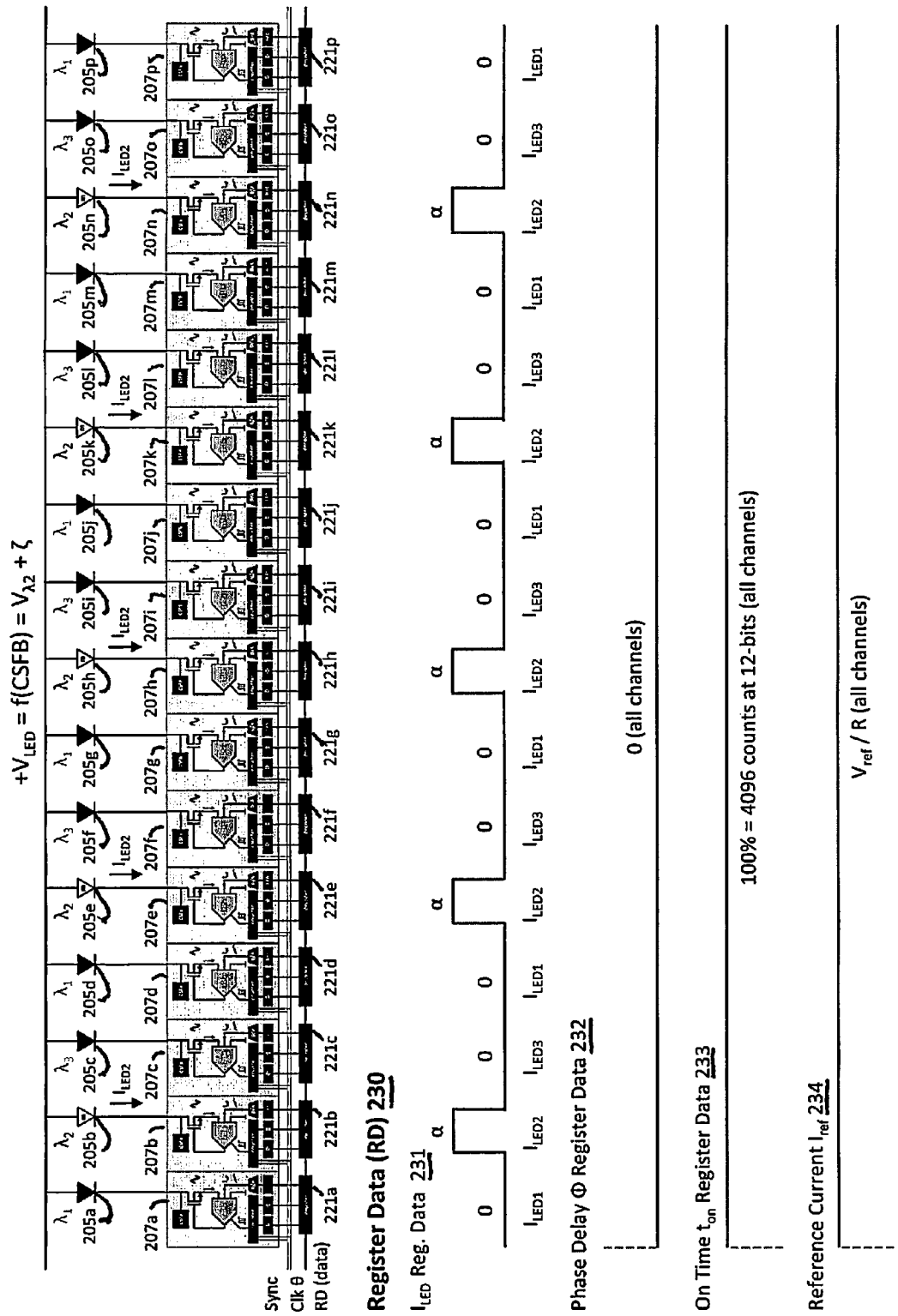
FIG. 14A is a diagram of an example of register data for controlling the current in specific wavelength LED strings in a multi-wavelength dynamic phototherapy system.

The third case is shown in FIG. 14A where only the $\lambda_2$ channels 207b, 207e, 207h, 207k, and 207n are illuminated with a setting of $\alpha$>0, e.g. at 50%. All other channels have $I_{LED}$=0 and therefore $\alpha$=0. The analog parameter $I_{ref}$ is biased to a value $V_{ref}$/R for all channels, the on time $t_{on}$ is equal to the full period $T_{sync}$ (i.e. D=100%), and the phase delay φ is set globally to zero. The current in every one of the five on-channels is then $\alpha I_{ref}$. To power the array of $\lambda_2$ LEDs, $+V_{LED}$ outputs a voltage $V_{\lambda2}+\zeta$ where $\zeta$ the extra voltage above $V_{\lambda2}$ needed to insure the current sink circuit operates properly. All these parameters except for $I_{ref}$ (which is set by an analog voltage and a resistance) are programmed through data registers 221a through 221p contained within the channel decoder circuitry.

Figure 14B:
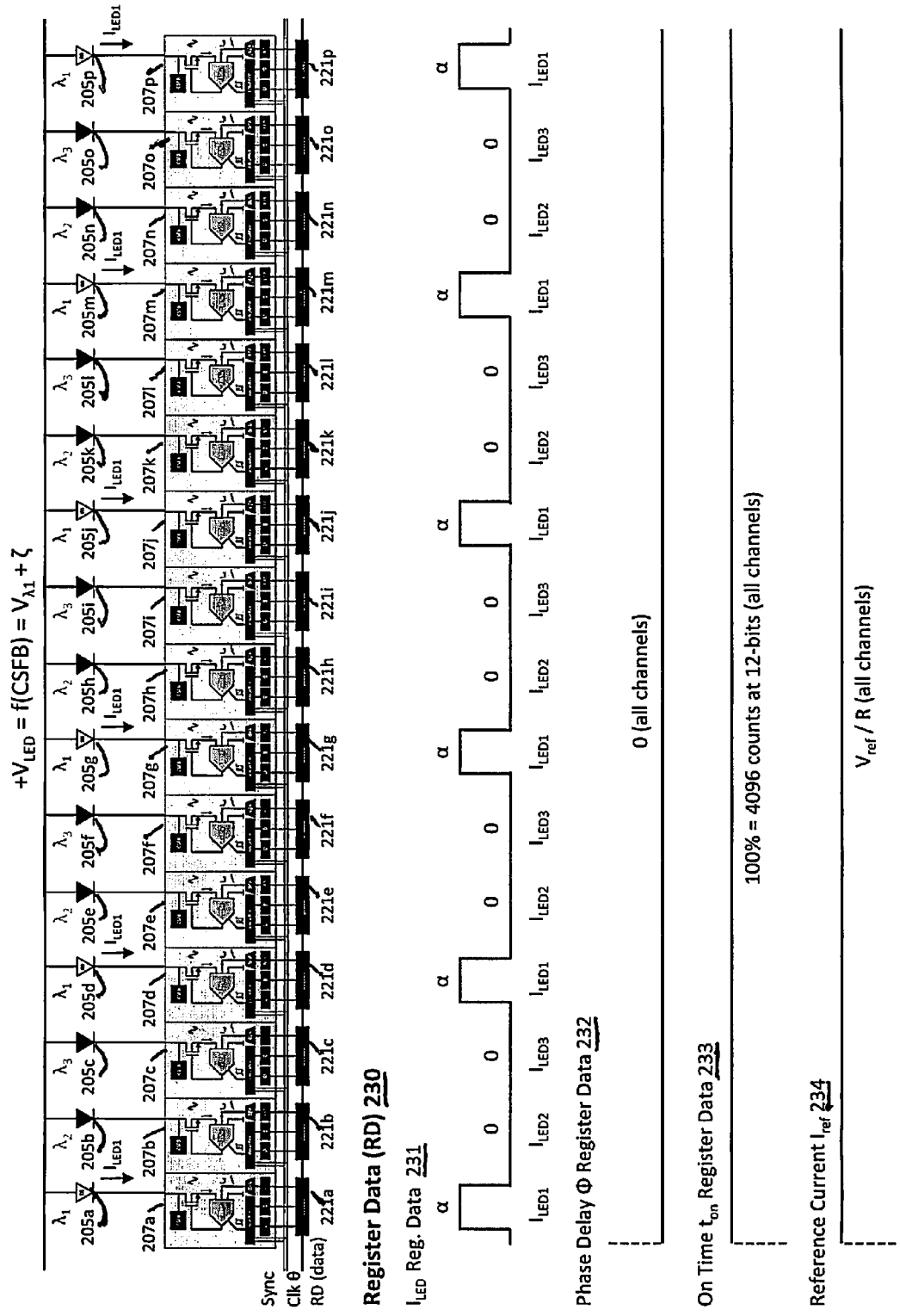
FIG. 14B is a diagram of an example of register data for controlling the current a different wavelength LED strings in a dynamic phototherapy system.

FIG. 14B illustrates that by rewriting the data in registers 221a through 221p the wavelength LEDs being illuminated can easily be changed. In this case $I_{LED}$ register data 231 is changed so that channels 207a, 207d, 207g, 207j, 207m, and 207p are set to a value $I_{LED}$>0 (and therefore $\alpha$>0), e.g. at 50%, and other channels are set to $I_{LED}$=0 (and $\alpha$=0). As previously described, the analog parameter $I_{ref}$ is biased to a value $V_{ref}$/R for all channels, the on-time $t_{on}$ is fixed at the full period $T_{sync}$ (where D=100%) and the phase delay φ is set globally to zero. The current in every one of the six on-channels is then $\alpha I_{ref}$. To power the array of $\lambda_1$ LEDs, $+V_{LED}$ outputs a voltage $V_{\lambda1}+\zeta$ where $\zeta$ is the extra voltage above $V_{\lambda1}$ needed to insure the current sink circuit operates properly.

Ideally, in order to minimize BOM (build of material) costs by taking advantage of economies of scale of semiconductors used in high volume consumer and computing products, the hardware components in a medical phototherapy apparatus can share certain components and ICs with that of LED drivers designed for computer and HDTV backlights. That said, the operating voltages, currents, power levels, heat dissipation considerations, circuit board form factors, passive component selection, and interconnect routing of a computer monitor or HDTV screen are completely different than what is needed in a phototherapy apparatus.

Moreover, in operation, the functions, firmware and software for a medical phototherapy apparatus are completely different from those for HDTV and necessarily address dissimilar issues. One key difference in the purpose of PWM control of LED currents in a HDTV is to facilitate brightness control, either globally (across a screen), or locally (in a portion of the screen), and to synchronize the timing of backlight drive circuitry to that of the video image to avoid aliasing, flicker, pixilation, image blur, and other visual and psycho-optical effects. By contrast, in phototherapy, the purpose of PWM control of LED current is to sequence multiple LED wavelengths while performing waveform synthesis (including both frequency and brightness control).

Programmable Waveform Synthesis

As explained previously, the control variables used in phototherapy are completely different from those used in displays. In an LCD backlighting application, the duty factor D is used only to facilitate brightness control in a backlight operating at a fixed frequency, essentially setting the percent of each Vsync period the LEDs should be Illuminated. The phase delay is used to compensate for signal propagation delays across large area LCD panels. Moreover, in displays, the Vsync period and hence the system's governing operating frequency is fixed. The Vsync pulse maintains a constant rate for the entire HDTV system during operation, for the video image refresh, for every LED driver IC within the backlight system, and for every channel within a driver IC. In LCD displays only certain fixed frequencies and integers multiples thereof are used, e.g. 60 Hz, 120 Hz, 240 Hz, and possibly 480 Hz. While these set frequencies may be user selectable at setup, they remain fixed during use.

In the disclosed invention for phototherapy, however, the variable $t_{on}$ along with the clock signals Sync and Clk θ operate at dynamically varying frequencies, not at fixed frequencies, operating in concert to perform independent waveform synthesis for each channel setting both the photoexcitation pattern's frequency $f_{synth}$ and brightness.

Figure 15A:
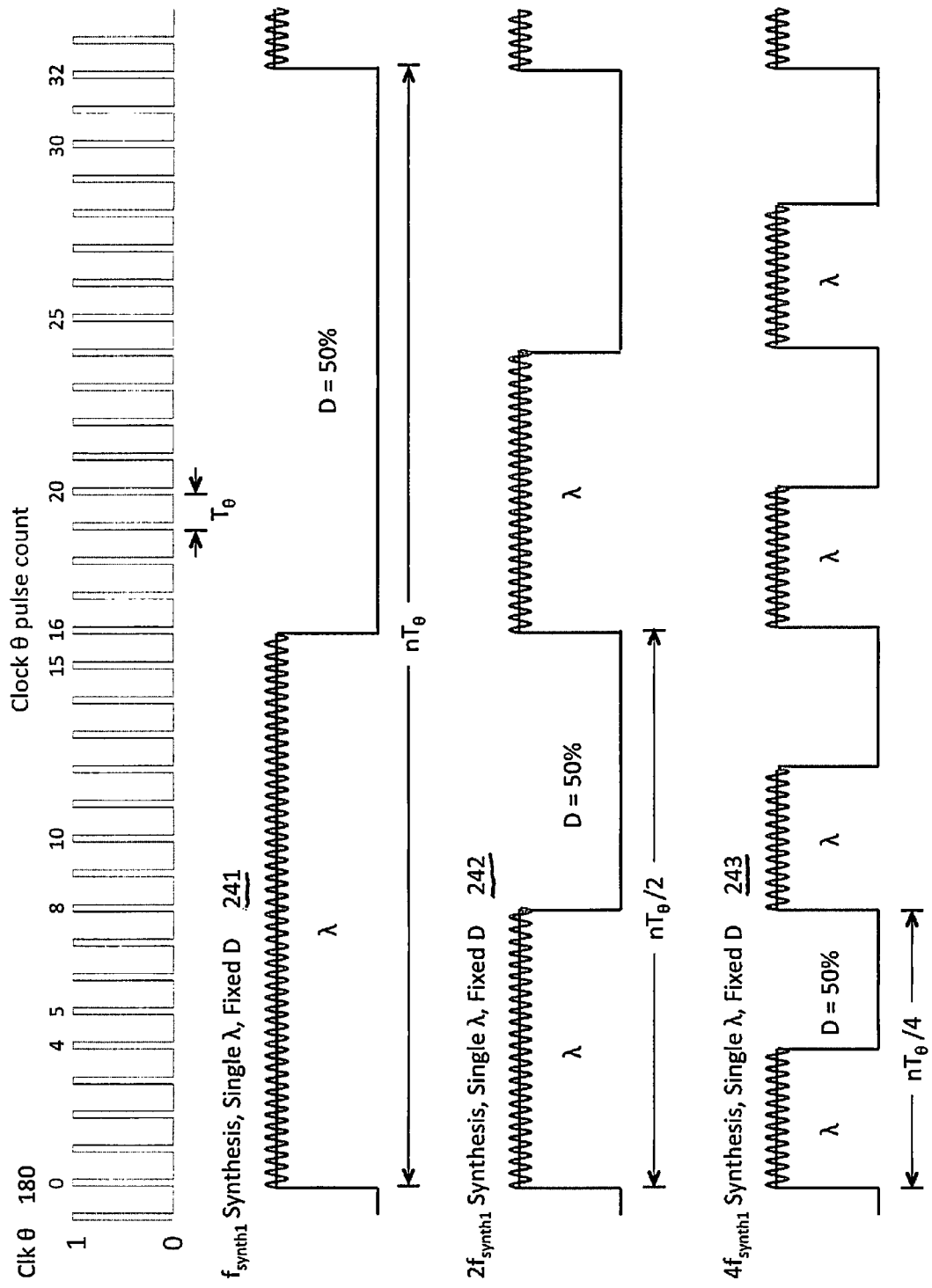
FIG. 15A shows timing diagrams of waveforms at various synthesized frequencies in a dynamic phototherapy system.

For example, in FIG. 15A, three different-frequency LED excitation patterns 241, 242, and 243 are synthesized from a single clock 180 generated from microcontroller 209, all with a resulting duty factor controlled brightness of 50%. As shown, pulses from clock Clk θ repeat with period $T_θ$, for example at 9.346 kHz and a corresponding period $T_θ$=107 μsec. In digitally synthesized waveform 241, an array of LEDs of wavelength λ is turned on for 16 clock pulses (by programming the on time $t_{on}$=16) and then subsequently turned off. If a 12-bit counter is employed, the full count for the counter is 4096 clock pulses, which at this clock frequency corresponds to maximum period of $T_{cntr}$=4096·0.107 msec=438 msec meaning that without intervention from the microcontroller, the array of LEDs would remain off for another 4080 pulses after being on for only 16 pulses. At full count, the resulting frequency of the counter's output would be $f_{cntr}$=2.28 Hz.

Rather than letting the clock run to its full count of 4096, instead, at time t=32 pulses (only 16 pulses after the LEDs shut off) the cycle is forced to repeat. Forcing a shorter period can be accomplished in several ways. In asynchronous (non-latched) mode, the registers can be written by the SPI bus after the 31$^{st}$ clock pulse but before the 32$^{nd}$ pulse. Since the SPI bus can broadcast data at 10 MHz and each clock pulse lasts 107 μsec, there is plenty of time to change the register data to terminate on the 32$^{nd}$ pulse. Only the specific channel is affected.

If more than one channel requires resetting and restarting its corresponding counter, each channel must be instructed via the SPI bus one-by-one. Alternatively, in latch (synchronous) mode, the count can be restarted by a Sync pulse after the $31^{st}$ clock pulse but before the $32^{nd}$ pulse. On the $32^{nd}$ pulse, the sequence will naturally restart its count on this channel and every other channel that is biased into an on state (i.e. where $t_{on}>0$ and $I_{LED}>0$). Unless the data in the $t_{on}$, $\varphi$, and $I_{LED}$ registers is changed prior to the Sync pulse, the prior data will be loaded into the counter and the last cycle repeated. If new data is loaded, the new data will take effect synchronous to the Sync pulse.

The resulting synthesized waveform is a square wave where an array of LEDs of wavelength $\lambda$ conducts for 16 clock pulses and is off for 16 pulses. The synthesized waveform 241 therefore has a period of 32 clock pulses or $nT_\theta = 32 \cdot 0.107$ msec = 3.424 msec with a corresponding frequency $f_{synth1} = 1/nT_\theta = 292$ Hz.

Because the on time and off time are equal, i.e. $t_{on} = t_{off}$, and the period $T_{synth} = t_{on} + t_{off}$ then the synthesized duty factor is given by $$D = t_{on}/T_{synth} = t_{on}/(t_{on}+t_{off}) = t_{on}/2t_{on} = 50\%$$

So even though the $t_{on}$ register was programmed for only 16 pulses corresponding to a duty factor of D=16/4096=1/256=0.39% for a 12-bit counter at its full count of 4096 (with a corresponding frequency $f_{cntr}=2.28$ Hz), because the counter was restarted at t=32 pulses, the resulting duty factor and frequency are 128 times higher, i.e. 50% and 292 Hz.

Note that in latched operating mode, the Sync pulse must occur at a frequency equal to or higher than the frequency of the waveform being synthesized, i.e. $T_{sync} \leq nT_\theta$ or as expressed by the frequency relation $f_{sync} > f_{synth}$. If this criterion is not met, there is no way to update the data registers in time to force the counter retriggering to meet the specified synthesized frequency.

Electrically, the synthesized frequency $f_{synth1}=292$ Hz corresponds closely to the musical note D above middle C in the audio spectrum, or $D^0$. As described previously, the natural operating frequency of many organs and tissue such as the heart, lungs, intestines, nerves and the brain, the maximum data rate for vision and hearing, along with many molecule vibrations all occur in the audio and subsonic spectrum of frequencies, mostly under a few kilohertz and some as low as one hertz. Even though the synthesized frequency is manifested as repeating series of light pulses and not as sound, the impinging light energy is absorbed and redistributed into molecules and tissue at the same frequency, leading to a physical response in kinetic and potential energy synchronous to audio spectra. As such, it is convenient, if not insightful, to use music notation to describe the synthesized photoexcitation waveforms musically as notes chords rather than mathematically as Fourier series and transformations.

In digitally synthesized waveform 242 of FIG. 15A, an array of LEDs of wavelength $\lambda$ is turned on for 8 clock pulses (by programming the on-time setting to $t_{on}=8$) and then subsequently turned off. If a 12-bit counter is employed, the full count for the counter is 4096 clock pulses, which at this clock frequency corresponds to maximum period of $T_{cntr}=4096 \cdot 0.107$ msec=438 msec meaning that without intervention from the microcontroller, the array of LEDs would remain off for another 4088 pulses after being on for only 8 pulses.

Rather than letting the clock run to its full count, instead, at time t=16 pulses (only 8 pulses after the LEDs shut off) the cycle is forced to repeat. As in waveform 241, forcing a shorter period can be accomplished in several ways. In asynchronous (non-latched) mode, the data registers can be written by the SPI bus after the $15^{th}$ clock pulse but before the $16^{nd}$ pulse. Since the SPI bus can broadcast data at 10 MHz and each clock pulse lasts 107 µsec, there is plenty of time to change the register data to terminate on the $16^{th}$ pulse. Only the specific channel is affected.

If more than one channel requires resetting and restarting its corresponding counter, each channel must be instructed via the SPI bus one-by-one. Alternatively, in latch (synchronous) mode, the count can be restarted by a Sync pulse after the $15^{th}$ clock pulse but before the $16^{th}$ pulse. On the $16^{th}$ pulse, the sequence will naturally restart its count on this channel and every other channel that is biased into an on state (i.e. where $t_{on}>0$ and $I_{LED}>0$). Unless the data in the $t_{on}$, $\varphi$, and $I_{LED}$ registers is changed prior to the Sync pulse, the prior data will be loaded into the counter and the last cycle repeated. If new data is loaded, the new data will take effect synchronous to the Sync pulse.

The resulting synthesized waveform is a square wave where an array of LEDs of wavelength $\lambda$ conducts for 8 clock pulses and is off for 8 pulses. The synthesized waveform 242 therefore has a period of 16 clock pulses or as $nT_\theta=16 \cdot 0.107$ msec=1.712 msec with a corresponding frequency $f_{synth2}=2/nT_\theta=584$ Hz. The resulting waveform has a frequency exactly double that of the prior example where $t_{on}=t_{off}=16$ pulses, so that $f_{synth2}=2f_{synth1}=584$ Hz. Since $f_{synth1}$ was synthesized to oscillate at an audio spectrum frequency corresponding to the musical note D above middle C, or $D^0$, then at double that frequency $f_{synth2}$ also oscillates at the musical note "D", except one octave higher than middle C. i.e. $D^1$.

Waveform 243 illustrates synthesis of a photoexcitation pattern having a frequency four times that of waveform 241, or as $f_{synth3}=4f_{synth1}$. As such, the on-time $t_{on}$ is set to 4 clock pulses and the counter is reset at 8 clock pulses. The resulting synthesized waveform is a square wave where an array of LEDs of wavelength $\lambda$ conducts for 4 clock pulses and is off for 4 pulses. The synthesized waveform 243 therefore has a period of 8 clock pulses or as $nT_\theta=8 \cdot 0.107$ msec=0.856 msec with a corresponding frequency $f_{synth3}=4/nT_\theta=1,168$ Hz, corresponding to the musical note D two octaves above middle C, or $D^2$.

Summarizing the synthesized waveforms Table 1 illustrates that a 12-bit counter and 9.346 kHz clock can algorithmically synthesize a wide range of frequencies by resetting the programmable counter at the appropriate time, i.e. so $T_{reset} \leq T_{synth}$ where the reset may occur asynchronously through the SPI bus or synchronously using the Tsync pulse. By extrapolation $f_{synth4}$ and $f_{synth5}$ were generated by doubling and quadrupling the period of the 292 Hz $D^0$ waveform-synthesis, resulting in 146 Hz and 73 Hz frequencies corresponding to the musical notes D one octave and D two octaves below middle C, i.e. $D^{-1}$ and $D^{-2}$.

TABLE 1

Algorithmically synthesized waveforms

| Clock θ | Counter | $D_{entr}$ | $T_{reset}$ | $T_{synth}$ | $f_{synth}$ (note) | $D_{synth}$ | Name |
|---|---|---|---|---|---|---|---|
| 9.346 kHz T = 107 µs | 12 bit 4096 step f = 2.28 Hz T = 438 ms | 64 | 128 | 13.696 ms | 73.0 Hz ($D^{-2}$) | 50% | $f_{synth5}$ |
| | | 32 | 64 | 6.848 ms | 146 Hz ($D^{-1}$) | 50% | $f_{synth4}$ |
| | | 16 | 32 | 3.424 ms | 292 Hz ($D^0$) | 50% | $f_{synth1}$ |

TABLE 1-continued

Algorithmically synthesized waveforms

| Clock θ | Counter | $D_{entr}$ | $T_{reset}$ | $T_{synth}$ | $f_{synth}$ (note) | $D_{synth}$ | Name |
|---|---|---|---|---|---|---|---|
| | | 8 | 16 | 1.712 ms | 584 Hz ($D^1$) | 50% | $f_{synth2}$ |
| | | 4 | 8 | 0.856 ms | 1,168 Hz ($D^2$) | 50% | $f_{synth3}$ |

The disclosed method to algorithmically synthesize waveforms of different frequencies can be adapted to the previously disclosed phototherapy sequential waveform synthesis algorithm 170 shown in FIG. 10A simply by changing the channels being driven from those controlling LEDs with $\lambda_2$ wavelengths, to those channels controlling LEDs with $\lambda_1$ wavelengths as illustrated previously in FIG. 14A and FIG. 14B. The resulting output of the LED pad using multiple wavelength LEDs at a fixed brightness and photoexcitation frequency is illustrated in waveform 245 of FIG. 15B where an array of LEDs at $\lambda_2$ wavelengths driven at a PWM brightness of 50% and frequency $f_{synth}$ changes at time $t_1$ into an array of LEDs at $\lambda_1$ wavelengths driven at a PWM brightness of 50% and the same frequency $f_{synth}$ changes.

Figure 15B:
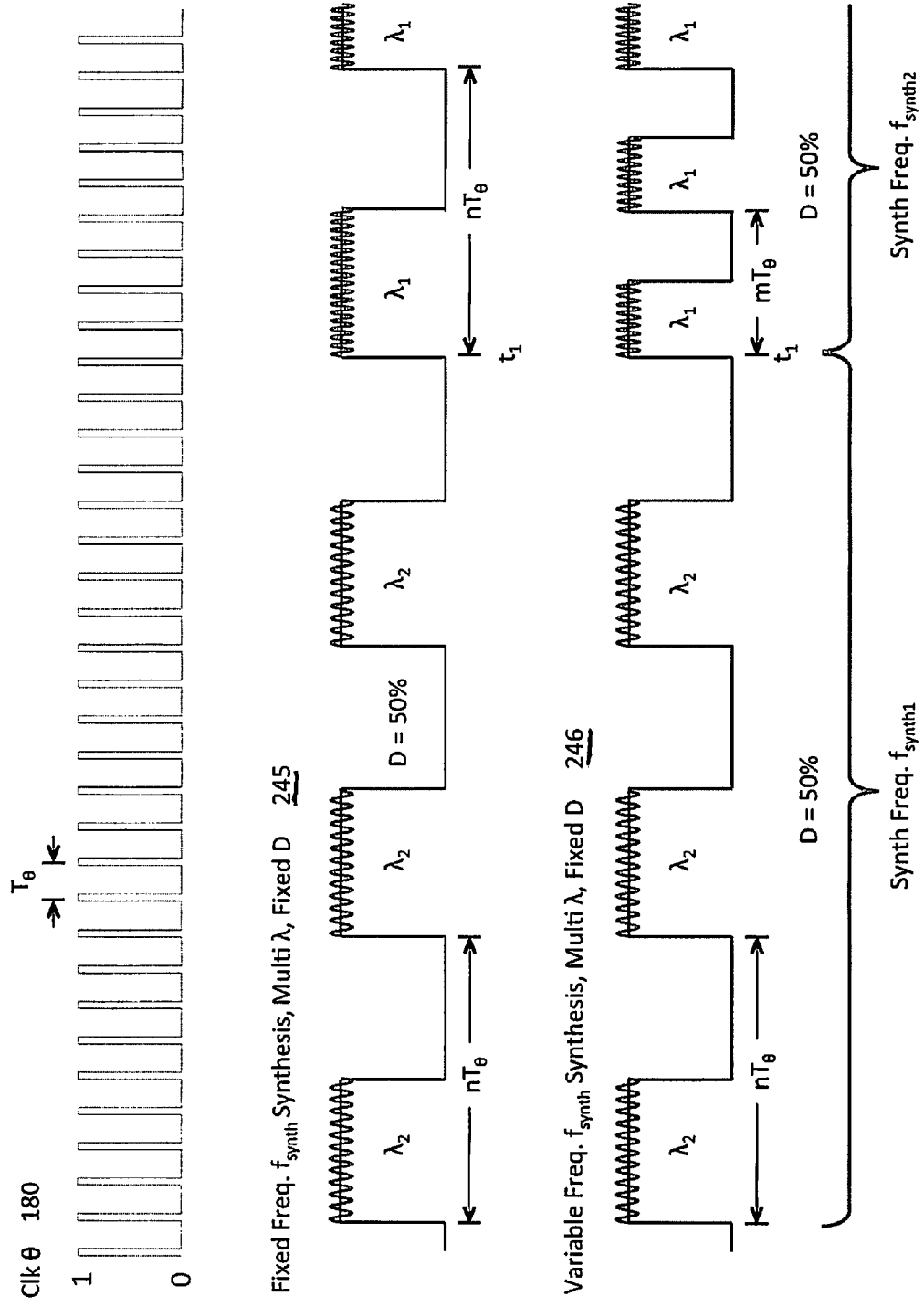
FIG. 15B shows timing diagrams of multiple-wavelength LED strings at various synthesized frequencies in a dynamic phototherapy system.

In an alternative embodiment the synthesized frequency and the LED wavelength can both be changed dynamically as illustrated in waveform 246 of FIG. 15B. In this example an array of $\lambda_2$ wavelength LEDs driven at a PWM brightness of 50% and frequency $f_{synth1}$ changes at time $t_1$ into an array of LEDs at $\lambda_1$ wavelengths driven at a PWM brightness of 50% but at a different frequency $f_{synth2}$. As illustrated the frequency given by $f_{synth1}=1/nT_\theta$ and the frequency given by $f_{synth1}=1/mT_\theta$ are different simply because m≠n, without requiring any change in the frequency of clock Clk θ.

It is also possible to excite different strings of LEDs, e.g. of the same wavelength, at different photoexcitation frequencies simultaneously, i.e. to synthesize $f_{synth1}$ and $f_{synth2}$ concurrently, a method referred to herein as "harmonizing", i.e. forming harmonic frequency multiples through waveform synthesis. For example, a given therapy may find efficacy is improved in two frequencies such as $D^0$ and $D^1$ are used together. It should be mentioned that mixing multiple synthesized photoexcitation frequencies together ("harmonizing") is different that concurrently illuminating tissue with different wavelengths of light ("blending") discussed and summarized previously in FIG. 9E. While the concept of multiple co-synthesis of photoexcitation frequencies may appear obvious if not trivial, using the hardware of LED driver ICs the task is not straightforward.

Referring once again to Table 1 and FIG. 15A, recall that if a range of waveform frequencies is synthesized on different channels concurrently using latched mode operation, the rule that the reset pulse must be equal to (or faster than) the synthesized frequency applies to the highest synthesized frequency. For example if one channel synthesizes 584 Hz signal $f_{synth2}$ shown by waveform 242, then the counter of every channel will necessarily be reset by $T_{sync}$ at time t=16, 32, 48 . . . pulses, forcing every channel to reload their corresponding data registers and restarting their counts. This requirement to reset the counter every 16 pulses, i.e. at a frequency of 584 Hz or faster, remains in effect so long that $f_{synth2}$ is the highest frequency being generated. If alternatively an even higher frequency such as $f_{synth3}=1.168$ Hz is synthesized, the Sync pulse must occur at even a higher frequency, at least as fast as the synthesized frequency, meaning in the minimum $1/T_{sync} > f_{synth3}$.

Every time a Sync pulse occurs, any channel switching at a lower frequency must be restarted in a manner that preserves its present count value, meaning it must be restarted with new $t_{on}$ and φ to continue doing what it was doing until its programmed period is completed. Specifically any channel still on and conducting should be restarted in the on condition with a on-time $t_{on}$ loaded into the counter equaling the intended on-time less the number of counts that already occurred with that channel on. Likewise any channel already having completed its count, off and non-conducting should be restarted in the off condition with a phase delay φ loaded into the counter equaling the intended off-time less the number of counts that already occurred with that channel off.

Figure 16:
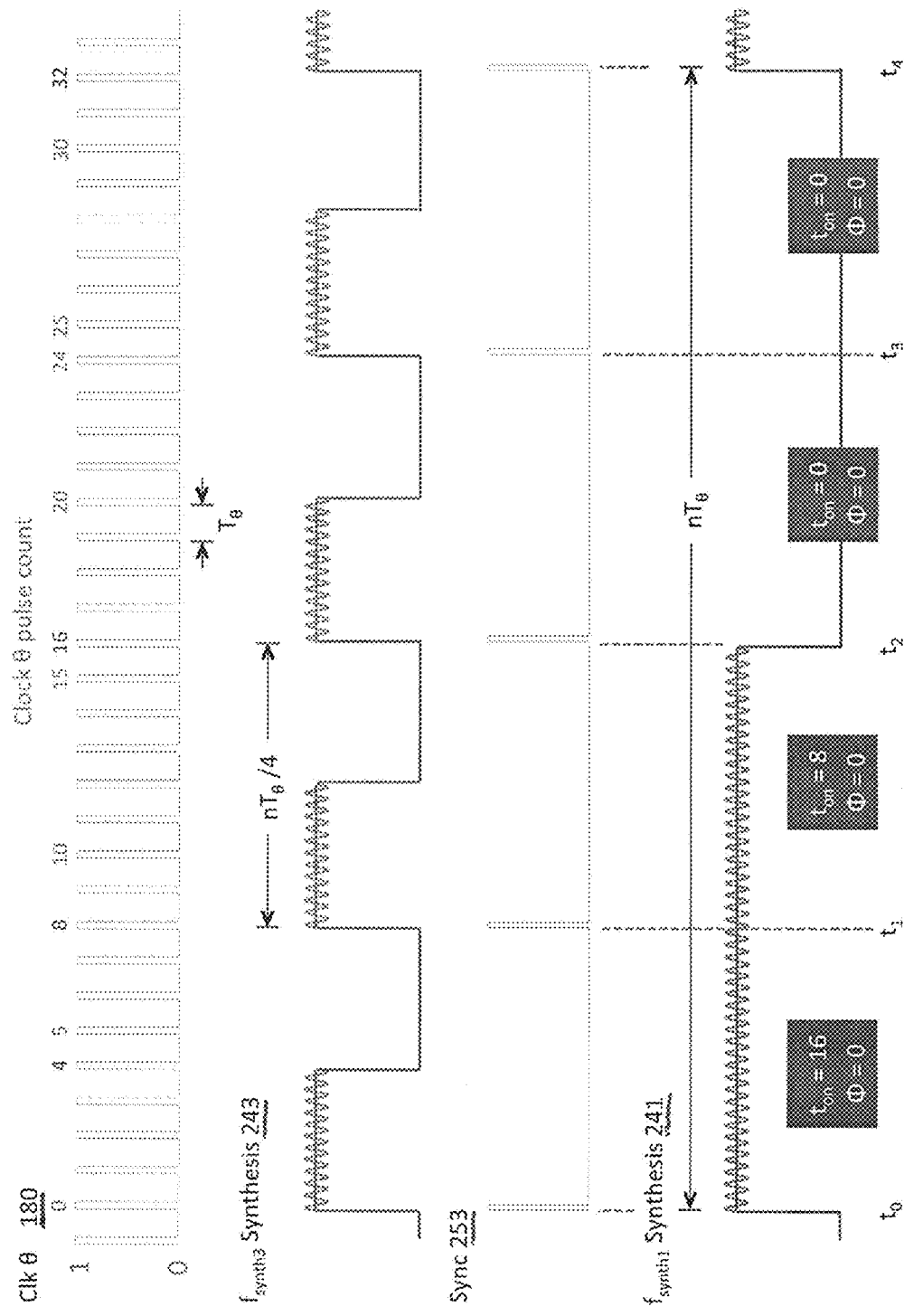
FIG. 16 is a timing diagram illustrating data register updates for concurrently synthesizing two different photoexcitation frequencies.

This multi-frequency drive requirement for synchronous mode waveform synthesis example is clarified in FIG. 16, where the highest frequency synthesized waveform 243 has a frequency $f_{synth3}$ four times higher than that of $f_{synth1}$ waveform 241, i.e. the period of waveform 241 is $nT_\theta$, and where the shorter period of waveform 243 has a period $nT_\theta/4$. As shown in waveform 180, clock Clk θ has in this example a fixed frequency $1/T_\theta$. If we assume the aforementioned values where clock Clk θ has a frequency of 9.346 kHz and a period $T_\theta=107$ μs, where $f_{synth1}=292$ Hz and where $f_{synth3}=1,168$ Hz, then the Sync pulse 253 must occur at a frequency no slower than 1,168 Hz, i.e. every 8 clock pulses (0.856 msec). Since the Sync pulses occur every 8-clock-pulses, on pulses 8, 16, 24, 32 . . . then the register data for the synthesis of $f_{synth1}$ waveform 241 requires updating with every Sync pulse.

As shown in FIG. 16, at the onset, i.e. at time $t_0$, the register data for waveform 241 is loaded as $t_{on}=16$ and φ=0, meaning the LED string turns on immediately and will stay on for 16 pulses unless interrupted. When the next Sync pulse occurs at time $t_1$, not only is the register data for waveform 243 necessarily updated but so is waveform 241 as well, being loaded with data $t_{on}=8$ and φ=0 since the channel was intended to be on for 16 pulses and 8 pulses have elapsed, leaving 8 more to go. Actually any value of $t_{on}$ equal to or greater than 8 would work equally well (since the channel will be forced off at $t_2$ anyway) but for programming purposes it is convenient to keep track of the remaining conduction time, especially for when PWM brightness control is invoked and $t_{on} \neq t_{on}$. At time $t_1$ it is important to maintain φ=0; otherwise the LEDs for the affected channels would turn off at the time of the Sync pulse.

Later, at time $t_2$ when the next Sync pulse occurs, the register data for waveform 241 is again updated, this time turning off the channel with the settings $t_{on}=0$ and φ=0 or 16. Setting $t_{on}=0$ forces the channel off regardless of the value phase delay φ.

Although not preferred, in an alternative approach the phase delay φ can be used to keep the channel off, e.g. setting φ≥8 delays it from turning on before the next Sync pulse occurs even if $t_{on}>0$. Eight clock pulses later, at time $t_3$ the channel must once again be kept off insuring the register data is loaded with $t_{on}=0$. Although the channel can also be kept off by setting φ≥8, in a preferred embodiment the channel is kept off by maintaining $t_{on}=0$, reserving the phase delay feature for another purpose and not dedicated to performing waveform synthesis.

In manner prescribed, the simultaneous synthesis of two waveforms 241 and 243 having dramatically different frequencies $f_{synth1}$ and $f_{synth3}$ can be achieved even when using synchronous, i.e. latch mode, operation. So by the judicious choice of the values of on-time $t_{on}$, phase delay φ, and the forced timing of the Sync pulse, synchronous mode operation can achieve synthesis of any number of square wave and pulsed photoexcitation waveforms up to a frequency limited by the maximum operating rate of the LED driver ICs. Usually this restriction occurs because of the maximum rate of Clk θ clock 180 used for counting pulses, and not by the maximum frequency of the Sync pulse itself.

For example in FIG. 12, the LED driver IC 207 includes $t_{on}$ and φ registers employing a 12-bit register and counter. For latched operation at maximum resolution, Clk θ should be 4096 times faster than the Sync pulse rate, regardless of the elapsed time (in milliseconds) of period $T_{sync}$. At a fixed clock rate operating at the full count on the counters 227a through 227n, the meaning of the number stored in the $t_{on}$ registers divided by 4096 truly represents the duty factor of the counter $D_{cntr}=t_{on}/T_{sync}$. This duty factor $D_{cntr}$ defines up to 4096 increments of LED on time per Sync period, and the phase delay φ defines up to 4096 increments of the turn-on delay time in any given Sync period when the LED first turns on.

Since Clk θ normally runs 4096 times faster than the Sync pulse rate, i.e. where $f_\theta=4096/T_{sync}$ the fastest circuit (and therefore the function most likely to limit the speed of operation) is the maximum frequency which the counters can count accurately. Synthesizing the aforementioned $f_{synth3}$ waveforms at 1,168 kHz requires that Sync operate at the same speed, and since Clk θ must run a frequency 4096 times higher, then $f_\theta=4096/T_{sync}\geq 4096\cdot f_{synth}=4.784$ MHz, a much higher speed than required in most display applications. As mentioned previously, the highest Vsync refresh rate used in high-end HDTVs is 480 Hz and many can't even operate beyond 240 Hz. If a LED driver IC is designed to work only up to this Vsync refresh rate 480 Hz, it means $f_\theta$ operates a maximum rate just beyond 1.97 MHz, e.g. 2 MHz.

To overcome this limitation without the need to redesign the LED driver IC or develop custom ICs, the microcontroller program can be altered to generate a 10-bit clock for counting rather than 12-bits. Since the counter performing PWM control and dimming is designed for operation with 12-bits of resolution, i.e. 4096 increments of time and duty factor, it is not obvious to drive a 12-bit counter with a 10-bit clock, one where $f_\theta=1024/T_{sync}$. But as illustrated previously in this disclosure, in the phototherapy application frequency synthesis is the key parameter, not precision brightness control. Since the Sync pulse cuts short the full count, this precision of brightness control is not utilized anyway. In such a case, operating at a clock rate 1024 times that of the Sync pulse expands the range of waveform synthesis to higher frequencies.

For instance a 2 MHz clock using synchronous mode operation with 12-bits of precision is shown previously only able to synthesize digital (pulse) waveforms up to 480 Hz. Using 10-bits of precision in the same control scheme increases the maximum synthesized frequency by 4×, from 480 Hz to 1.92 KHz, enough to synthesize frequencies equivalent to the musical note $D^2$ (and beyond). The frequency demands for sine wave synthesis are however more stringent and beyond the scope of this disclosure.

Another method is to run Clk θ at its maximum possible rate and to generate the Sync pulse independently of Clk θ except that the Sync pulse should be forced to occur on the rising edge the next available Clk θ pulse using an AND gate, a one shot monostable multivibrator, or a simple PLL (phase locked loop). The synchronized versions of the Sync and Clk θ signals are then broadcast to the LED driver ICs on clock lines 223a and 223b, respectively, except unlike in previously described cases wherein the two clock signals operate with a fixed ratio, in this embodiment they do not.

If even higher synthesized frequencies of square wave pulses are demanded, high-speed clock circuitry may be utilized, or alternatively latched (synchronous) operation can be replaced by non-latched (asynchronous) operation.

Figure 15C:
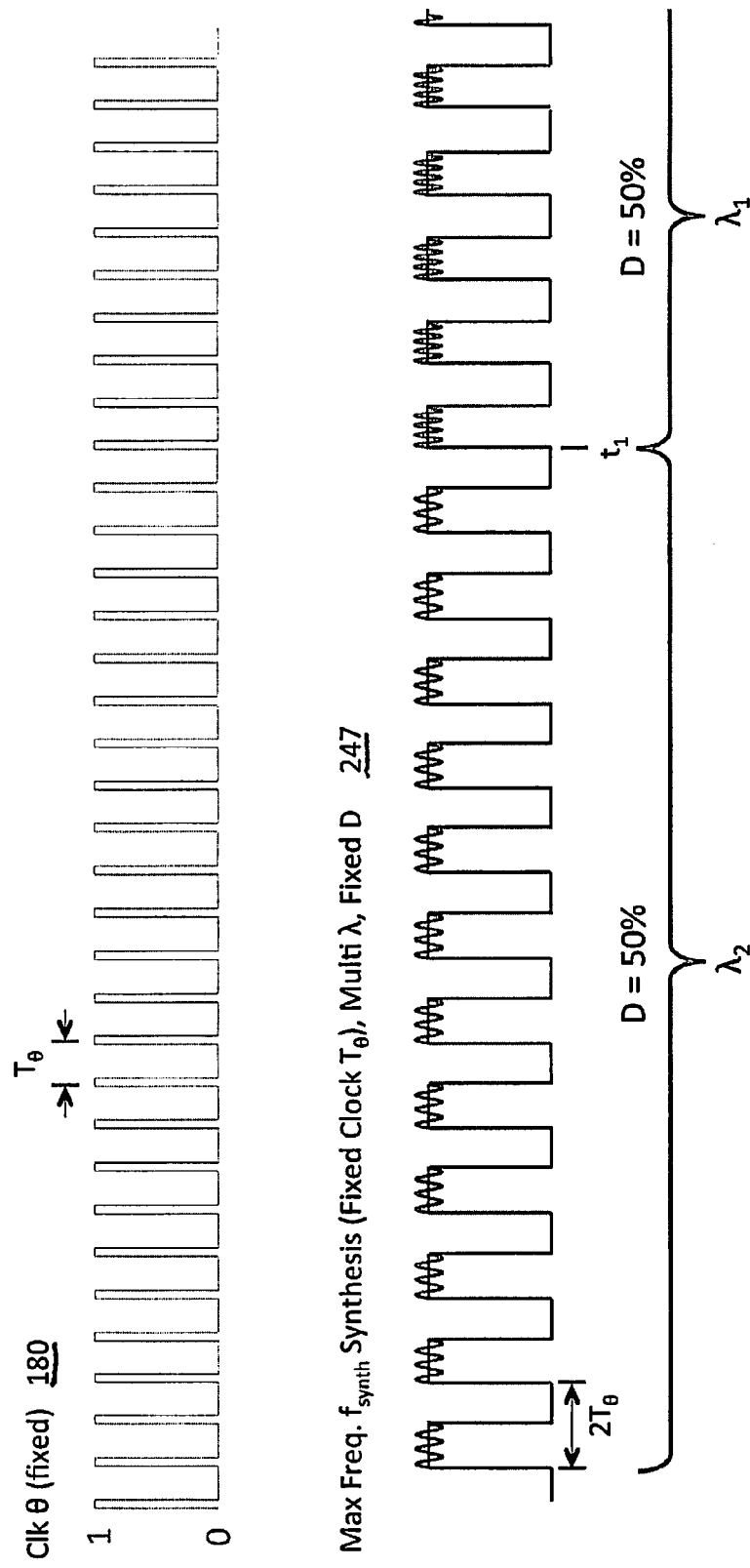
FIG. 15C is a timing diagram of multiple-wavelength LED strings in a dynamic phototherapy system at the system's maximum synthesized frequency.

Asynchronous operation is similar to latched mode except that the counter's count must be reset each time the data registers are loaded by the SPI bus. Without the frequencies limitation of data updates, the maximum frequency that can be algorithmically synthesized by the system of FIG. 12 is practically limited to waveform 247, having a frequency equal to one-half that of the rate of clock Clk θ, as shown in FIG. 15C. For example if Clock 180 is operating at a frequency of $f_\theta=1/T_\theta$, then the limit of the synthesized frequency is then limited to $$f_{synth}\leq 0.5 f_\theta=1/2T_\theta$$

For example, a 2 MHz can generate a synthesized pulse frequency of 1 MHz as shown in waveform 247, switching at time $t_1$ from an array of LEDs with $\lambda_2$ wavelengths to an array of LEDs with $\lambda_1$ wavelengths without interruption. Such rapid changes are made possible by the high bandwidth capability of the SPI bus, able to send data at a clock rate of 10 MHz or 0.1 μsec. The clock period of a 2 MHz clock is $T_\theta=0.5$ MHz, five times slower than the SPI bus. Ideally for operation at such high rates the counters could be redesigned to "set and forget," meaning that once the condition is written into the counter, it keeps resetting and restarting after each clock cycle is completed. But as any synthesized frequency approaches the clock frequency only 50% is possible with any degree of consistency.

Figure 15D:
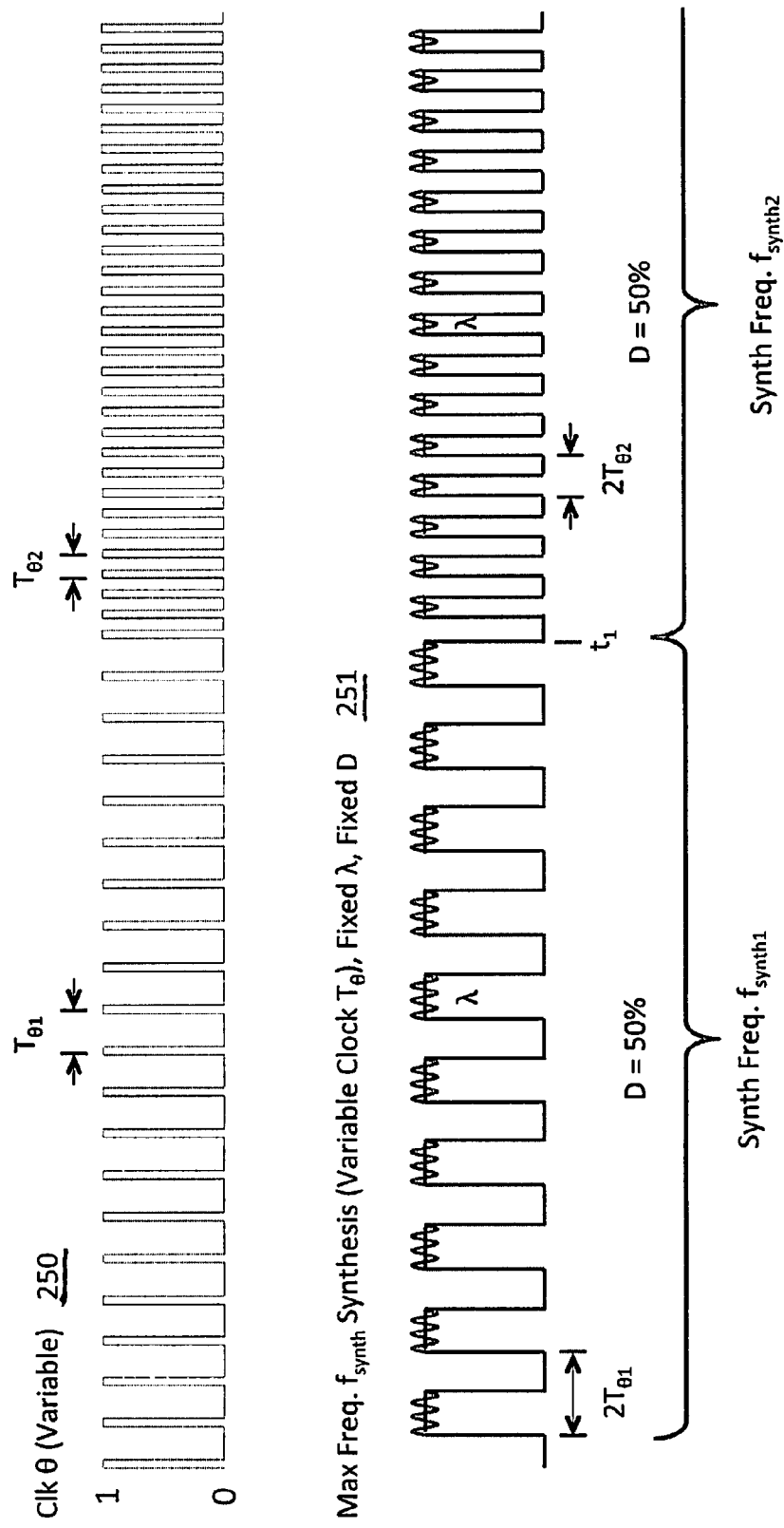
FIG. 15D is a timing diagram of an alternative method of synthesizing high frequencies in dynamic phototherapy system using a variable clock signal.

It should be noted that at this time there is no known reason to synthesize photoexcitation frequencies above a few kilohertz. Nonetheless waveform 180 represents the upper end in the range of frequency synthesis using the described hardware. Power dissipation at the maximum clock rate however can be significant Under normal operation, synthesis of lower frequencies doesn't require such a fast clock continuously. Switching the clock to a high frequency only when required as shown at time $t_1$ in waveform 251 of FIG. 15D saves power except when the performance is needed. The same dynamic frequency switching of Clk θ can be used whenever high frequency waveforms must be synthesized, and a slower clock rate for Clk θ employed under normal circumstances.

While such methods are important in extending operation of a phototherapy apparatus to the highest possible frequencies, synthesizing extremely low frequencies using purely hardware implementations can likewise be problematic, requiring counters with a high number of bits consuming large silicon areas.

Figure 15E:
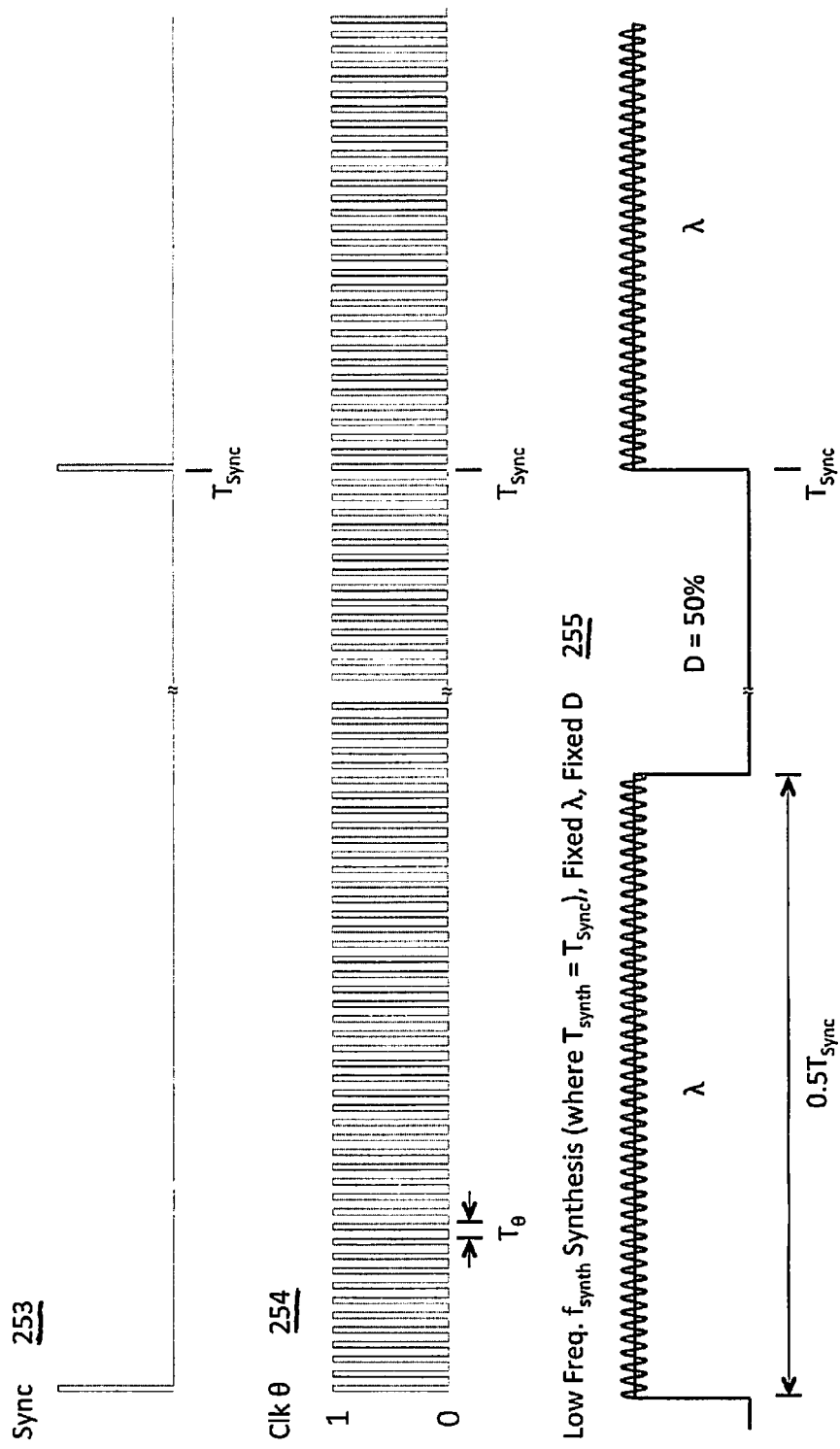
FIG. 15E is a timing diagram for synthesizing frequencies in a dynamic phototherapy system equal to a $V_{sync}$ frequency.
Figure 15F:
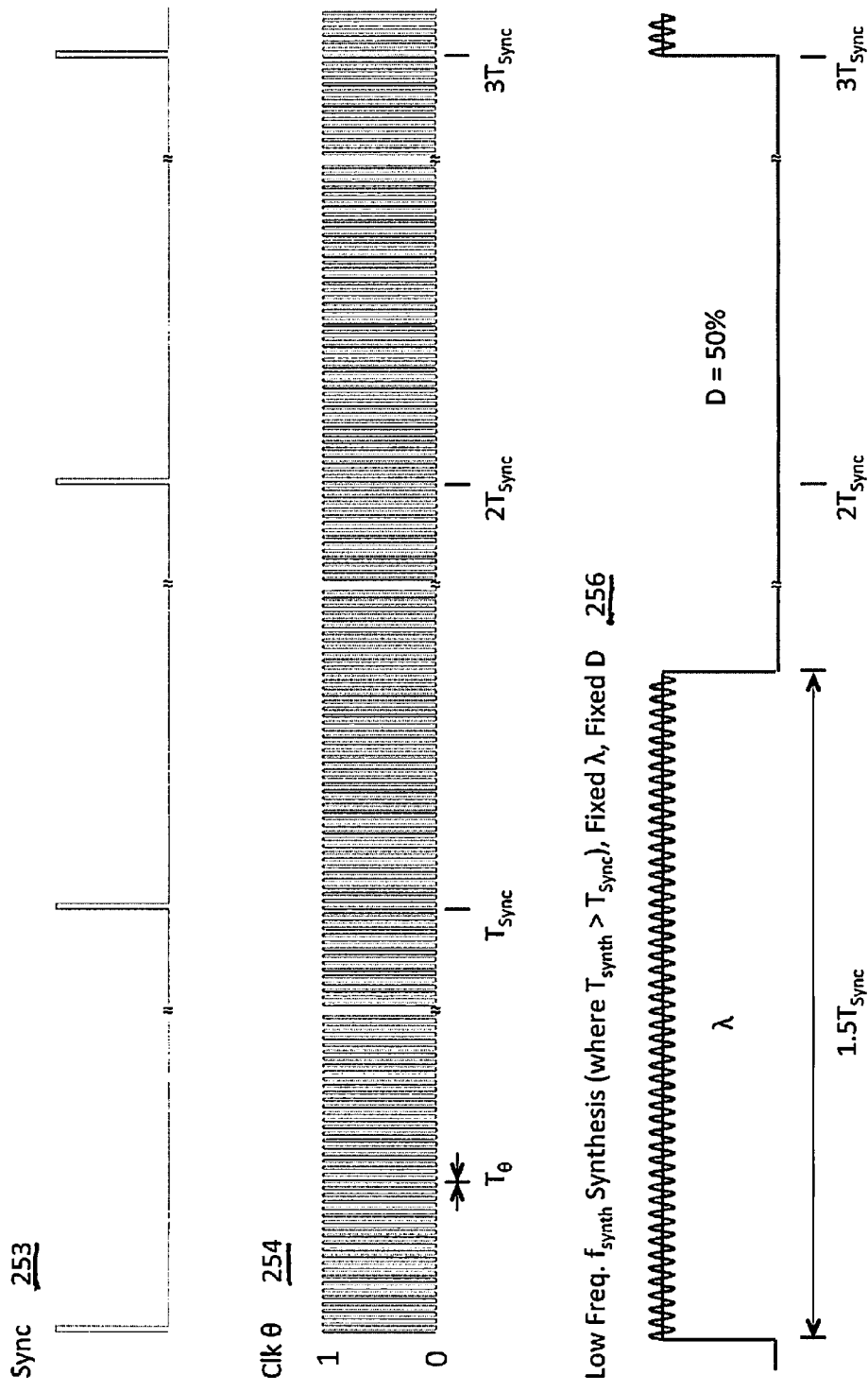
FIG. 15F is a timing diagram for synthesizing frequencies in a dynamic phototherapy system lower than a $V_{sync}$ frequency.

The practical limit of the LED driver IC by itself is set by the counter size. A 12-bit counter has a maximum duration of $T_{cntr}=4096\cdot T_\theta$. In the earlier case, where the clock period $T_\theta=107$ μsec, the maximum duration is 438 msec corresponding to a synthesized waveform having a frequency n lower than $f_{synth}\leq 2.28$ Hz. As shown in FIG. 15E, this approach entails running the counter to its full count. As such the $T_{sync}$ period is set equal to the maximum clock count. By utilizing the microcontroller to rewrite and retrigger the counter many times, any low frequency can be produced. In the example shown in FIG. 15F, Clk 254 along with Sync pulse 253, retriggers the counter three times resulting in low frequency waveform 256 having an on time of 1.5T=657 msec, a period of 1,314 msec, and a corresponding digital pulse frequency 0.76 Hz. By combining firmware or software control in the microcontroller with hardware counters in the LED driver ICs, any low or extremely low wavelength frequency can be generated, even at frequencies my lower than that produced by the full count of the counters used within the LED driver ICs.

In conclusion, waveform synthesis for LED phototherapy using LED driver ICs combined with microcontroller originally intended exclusively for TV backlighting offers a flexible means by which to synthesize varying frequencies and patterns needed for photoexcitation and sequencing of multiple wavelength LEDs. Unlike in HDTVs, where the duty factor varies and the Vsync period remains constant, in the disclosed phototherapy device, LED on-time $t_{on}$, the period $T_{sync}$ of the Sync pulse and the frequency of Clock θ, both generated by microcontroller 209, can vary dynamically, changing the clock rates either continuously or each time a new Sync pulse occurs. Implementing an LED drive system with a varying time base and time varying Sync pulses is completely contrary to mandating the use of fixed rate Vsync pulse rates in HDTVs conforming to international video broadcast standards and complying with government communication regulations. So while phototherapy can employ dynamic clock methods (similar to computer cores), video systems cannot.

Programmable Brightness Control

Like backlighting in HDTVs, the LEDs in a phototherapy LED pad likewise require brightness control. While TV backlighting systems perform duty factor based PWM brightness control using a fixed frequency coming from the TV's vertical sync signal, and utilize the full 12-bit counter for precision dimming and phase delay control, LED drive in phototherapy is not based on fixed frequency dimming, but instead must synthesize waveforms having both programmable frequency and dimming control too.

Unlike in TV backlighting, the duty factor is not the value of clock pulses residing in the individual channel's $t_{on}$ register divided by the full count of 4096, but instead must be calculated for each synthesized frequency. This task is performed algorithmically within microcontroller 209 interfaced to the LED driver IC 207 through SPI bus 213. The algorithm for these calculations is described later in this disclosure.

Figure 17A:
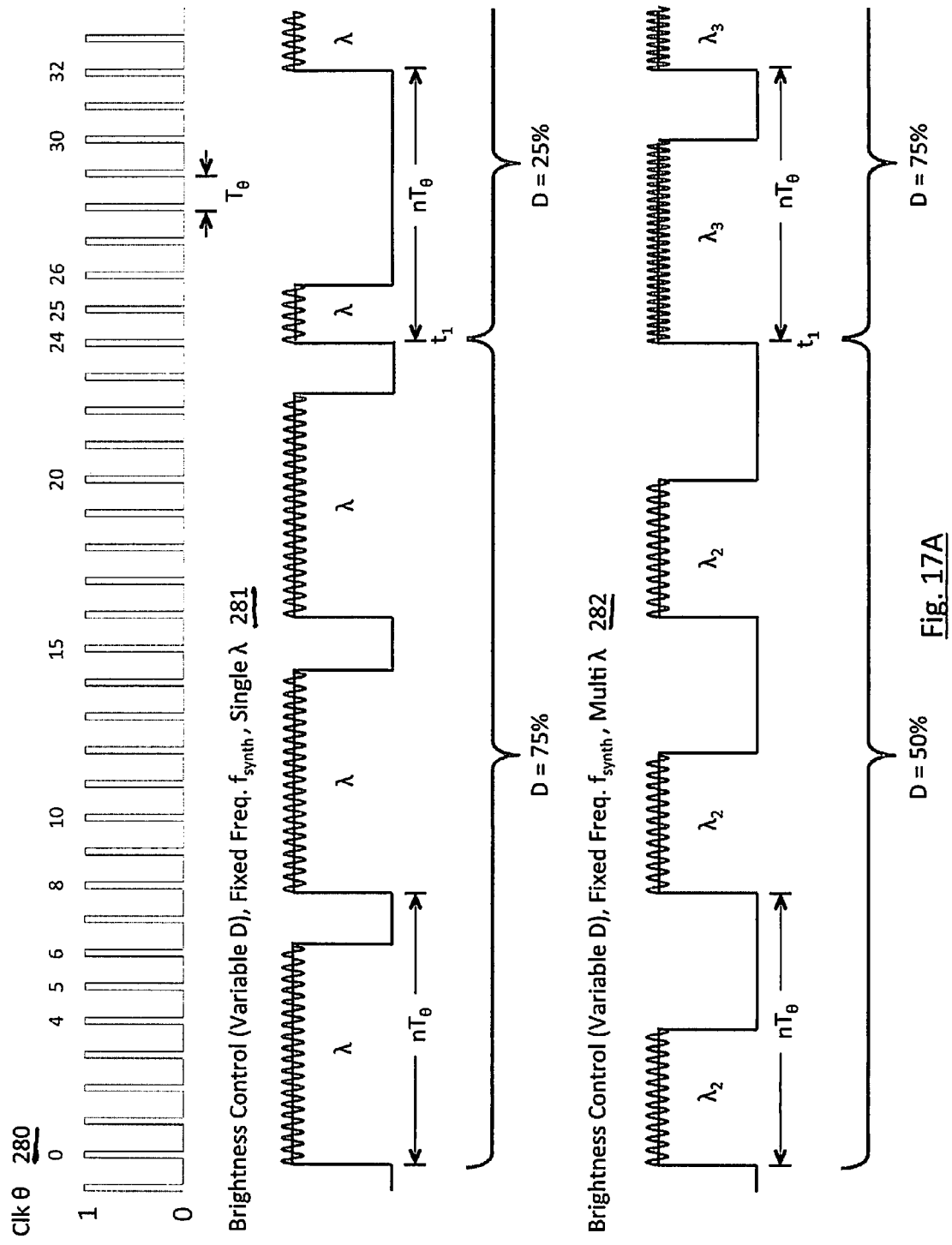
FIG. 17A is a timing diagram for synthesizing fixed frequencies in a multi-wavelength dynamic phototherapy system with PWM brightness control

FIG. 17A illustrates examples of fixed frequency PWM dimming. In the examples shown, the clock period is a fixed value of $nT_θ$ (shown for convenience as n=8), but in practice the count "n" implemented in microcontroller 209 may be much larger. In waveform 281, an array of LEDs having wavelength λ is illuminated 6 out of 8 clock pulses having a synthesized duty factor and corresponding PWM controlled brightness of D=6/8=75%. The frequency of the synthesized waveform fsynth=1/nT$_θ$ is programmed to a prescribed value using the techniques described in the prior section. At time t1, the microprocessor changes the value of ton from 8 to 2 pulses resulting in a change to the synthesized duty factor to D=2/8=25%.

In the example waveform 282, at time $t_1$ both the duty factor controlled PWM brightness and the LED wavelengths are changed. Prior to the transition an array of LEDs having wavelengths $λ_2$ are illuminated with an on-time of 4 pulses for a resulting duty factor and PWM brightness of D=4/8=50%. After time $t_1$, the LED array changed to LEDs having a wavelength $λ_3$ and a PWM controlled brightness of D=6/8=75%.

Figure 17B:
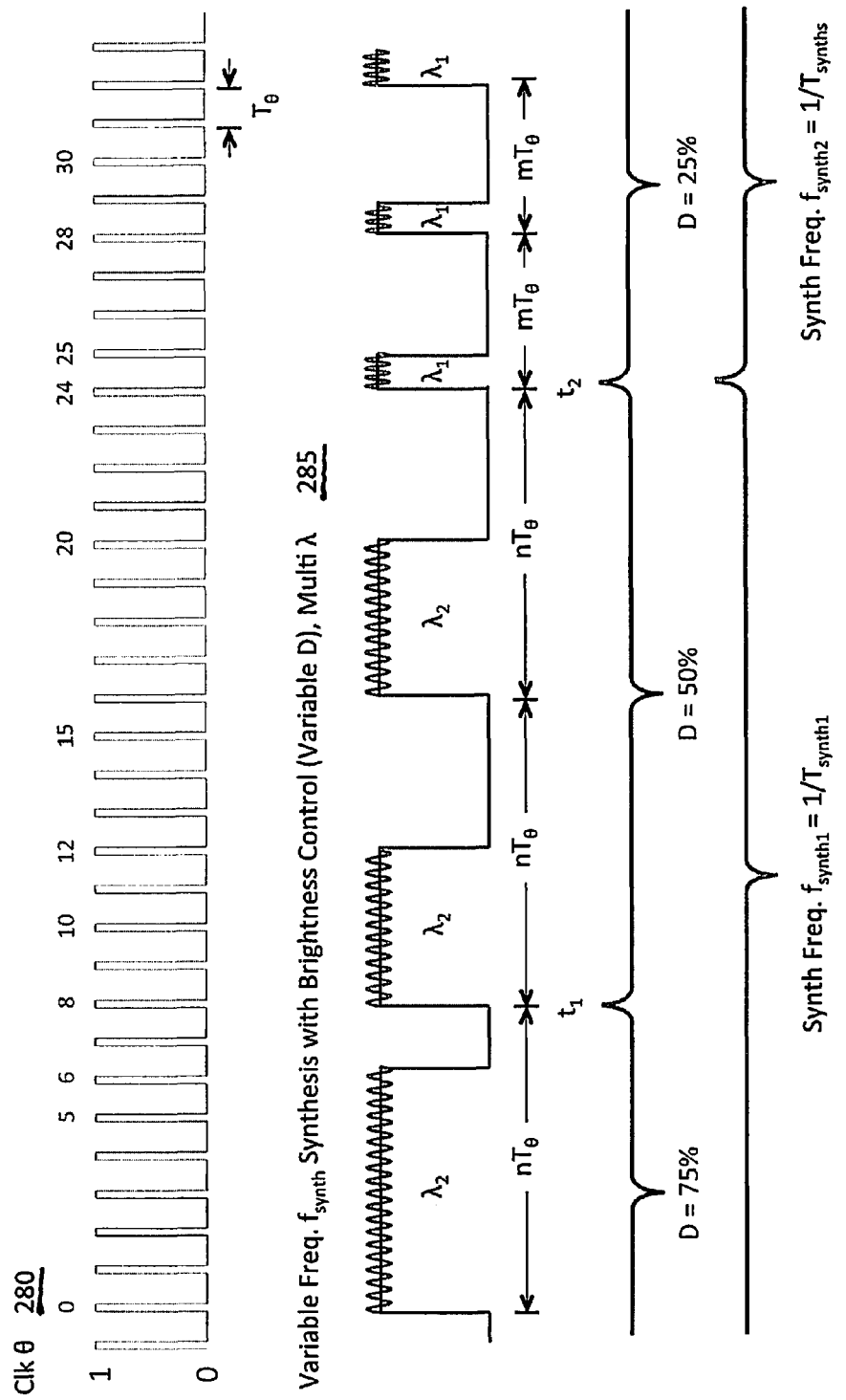
FIG. 17B is a timing diagram for synthesizing multiple frequencies in multi-wavelength dynamic phototherapy system with PWM brightness control.

In waveform 285 of FIG. 17B, the PWM brightness, synthesized frequencies, and LED wavelengths are all changing. Prior to time $t_1$, an array of LEDs having wavelength $λ_2$ is illuminated with an on-time $t_{on}$ (by example with $t_{on}$=6 pulses) and a synthesized period $T_{synth1}$=nT$_θ$ (by example where n=8 pulses) corresponding to a duty factor D=6/8=75%. At time $t_1$, the same array of LEDs with wavelength $λ_2$ changes to $t_{on}$=4 pulses corresponding to a duty factor of 50%. At time $t_2$, the array of LEDs with wavelength $λ_2$ is shut off and an array of LEDs with wavelength $λ_3$ is turned on with a new on-time $t_{on}$ (by example where $t_{on}$=1 pulse) and a new period $T_{synth2}$=mT$_θ$ (by example where n=4 pulses). The result is a new synthesized frequency twice that of the prior frequency, i.e. where $f_{synth2}=2f_{synth1}$ and where D=25%.

In the above description, the duty factor control setting PWM brightness level of an array of LEDs is achieved by adjusting the on time $t_{on}$ for any given synthesized frequency $f_{synth}$ and corresponding period $T_{synth}$, as given by the relation $$D=t_{on}/T_{synth}=t_{on}f_{synth}$$

In practice, one fixed frequency waveform is synthesized for an extended duration Δt, typically from minutes to tens of minutes.

In an alternate embodiment, the synthesized period $T_{synth}=t_{on}+t_{off}$ varies for each and every pulse. The result is a continually varying frequency spectrum. Examples of algorithms for such variable frequency operation include constant on-time variable frequency operation, constant off-time variable frequency operation, constant duty factor variable frequency operation, and swept frequency operation.

Figure 17C:
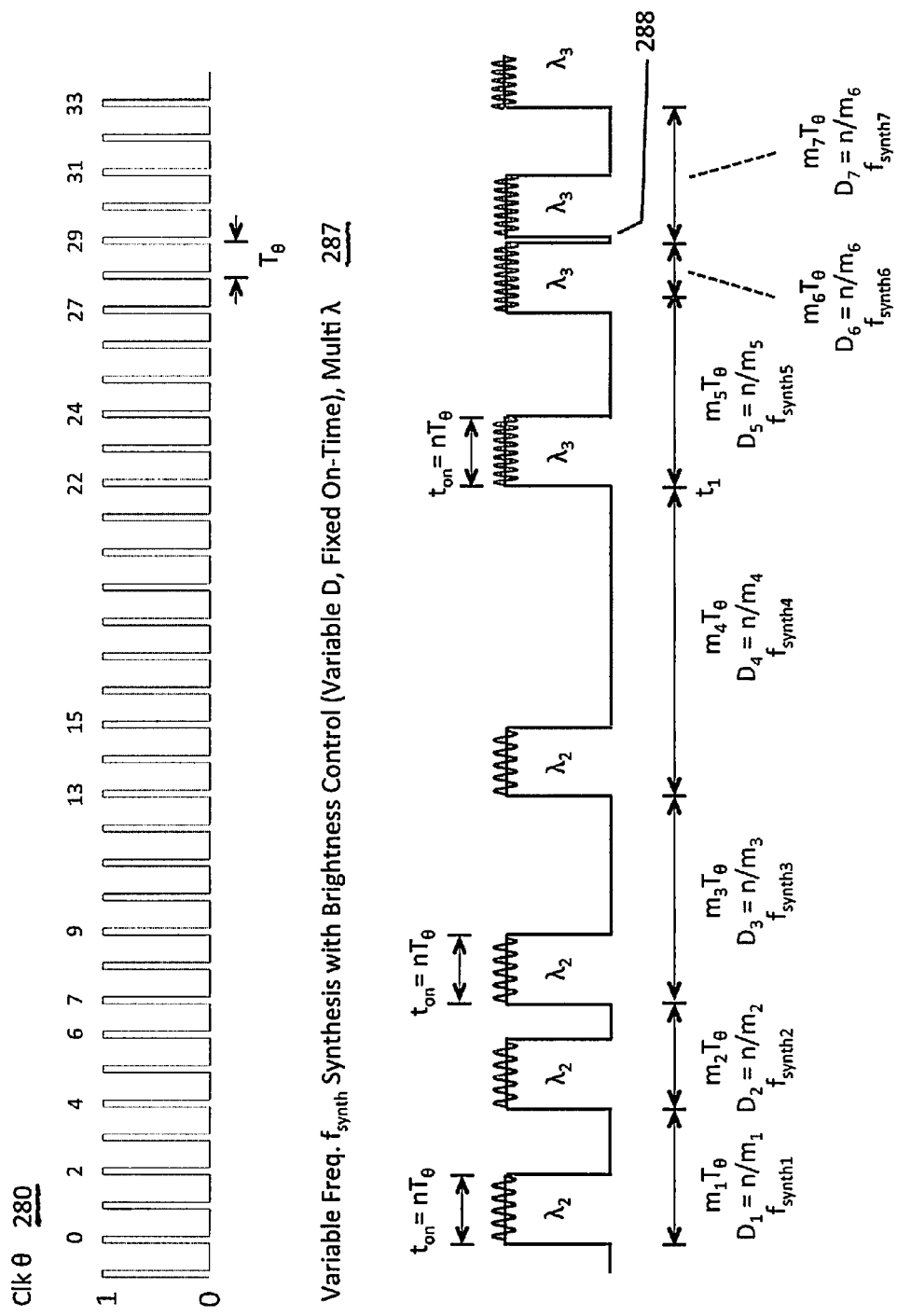
FIG. 17C is a timing diagram for synthesizing dynamically varying frequencies in multi-wavelength dynamic phototherapy system with constant on-time brightness control

In the case of constant on-time variable frequency synthesis shown in FIG. 17C, a desired spectrum of frequencies is generated under microcontroller control having a fixed and constant on-time $t_{on}$ and a constantly varying off time $t_{off}$, duty factor D, period $T_{synth}$ and with a corresponding frequency $f_{synth}$ as given by the relation $$T_{synth}=1/f_{synth}=t_{on(constant)}+t_{off(variable)}$$

where $t_{on(constant)}$ is set to a fixed interval (having by example duration $t_{on(constant)}$=2 pulses as shown), and having a value $t_{off(variable)}$ constantly being varied. As $t_{off}$ varies so too does $T_{synth}$ and duty factor $D=t_{on}/(t_{on}+t_{off})$. A series of pulses with off periods ranging from 1 to 7 clock intervals is shown and the resulting equivalent synthesized frequency and duty factor as summarized in Table 2. For illustrative purposes, the synthesized frequency $f_{synth}$ depends also depends on the frequency of Clk θ, illustrated for fixed frequency values of 9,346 Hz (with corresponding clock period $T_θ$=107 μs) and 935 Hz (with corresponding clock period $T_θ$=1070 μs).

TABLE 2

| | Constant on-time variable frequency method | | | | | | |
|---|---|---|---|---|---|---|---|
| Pulse # | Wavelength LED | $t_{on}$ Clk θ | $t_{off}$ Clk θ | $T_{synth}$ Clk θ (μs) | D = $t_{on}/T_{synth}$ | $f_{synth}$ (Hz) $T_θ$ = 9,346 Hz | $f_{synth}$ (Hz) $T_θ$ = 935 Hz |
| 1 | $λ_2$ | 2 | 2 | 4 (428) | 50 | 2,336 | 234 |

TABLE 2-continued

Constant on-time variable frequency method

| Pulse # | Wavelength LED | $t_{on}$ Clk θ | $t_{off}$ Clk θ | $T_{synth}$ Clk θ (μs) | D = $t_{on}/T_{synth}$ | $f_{synth}$ (Hz) $T_θ$ = 9,346 Hz | $f_{synth}$ (Hz) $T_θ$ = 935 Hz |
|---|---|---|---|---|---|---|---|
| 2 | $λ_2$ | 2 | 1 | 3 (321) | 67 | 3,115 | 312 |
| 3 | $λ_2$ | 2 | 4 | 6 (642) | 33 | 1,558 | 156 |
| 4 | $λ_2$ | 2 | 7 | 9 (963) | 22 | 1,038 | 104 |
| 5 | $λ_3$ | 2 | 3 | 5 (535) | 40 | 1,869 | 187 |
| 6 | $λ_3$ | 2 | 0 | 2 (214) | 100 | 4,673 | 467 |
| 7 | $λ_3$ | 2 | 2 | 4 (428) | 50 | 2,336 | 234 |

As shown, the $6^{th}$ pulse is programmed for 100% duty factor, i.e. $t_{off}$=0. The ability to achieve a zero off time pulse depends on the LED driver IC and the frequency of operation. In some cases, the LEDs will remain on for the entire period $T_{synth}$ but may thereafter try to turn off. Due to the finite transition time required to turn the current source off and back on a small off interval or "glitch" 288 unrelated to the clock period $T_θ$ may result. The impact of this glitch is to slightly shorten the on time of the subsequent pulse, meaning the duty factor of the $7^{th}$ pulse will be slightly reduced from the 50% shown in the table. If however, the glitch does not occur, the $6^{th}$ pulse will merge with the on portion of the $7^{th}$ pulse, resulting in a 4-pulse on-time as a 2-pulse off-time. The hybrid mix of the $6^{th}$ and $7^{th}$ pulses results in a 6-clock pulse period with a duty factor D=4/6=66%.

Constant off-time LED drive algorithms are similar to the above table except that the data in the $t_{on}$ and $t_{off}$ columns are switched. In LED drive, the result of constant on time and constant off-time variable frequency LED drive algorithms is that the synthesized photoexcitation frequency $f_{synth}$ and the PWM brightness of the LED arrays are proportional with a fixed ratio. In constant duty factor variable frequency drive, the on time scales with frequency to maintain a constant duty factor so that the frequency varies but the brightness doesn't. In general, constant brightness is more useful in LED drive than continuously varying the brightness.

Another possible variable frequency algorithm is swept frequency operation, where the frequency increases or decreases monotonically during operation, e.g. starting at 10 kHz and sweeping down to 10 Hz over an interval of minutes to tens of minutes, or alternatively starting at 5 Hz and sweeping up to 5,000 Hz over an interval of minutes to tens of minutes. Again holding the brightness constant (adjusting the on-time to maintain a fixed duty factor and PWM brightness) is generally preferable to varying the LED brightness.

Figure 18:
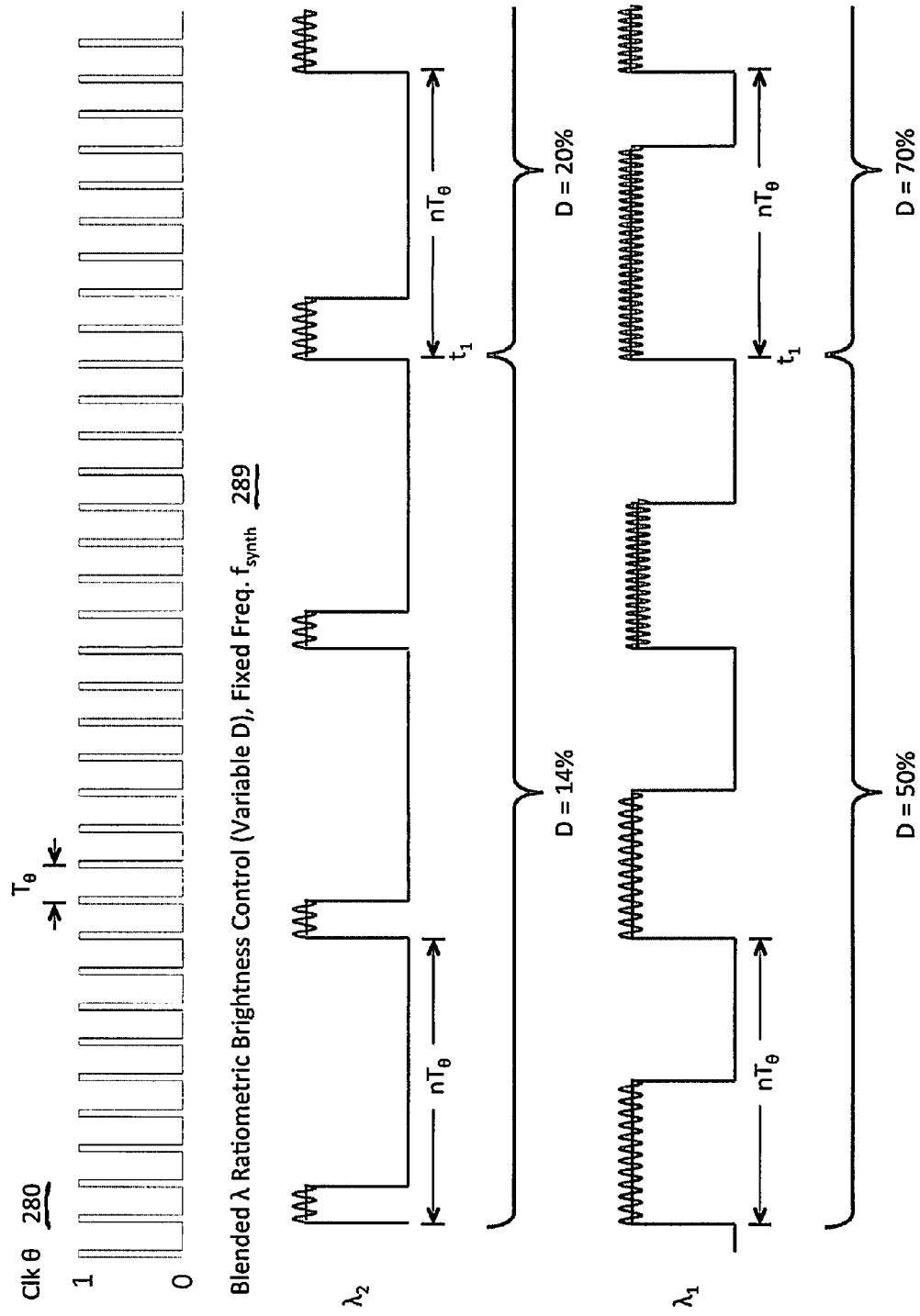
FIG. 18 is a timing diagram for parallel driven multi-wavelength LED strings with independent PWM brightness control (blending) in a dynamic phototherapy system with fixed frequency synthesis.

Finally LED current using PWM brightness and duty factor control can be used to blend LEDs of different wavelengths controlling their mix, i.e. their "blend" by their relative brightness. For example, in FIG. 18, an array of LEDs having a wavelength $λ_2$ is illuminated to a PWM-controlled brightness 28% that of an array of LEDs having a wavelength $λ_1$. In the example of concurrently illuminated waveforms 289, prior to time $t_1$, the LED array having wavelength $λ_2$ are driven with a PWM duty factor of 50%, while the array of LEDs with wavelength $λ_2$ are driven at a PWM brightness of 14%, i.e. at a brightness 28% of the concurrently illuminated LEDs. After time $t_1$, the LED array having wavelength $λ_1$ are driven with a PWM duty factor of 70%, while the array of LEDs with wavelength $λ_2$ are driven at a PWM brightness of 20%. Despite changing the overall LED brightness, the ratio of the brightness of the $λ_2$ wavelength LEDs to that of the $λ_1$ wavelength LEDs remains at 28%.

LED Current Control

Although LED current control can be used to control LED brightness, the quantum efficiency of LEDs varies with current producing more heat and less photons per power consumed at higher currents. For that and for safety reasons the current of LEDs should in general be biased to moderate levels, e.g. 20 to 30 mA each, depending on the LED's construction. Another reason to employ LEDs running at more moderate currents is that high-current high-brightness LEDs are substantially more expensive in the market and have fewer suppliers supporting their manufacture. In phototherapy applications, concentrating high-brightness light into a small area makes it more difficult to obtain a uniform light intensity over a large area such as the entirety of a LED pad than using a higher density of LEDs with lower brightness levels.

Even though dynamic brightness control may be achieved by PWM dimming rather than adjusting LED current, LED current remains important in obtaining good brightness uniformity across an LED pad. In FIG. 12 (with one channel shown by example shown in inset 300 of FIG. 19) each channel comprises a precision gate bias and control circuit 215a through 215n controlling a corresponding current sink MOSFET 216a through 216n and LED string 205a through 205n. The current passing through each MOSFET is monitored by the precision gate bias circuit and compared to a reference current $αI_{ref}$. Any error between the reference current and a ratio equivalent of the measured LED current results in a dynamic adjustment of gate bias higher or lower in voltage until the two currents match. Because the LED current is mirrored and trimmed for accuracy using a low voltage current sink or a operational amplifier, the actual reference current need only comprise a fraction of the LEDs' currents $I_{LEDa}$ through $I_{LEDn}$ but for simplicity's sake we will treat the reference current as though it has the same magnitude, i.e. where $I_{LED}(max)=I_{ref}$.

This maximum LED current in each channel of LED driver IC 207 is set by the value of $I_{ref}$, and in most cases set only once for each multichannel LED driver IC by a single external precision resistor $R_{set}$ and a common precision voltage reference $V_{ref}$. To guarantee superior channel-to-channel matching, the precision voltage $V_{ref}$ is shared by all the channels (and preferably by all LED driver ICs). The maximum LED current is set by the resistor value when the digital multiplier α=100% (set by the digital data register $I_{LED}$ through the SPI bus) and is given by the relation $$I_{LED}(max)=αI_{ref}$$

where $$I_{ref}=k(V_{ref}/R_{set})$$

Figure 19:
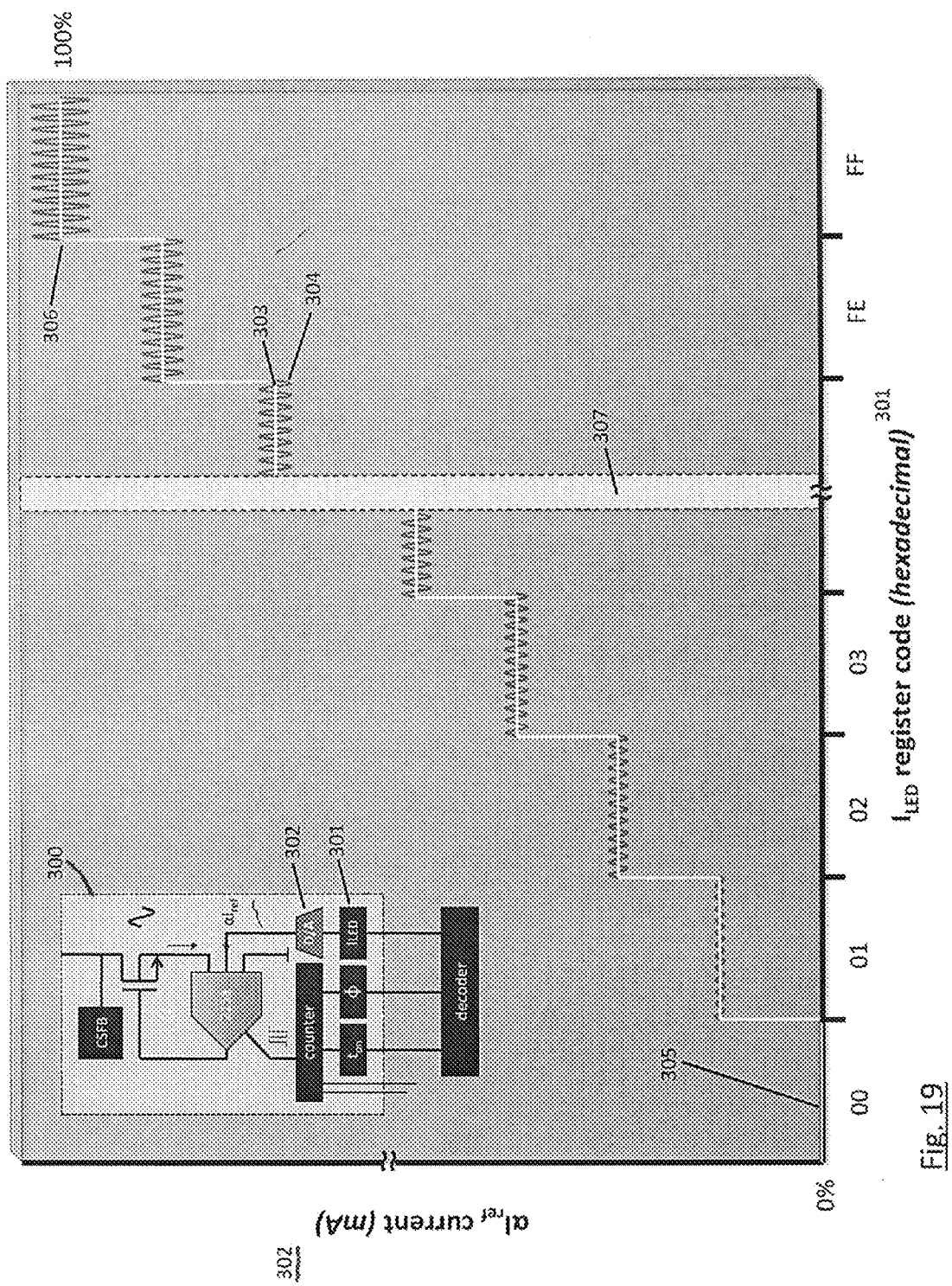
FIG. 19 is a graph of the current in an LED string as a function of the data stored in an $I_{LED}$ register in a dynamic phototherapy system using a programmable D/A converter.

For safety, this value can be set to an $I_{LED}$(max) current value for the maximum brightness that conforms to international and governmental health and safety standards. The maximum value occurs whenever the $I_{LED}$ register 301 is set to a value whereby where $\alpha$=100%. The relationship between the digital register-code loaded in $I_{LED}$ data register 301 and the analog value $\alpha I_{ref}$ output from D/A converter 302 is illustrated in the graph of FIG. 19. Assuming D/A converter 302 comprises an 8-bit digital to-analog converter circuit, then the channel current $\alpha I_{ref}$ can be controlled into 256 levels from 0 mA (off) to 100%·$I_{ref}$ in 0.39% steps.

In digital programming a 8-bit or 1-Byte word can be represented by two hexadecimal characters ranging from a hexadecimal code 00 representing the $1^{st}$ step 305 has a value $\alpha I_{ref}$=0 while a hexadecimal code FF representing the $255^{th}$ step 306 has a value $\alpha I_{ref}$=100%·$I_{ref}$. The following equation converts a hexadecimal number into its decimal equivalent:

$$\text{Decimal} = (\text{Hex}_1 \cdot 16 + \text{Hex}_0)$$

So to convert hexadecimal FF Into its decimal representation (where F is equal to 15) is given by (15·16)+15=255 or 100%. Although any mathematical transfer function can be represented, for simplicity's sake let us assume a linear relation, $I_{LEDn}$=[(Hex$_1$·16+Hex$_0$)/255]·$I_{ref}$ where the code for hexadecimal 80 or decimal step 8·15+0=128 represents the value (128/255)·$I_{ref}$ or roughly 50% of the peak current.

Intentionally, most current step increments have been hidden (they lie in the gap 307) from the graph of FIG. 19 for clarity's sake. For those current step increments that are shown, each step includes the constant value of current 303 and an analog representation of the light wave output 304 from the LEDs (similar to the composite signal representation described previously in FIG. 10C). Notice that as the current increases the magnitude of the sine wave representing the light output increases in amplitude.

In another embodiment of this invention, programmable registers within microcontroller-209 limit the current $\alpha I_{ref}$ set by A/D converter 302 to preprogrammed maximum values by restricting the allowed $I_{LED}$ register code by login privilege or security code. In the phototherapy apparatus disclosed herein, user login or security codes established during manufacturing or setup, restrict the machine's high power operating modes to skilled physicians or approved technicians. For example, while a clinician may be restricted to operating the machine up to a maximum brightness of 50% or Hex 80, a practicing physician may be authorized to operate the machine up to an $I_{LED}$ register code of hex E4 or in decimal to (14·16+4)/255=89%.

This means a physician can operate the apparatus to a setting 89% of the maximum brightness while other users are limited to 50% of the maximum brightness. In the worst case, should the machine malfunction, the maximum possible brightness set by the value of resistor permanently soldered into the circuit during manufacturing is still limited to a level defined as "safe" from regulatory agencies.

Figure 20:
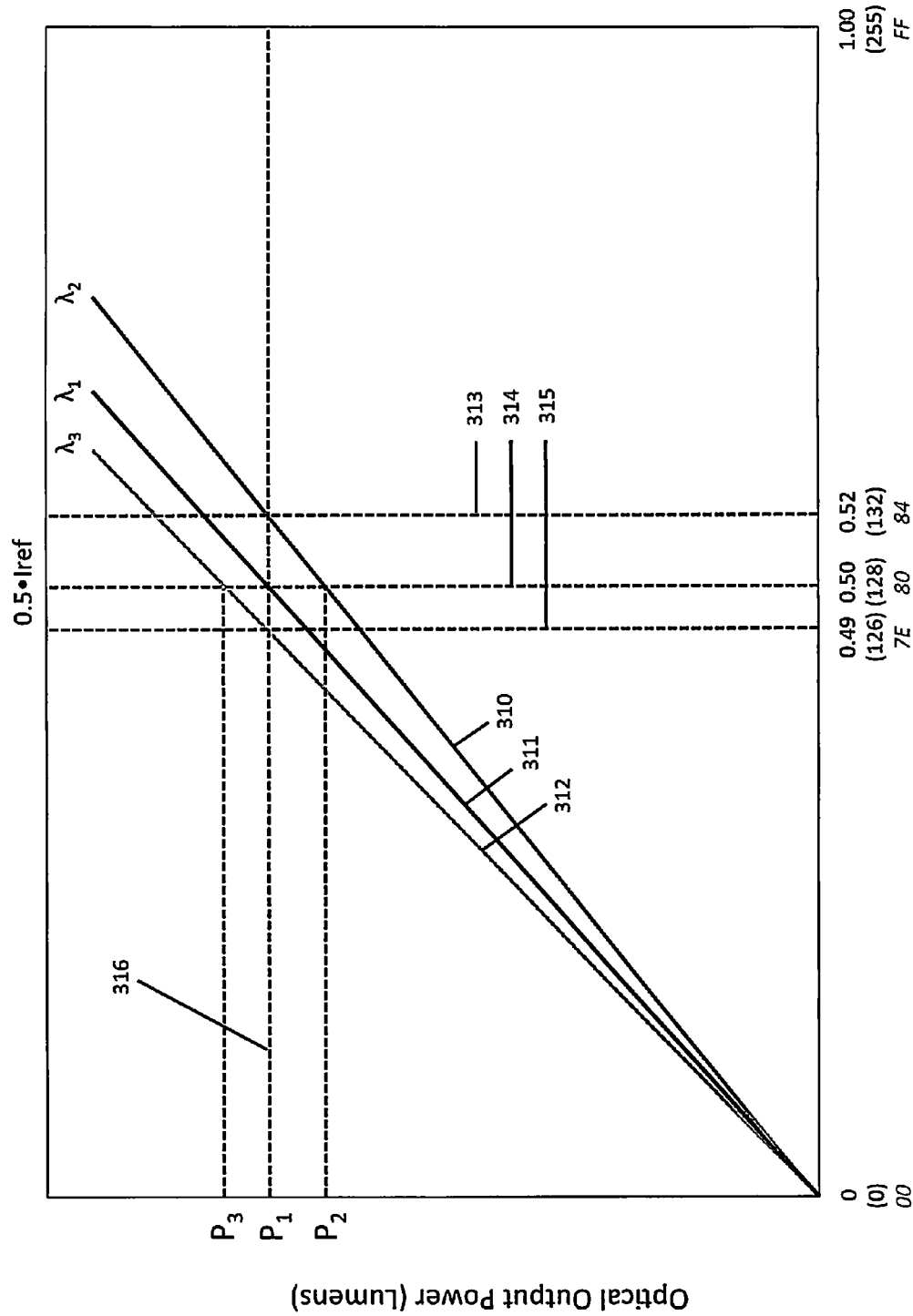
FIG. 20 is a graph of optical output power at different wavelengths as a function of data stored in an $I_{LED}$ register, illustrating brightness compensation.

Aside from enabling security and safety features the other benefit of programmable $I_{LED}$ register 301 is to compensate for non-uniformities in LED brightness. Inconsistent brightness in LEDs results from manufacturing variations, from crystalline defects in LEDs, by mixing different manufacturer's devices into the same phototherapy apparatus, or by simultaneously driving LED strings having different wavelengths. FIG. 20 illustrates the optical output power of an LED versus its current, here represented by the corresponding values of $\alpha$ in percentage, and by the digital and hexadecimal code in $I_{LED}$ data register.

As shown three LEDs 310, 311, and 312 operating at a nominal current of 0.5·$I_{ref}$ as programmed by hex code 80 (128 decimal equivalent) in the $I_{LED}$ data register exhibit three optical power outs $P_2$, $P_1$ and $P_3$ respectively. These variations may occur as a result of natural stochastic variability in LED manufacture or because the LED strings represent arrays of LEDs having differing wavelengths $\lambda$. In the event that the LEDs have different wavelengths, the channel driver's CSFB circuit compensates for variation in the LEDs' forward voltages. The difference in brightness is therefore not related to forward voltage but simply the current dependence of LED brightness.

Regardless of the mechanism, if the LED array is intended to exhibit a uniform power output $P_1$ across the LED pad's surface, LEDs 310 and 312 must be driven under different current conditions to achieve the same optical power output as LED 311. Since the on-time and clock periods are employed algorithmically to determine an LED's PWM controlled brightness D and synthesized frequency $f_{synth1}$, it is preferable not to complicate the PWM control function to compensate for mismatched LED brightness. Instead, the mismatch can be compensated for using the $I_{LED}$ setting once during manufacture and can be ignored thereafter. If for example LED 310 has its current changed from the nominal value of hex 80 to hex 84 (decimal 132), the LED's current increases to 0.52·$I_{ref}$ and as a result, the LED optical output increases from $P_2$ to $P_1$ as desired. Similarly if LED 312 has its current changed from the nominal value of hex 80 to hex 7E (decimal 126), the LED's current decreases to 0.49·$I_{ref}$ and as a result, the LED optical output decreases from $P_3$ to $P_1$ as desired.

Figure 21:
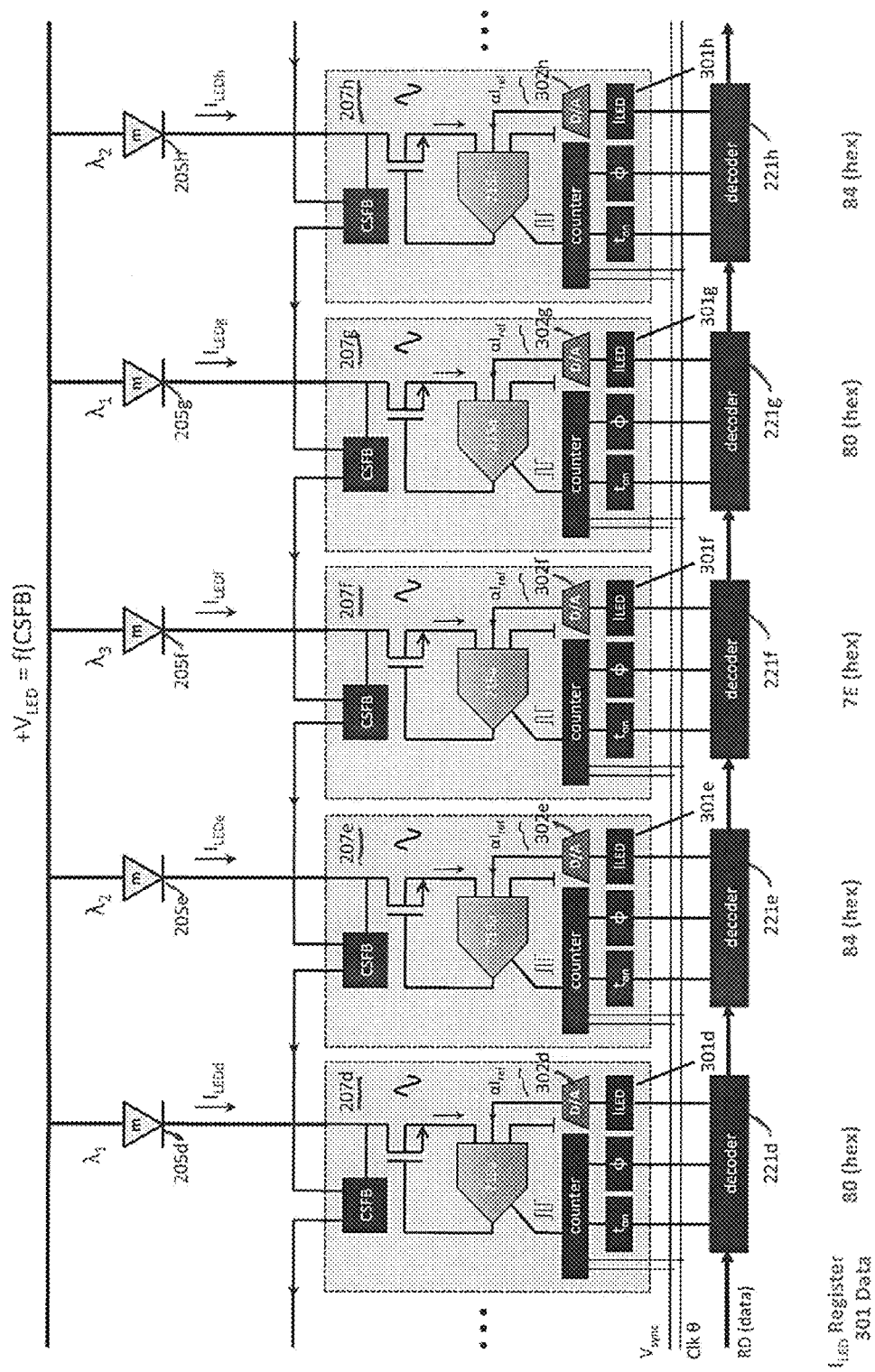
FIG. 21 is a circuit diagram illustrating the loading of $I_{LED}$ register data for brightness compensation.

By storing the hexadecimal values of $I_{LED}$ for LEDs 310, 311, and 312 permanently in nonvolatile memory within the microcontroller 209, broadcasting the LED current settings (hex 84, hex 80, and hex 7E respectively) over the SPI bus and loading them into their corresponding $I_{LED}$ registers within the channel drivers 207a through 207n at startup as shown by the $I_{LED}$ data registers 301d through 301h in FIG. 21, dissimilar LEDs can be biased to the same brightness despite their manufacturing differences. The $I_{LED}$ values stored in the microcontroller then serve as a type of compensation or correction table for LED brightness.

Phase Delay

As shown previously, waveform synthesis combining microcontroller 209 with LED driver IC 207 is capable of driving arrays of varying wavelength LEDs in flexible sequences, user defined photoexcitation frequencies $f_{synth}$, and varying levels of PWM brightness. It was also shown while the phase delay $\Phi$ can be employed in the waveform synthesis process, the judicious use of $t_{on}$ along with Clk $\theta$ and Sync signals can produce all the desired waveforms needed for a phototherapy apparatus without using phase delay $\Phi$ for such tasks. As such, phase delay $\Phi$ remains available for implementing other important features.

Figure 22:
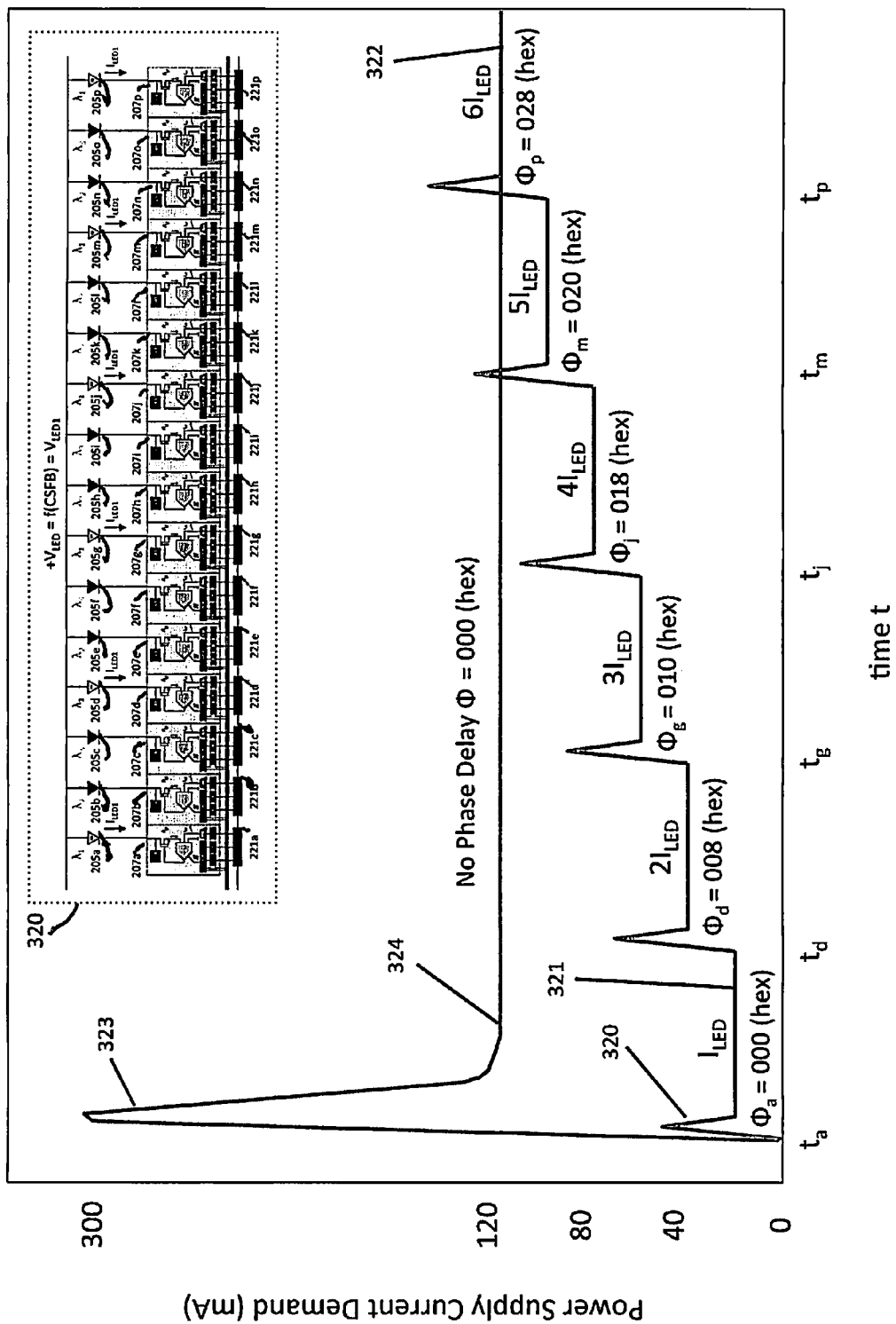
FIG. 22 is a graph of the turn-on current transient waveform, illustrating the benefit of phase delay.

Once such notable feature is shown in the graph of FIG. 22 where the current demand drawn by the multiple channels of an LED driver (see multichannel LED driver example in inset 320) is plotted against elapsed time during startup of the system. In curve 324, a phototherapy apparatus with no channel delay is started at time $t_a$ comprising an array of LEDs of a particular wavelength all turned on at once and conducting (while other wavelength LEDs remain off). The result is a current spike 323 which can reach peak currents more than double or triple the normal steady current consumption 322 of the system.

If instead of turning all the channels on at one time the LED array is turned on with a programmable phase delay, the channels commence conducting in a sequence so they don't all try to conduct at once, greatly diminishing the turn on current spike. For example, by only turning on one string of LEDs at time $t_a$ with no phase delay (i.e. where phase delay Φ=000 hex), the inrush current is changed from curve 323 with a peak current of 300 mA to that of curve 320 having a peak inrush current of 40 mA, improving the inrush current by better than a factor of 7×.

After the inrush the current stabilizes to current 321 representing the steady state conduction of one LED string, a second string of LEDs with phase delay Φ=008 hex then turns on after 8 pulses at time $t_d$ followed by a third string with phase delay Φ=010 hex turning on after another 8 pulses at time $t_g$, followed in succession by a fourth, fifth, and sixth string with phase delays Φ=018 hex, 020 hex, and 028 hex, each turning on in 8 pulse increments at times $t_l$, $t_m$, and $t_p$ respectively. As a result the peak current only slightly exceeds the steady state LED current 322 or 120 mA. As a result, the inrush current is held below half of the spike current 323 conducted during turn on without the phase delay feature.

Microcontroller and Waveform Synthesis Algorithm

Figure 23A:
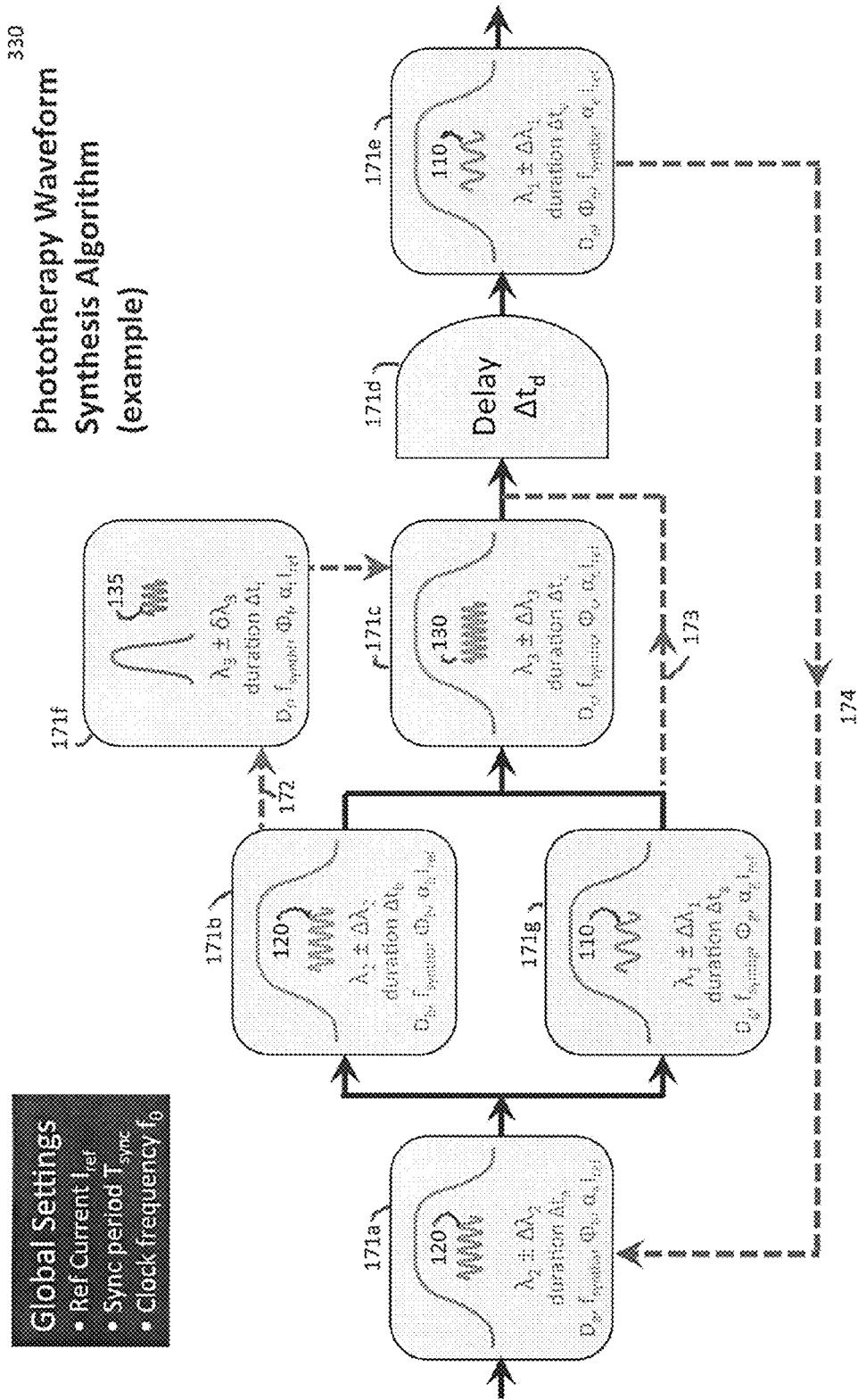
FIG. 23A is a flow chart of an exemplary dynamic phototherapy protocol illustrating full parametric control of the duty factor D, the synthesis frequency $f_{synth}$, the phase delay φ, and the reference current multiplier α.

FIG. 23A represents an exemplary phototherapy waveform synthesis algorithm of the disclosed method and apparatus. The algorithm is not intended to suggest a specific sequence or therapy but rather to combine by way of example many of the previously defined operational elements and control variables.

In the example, only a few variables remain common system wide, particularly the current reference $I_{ref}$, the period of sync pulses $T_{sync}$, and the frequency $f_θ$ the clock signal Clk θ used for counting in the various channel timers. While these parameters are global, meaning shared and common to the different operations, they are dynamic and can vary over time. As shown, $T_{sync}$ previously varies continuously during any variable frequency waveform synthesis and in some cases so does clock frequency $f_θ$.

All the other variables are defined specifically for each operation, namely the PWM brightness control duty factor D, the frequency $f_{synth}$ of the synthesized waveform, the phase delay Φ of each conducting channel during turn on, and the channel current $αI_{ref}$. The variables D and $f_{synth}$ are not actually control variables, per se, but the synthesized result of the combined control of $t_{on}$ for a specific channel or array of LEDs, along with the global variables $T_{sync}$, and possibly $f_θ$.

In the example of phototherapy waveform synthesis algorithm 330, operation 171a comprises generation of synthesized frequency $f_{syntha}$ for duration $Δt_a$ having PWM brightness $D_a$ conducting current $α_aI_{ref}$ in LEDs 120 having a wavelengths in the band $λ_2±Δλ_2$. Operation 171a is then immediately followed by operation 171b comprising synthesized frequency $f_{synthb}$ for duration $Δt_b$ having PWM brightness $D_b$ conducting current $α_bI_{ref}$ in LEDs 120 having the same band of wavelengths $λ_2±Δλ_2$. The waveform synthesized from operation 171b is blended for duration $Δt_g$ with LEDs 110 of wavelengths $λ_1±Δλ_1$ having a PWM brightness $D_g$ and biased at current $α_bI_{ref}$.

Thereafter operation 171c comprises generation of synthesized frequency $f_{synthc}$ for duration $Δt_c$ having PWM brightness $D_c$ conducting current $α_xI_{ref}$ in LEDs having wavelengths in the band $λ_3±Δλ_3$. Alternatively, in flow 173, operation 171c can be skipped altogether, or in flow 172 laser light 135 having a spectral band $λ_3±δλ_3$ is illuminated for a duration $Δt_f$ with PWM brightness $D_f$, phase delay $φ_f$ and biased at current $α_xI_{ref}$. Thereafter operation 171d comprises a delay $Δt_d$ where no LED or laser is illuminated followed by operation 171e, comprising generation of synthesized frequency $f_{synthe}$ for duration $Δt_e$ having PWM brightness $D_e$ conducting current $α_eI_{ref}$ in LEDs 110 having a wavelengths in the band $λ_1±Δλ_1$. Alternatively (not shown), a separate array of the same wavelength LEDs 110 can be "harmonized" with those in operation 171e being illuminated under the same driving conditions except having a synthesized frequency $f_{synthg}$ different than and preferably an even harmonic of synthesized frequency $f_{synthe}$. The entire process can then be repeated (flow 174) in totality or in part as desired.

Figure 23B:
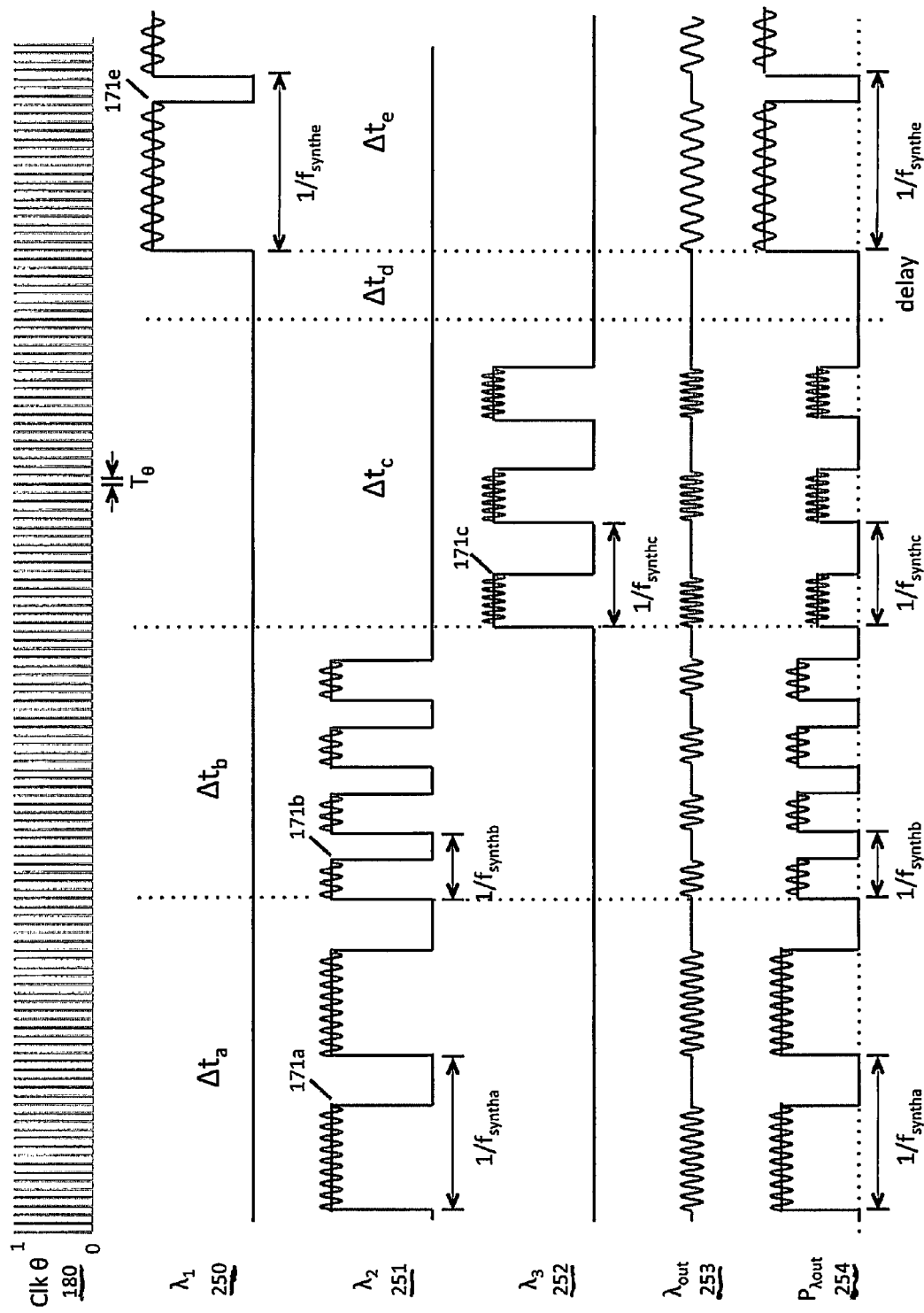
FIG. 23B is a timing diagram for synthesizing dynamically varying frequencies in multi-wavelength phototherapy system with dynamic brightness control.

The result of phototherapy waveform synthesis algorithm 330 is shown in the timing diagrams of FIG. 23B comprising the illumination of arrays of LEDs of wavelengths $λ_1$, $λ_2$, and $λ_3$ in diagrams 251, 252 and 253, of the combined output $λ_{out}$ mixing of varying wavelengths 253, and the total power output $P_{λout}$ of the varying LED wavelengths 254, all referenced to clock Clk θ 180 as a common time base. For simplicity, the LED outputs of only the main sequence in algorithm 330, comprising operations 171a, 171b, 171c, 171d, 171e, and 171g is shown.

During interval $Δt_a$ operation 171a results in a waveform having a repeated period $1/f_{syntha}$ and a PWM brightness approximately D=12/18=67%. While the interval shows only two cycles of the synthesized waveform, it should be understood that $Δt_a$ is minutes or tens of minutes in duration, while $f_{syntha}$ is milliseconds or tens of milliseconds in duration and cannot accurately be represented on the same time scale. Likewise it should be understood that duration $Δt_b$, $Δt_c$, $Δt_d$, and $Δt_e$ also comprise intervals of minutes to tens of minutes in duration and the synthesized waveforms have frequencies orders of magnitude faster.

Continuing with FIG. 23B, in interval $Δt_b$ operation 171b results in a waveform having a repeated period $1/f_{synthb}$ and a PWM brightness approximately D =4/7=57%. In Interval $Δt_c$ operation 171c results in a waveform having a repeated period $1/f_{synthc}$ and a PWM brightness approximately D=6/12=50%. In interval $Δt_e$ operation 171e results in a waveform having a repeated period $1/f_{synthe}$ and a PWM brightness approximately D=16/19=85%. If $f_θ$=935 Hz, then $T_θ$=1.07 ms and $f_{syntha}$=1/((1.07 ms)·18)=52 Hz. Similarly $f_{synthb}$=134 Hz, $f_{synthc}$=78 Hz, and $f_{synthe}$=49 Hz. Alternatively if a clock ten times faster is employed, i.e. where $f_θ$=9,356 Hz, then all the synthesized frequencies will likewise be ten times higher.

It should also be reiterated that the sine waves in FIG. 23B represent the optical output of the LEDs and are also not represented on the time scale, since the frequencies of infrared and visible light are many orders of magnitude higher than that of the synthesized frequencies.

Figure 24:
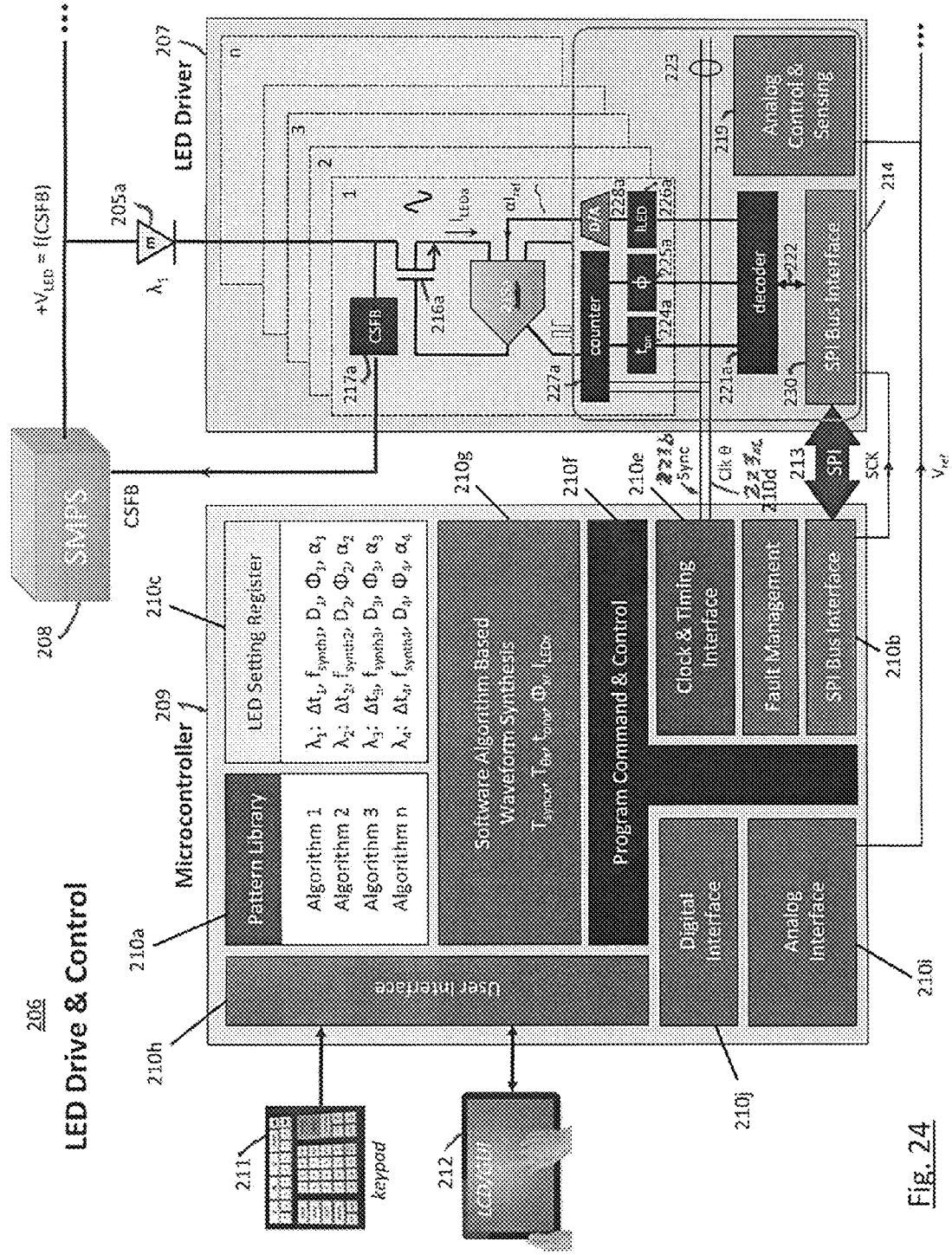
FIG. 24 is a block diagram representing the functions of the microcontroller in a phototherapy system according to the invention.

FIG. 24 illustrates a block diagram representation of microcontroller functions in phototherapy system and apparatus. As shown, LED drive and control 206 comprises microcontroller 209 with keypad 211 and touch screen 212, SMPS 208 and one or more LED driver ICs 207 driving various arrays of LEDs 205a comprising LEDs or laser diodes having any number of wavelengths λ.

Microcontroller 209 contains hardware, memory, firmware and software interface and control elements, including
    pattern library 210a comprising data and non-volatile memory containing any number of photoexcitation algorithms,
    SPI bus interface physical interface 210b with hardware and firmware based clocking and protocol management (including high speed physical bus and 10 MHz SPI-bus clock SCK used for clocking SPI data), LED setting register 210c comprising memory and data containing preset and reconfigurable LED bias and drive settings for each wavelength of LED (including sequence duration Δt, synthesized frequency $f_{synth}$, PWM brightness control by duty factor D, turn-on phase delay φ, and current multiplier $α_1$), fault management unit 210d comprising firmware and hardware including fault detection and recovery algorithms for a variety of fault conditions (such as shorted LED detect, open LED detect, and over-temperature detection).

clock and timing interface 210e comprising hardware, firmware and software for dynamically generating global system timing clocks (including Sync and Clk θ), program command and control unit 210f comprising internal data busses, data stacks, program counters, pointers, data accumulators, registers, firmware and software needed for instructing the arithmetic logic unit (ALU), counters, shift registers, and data storage in microcontroller 209 how to algorithmically synthesize waveforms, software algorithm based waveform synthesis 210g comprising program software and core ALU used to algorithmically synthesize waveforms and to generate control signals for LED driver ICs 207 (including dynamically varying sync pulse Sync having period $T_{syncx}$, dynamically varying counter Clk θ pulses having period $T_{θx}$, dynamically determining the LED on-time $t_{onx}$ for each and every channel of LEDs, dynamically determining the LED phase delay during turn-on $Φ_x$ for each and every channel of LEDs, and dynamically setting the digital register data $I_{LEDx}$ for each and every channel of LEDs), user interface 210h comprising a physical interface with firmware and software for decoding keypads, driving LCD displays, interpreting touch screen instructions, communicating user selections to program and control 210f (used to select algorithms and overwrite preset operating parameters), as well as to perform user identification and enforce login or used ID based security and privileges, analog interface 210i comprising hardware and firmware including data analog-to-digital (A/D) and digital-to-analog (D/A) converters for connecting to sensors and analog biofeedback information or for outputting analog control signals (such as Vref used by LED driver ICs 207), and digital interface 210j for connecting to digital inputs from sensors and other digital biofeedback information (including digital data handshaking with external devices and peripherals) and alternatively for interfacing to digital communication busses such as Ethernet, USB, IEEE1394, PC Express cards, and Thunderbolt, or to wireless data communication such as Bluetooth, WiFi, 3G, or 4G/LTE.

As shown, microcontroller 209 sends its instructions to LED driver ICs 207 through a high-speed digital bus, shown here as SPI bus 213 (with high-speed data handshaking managed by SPI serial clock SCK). Analog interface 210 also generates a precision voltage reference $V_{ref}$ used by analog control and sensing circuit 219 within each LED driver IC 207 to generate the precision reference current $I_{ref}$. Alternatively, $V_{ref}$ can be generated using discrete components. Clock lines 223a and 223b comprising counter clock Clk θ and Sync pulse signals are connected to counters 221a through 221n in LED driver IC 207.

Within LED driver IC 207 control and interface circuit 214 includes a single SPI bus interface 214, one per driver IC and an internal digital bus 222 communicating with decoders 227a through 227n (one decoder per channel). The decoded data is transferred to corresponding registers 224a through 224n, 225a through 225n, and 226a through 226n, respectively for $t_{on}$, Φ, and $I_{LED}$ data, respectively. Upon the next Sync pulse the $t_{on}$, and Φ data is loaded into counters 227a through 227n and $I_{LED}$ data is loaded into D/A converters 228a through 228n, controlling precision gate bias and control circuits 215a through 215n. As a result, the currents flowing through MOSFETs 216a through 216n and LED strings 205a through 205n are individually controlled by microcontroller 209.

Figure 25:
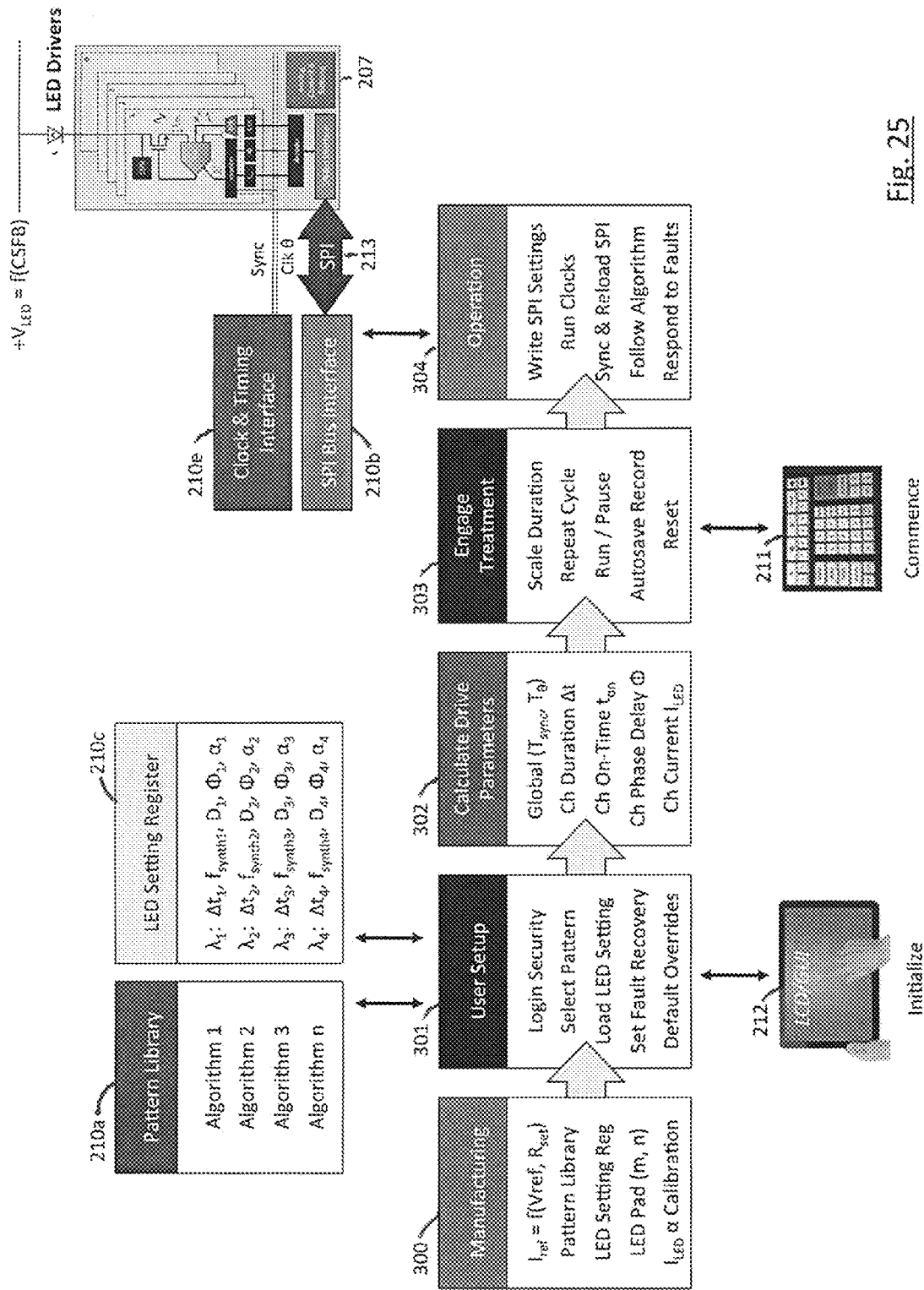
FIG. 25 is a flow chart of the set up and operation of the microcontroller in a phototherapy system of the invention.

FIG. 25 illustrates a flow chart of the microcontroller 209's setup and operation in the disclosed phototherapy apparatus, comprising steps 300 through 304. During manufacturing 300, the system is configured for the maximum possible LED current defined by $I_{ref}$ and set by trimming $V_{ref}$ to a precise value and selecting a value for $R_{set}$ corresponding to the maximum allowable current (i.e. where the $I_{LED}$ register is set to FF so that α=100%) for a particular model and geographic sales region or country. The nominal value operating current is then determined by scaling this maximum current to a lower number using the $I_{LED}$ data register and storing this value in a default register. Likewise, during initialization of a new unit, default algorithms are loaded into pattern library 210a, and default values for LED bias and operating conditions are loaded into LED setting register 210c for each type and wavelength of LED. During initialization, the corresponding LED pad configuration including the number of LED channels n and the number of LEDs in series m is also loaded into default registers. During final electrical test, the LED pad may optionally be set into calibration mode where all the LEDs of a given wavelength LED are operated at full brightness and the default values of $I_{LED}$ adjusted to achieve the best uniformity of brightness. This process is repeated and stored in a default register for $I_{LED}$. All default registers are stored in nonvolatile memory as described previously.

In an alternative embodiment of this invention, the apparatus is able to detect the attached LED pad and automatically configure the unit for the pad's particular configuration including its total number of LEDs, the number of channels, the number m of series-connected LEDs in an LED string, and the wavelengths of the LEDs used in each channel.

Before using the phototherapy apparatus, a physician or clinician first performs user setup 301 involving a login or security check to determine the user's privileges. Upon confirmation of the login ID and password, the apparatus loads programs and settings previously stored by the user into the menu selection. A successful login also enables privileges established by the device owner for that particular user. Such privileges may include the ability to change default settings, to create new recipes and algorithms, and for those with the appropriate credentials to operate the devices at a higher than normally allowed power level. For example, a physician may be authorized to drive LEDs at currents of 30 mA, while all other users are limited to current 20 mA and below. In the absence of a login, the unit can either be prevented from operation or allowed to operate in a restricted manner, e.g. limited to certain generic algorithms and LED settings.

To commence operation, the user first selects a pattern, i.e. a preprogrammed algorithm closest to the desired treatment.

The algorithms stored in pattern library 210a specify various sequences for driving LEDs, including the LED wavelengths λ and corresponding photoexcitation frequencies $f_{synth}$ for each step in the sequence. When selected from the pattern library, the algorithm is copied into volatile memory, specifically by reading the contents in the selected non-volatile memory and copying it into SRAM. The chosen algorithm automatically selects default conditions for driving each wavelength of LED for each step in the algorithm, including duration Δt, synthesized frequency $f_{synth}$, PWM brightness (set by duty factor D), turn-on phase delay Φ, and the LED current multiplier α (set by the $I_{LED}$ calibration curve). Once selected, these LED conditions stored in "LED setting register" 210c are copied into RAM from non-volatile memory.

Also during user setup 301, the default conditions for how the apparatus detects and deals with operating faults are copied from non-volatile "fault recovery" register into RAM. Operating faults include malfunctions in LED pads or cabling leading to the detection of "open" or "shorted" LEDs, or the detection of over-temperature conditions occurring in any LED pad or in any LED driver IC. Choices available when a fault condition occurs include shutting off the entire system immediately, disabling the malfunctioning channel, adjusting the bias conditions and confirming if the fault disappears, operating the unit with the fault by backing off on the drive currents, or ignoring the fault until a subsequent fault is detected.

In the case of over-temperature detection, a warning sent from an LED driver IC informs the microcontroller that the IC is overheating. In one embodiment, the microcontroller then identifies any channel with a shorted LED and either shuts it off or reduces the current in that channel, checking again to confirm that the fault has been cured or shutting it down. A secondary thermal protection circuit insures the device is shut off before a dangerous temperature occurs, independent of microcontroller instructions.

User setup 301 facilitates control of the phototherapy apparatus in accordance with a user's privileges. By copying the selected program algorithm, LED settings, and fault recovery settings into RAM, an authorized user can change recipes and LED settings via keypad 212 or touchscreen 211 without the risk of accidentally modifying the unit's default settings stored in non-volatile memory.

While the disclosed invention synthesizes photoexcitation frequencies $f_{synth}$ using square wave pulses, other waveforms such as sawtooth, triangular, and sine wave synthesis are also possible.

After the conditions are chosen, the operation 302 in FIG. 25 illustrates that a number of variables must then be calculated before operation commences. Calculated variables most importantly include the period $T_{sync}$ of the Sync pulse and the on time $t_{on}$ for every channel, variables shown to change with virtually every step in waveform synthesis. These calculations depend on the frequency of Clk θ since this clock represents the time basis for the counters used in frequency synthesis, brightness control and phase delay.

In one case, the selection of the clock period $T_θ$ of Clk θ is set as fixed multiple of $T_{sync}$ either equal to the maximum count of the counter or alternatively to some lesser ratio. For example if a 12-bit counter is employed, Clk θ may operate at a frequency 4096 times faster than the Sync pulse, or if higher speed is preferred over precision, then Clk θ may operate at a frequency 1024 times higher than the Sync pulse. In an alternative embodiment, Clk θ is free-running and the Sync pulse occurring whenever it is required to update data without influencing Clk θ. For the sake of discussion, we assume a fixed $T_θ$ and a dynamically varying period for $T_{sync}$.

Once the frequency $f_{synth}$ is selected for a particular LED wavelength and a given step in the sequence, the microcontroller calculates the appropriate period $T_{synth}$ corresponding to the selected frequency where $T_{synth}=1/f_{synth}=n_{synth}T_θ$. The Sync pulse is then generated at the period of the synthesized waveform, i.e. $T_{sync} \equiv T_{synth}$. If, however, more than one frequency is being synthesized simultaneously the highest frequency, i.e. the shortest value of $T_{synth}$ should be used to determine the Sync pulse.

Each conducting channel must repeat its cyclic count corresponding its synthesized frequency. Rearranging the relation in terms of the number of Clk θ clock pulses $n_{synth}$ results in $$n_{synth}=T_{synth}/T_θ=1/(T_θ \cdot f_{synth})$$

This means that a specific channel must restart its sequence very $n_{synth}$ pulses. If only frequency is being synthesized, this restart occurs once for every Sync pulse. If the fastest frequency is being synthesized on a given channel, then for that channel the restart also occurs once for every Sync pulse. If however, a frequency is being synthesized in a phototherapy system generating multiple frequencies, then multiple Sync pulses may occur before the specific channel repeats its cycle. In such cases the microcontroller must calculate the pulses remaining and exhaust that count before restarting the cycle and again turning on the channel, i.e. setting $t_{on}>0$.

The desired brightness (specified by the algorithm as duty factor D) is used to calculate the on-time $t_{on}$ for each channel also represented by the number of pulses, where by $$t_{on}=D \cdot n_{synth}$$

This calculation is performed for every channel. So for each channel, the microcontroller calculates an on time described by the number of clock pulses $t_{on}$ and a period $T_{synth}$ specified by a number of clock pulses $n_{synth}$. For each Clk θ pulse the value of $n_{synth}$ and $t_{on}$ within the microcontroller waveform synthesis calculation are decremented by one pulse, having a current value represented by the variables $n'_{synth}$ and $t'_{on}$.

Provided that a Sync pulse does not occur first, when the $t_{on}$ count reaches zero, the counter in the channel driver will shut off that channel's LED string. Meanwhile the microcontroller will continue to count down the balance of pulses remaining in the $n_{synth}$ register and otherwise take no action to update the registers in the LED driver ICs. Also, provided that during this interval a Sync pulse does not occur first, when the $n_{synth}$ count for the channel finally reaches zero, the microcontroller generates a Sync pulse, and the channel is reloaded with the original value for $t_{on}$ turning the off LEDs in the channel back on and restarting the counter. Concurrently within the microcontroller program the full value for $n_{synth}$ is reloaded and the count down starts anew.

If a Sync pulse, however, occurs before either the $t_{on}$ counter or the $n_{synth}$ counter reach zero, then the current balance of $t'_{on}$ is rewritten to the counter in the channel driver, thereby keeping the LED channel on and restarting the counter with the new (smaller) value of remaining on time, while the microcontroller continues to decrement the $n'_{synth}$ counter unabated until it reaches zero.

Alternatively, should a Sync pulse occur after a channel has turned off (i.e. after the $t_{on}$ counter has counted down to zero), but before the synthesized period has been completed where the $n_{synth}$ counter has not yet reached zero, then when the Sync pulse occurs the channel on-time must be rewritten to the registers in the channel driver with the value $t_{on}=0$ to maintain the channel in its off state while the microcontroller continues to decrement the $n'_{synth}$ counter unabated until it reaches zero.

In summary, the number of clock pulses $n_{synth}$ represents the count needed to synthesize a desired frequency as specified by a given algorithm and LED settings selected from pattern library 210a and LED setting register 210c whether modified or unaltered by a user. Whenever the present value of $n'_{synth}$ counts down to zero on any channel in the system, the microcontroller automatically sends a Sync pulse. In response to the Sync pulse, the channel that caused the Sync pulse reloads its $t_{on}$ register, turns on its LED string anew, and starts counting it's $n_{synth}$ count all over again. In response to the Sync pulse, any channel that is still on must reload its present remaining $t'_{on}$ balance into the $t_{on}$ register of the channel driver (keeping the LED string on) and restarting the count down, while continuing to decrement it's $n'_{synth}$ count without any changes. Alternatively in response to the Sync pulse, any channel that already off must reload its $t_{on}$ register with zero (thereby keeping the LED off), while continuing to decrement it's $n'_{synth}$ count without any changes.

While the algorithm is described above using counters, since the times and clock rates are specified a priori, the actual clock pulse when the Sync pulse is to be generated can be calculated in advance, stored in a register and compared to the value in the counter generating the $T_{sync}$ pulse from the Clk θ clock. When the defined conditions occur, the Sync pulse is generated and the appropriate data is loaded into the LED driver IC's data registers.

Referring again to operation 302 "calculate drive parameters", the value of the total duration Δt specified in clock pulses is simply the real time duration (in minutes) divided by the clock period $T_θ$. The value of current $I_{LED}$ is directly copied from the calibration table. If a different value is desired, the correction for the calibration should be added or subtracted linearly to the desired number to maintain an accurate brightness.

For phase delay, unless manually overwritten the clock delay Φ=z specified is added incrementally to each channel so that the delay linearly propagates (as shown in FIG. 22) whereby for each channel $Φ_1=0$
$Φ_2=z$
$Φ_3=2z$
$Φ_4=3z$
$Φ_n=(n-1)z$ To engage treatment 303, the user has an option to scale the treatment duration or alternatively to repeat the cycle. In the scale duration option, the entire cycle is divided down in proportion to fit into an allotted time. Repeat cycle repeats the entire sequence by a fixed number of cycles and reports the time required. Run/pause starts or hold the procedure while Reset starts set up 301 over from scratch. Autosave record keeps a digital record of what procedures were performed, when they were performed and the new settings resulting from manual overrides.

Once the program commences operation 304, the SPI bus writes the values of $t_{on}$, φ and $I_{LED}$ to the data registers within LED driver IC 207 through SPI bus interface 210b and SPI bus 213, docking of Clk θ and Sync commence as generated from clock and timing circuit 210e and LED operation implementing phototherapy waveform synthesis algorithms 330 begins. As described previously, with each Sync pulse, updated values of register data are rewritten to the LED driver ICs according to the specified algorithms, and any fault conditions are reported to the system and ultimately to the user.

LED Pad Design

Figure 26:
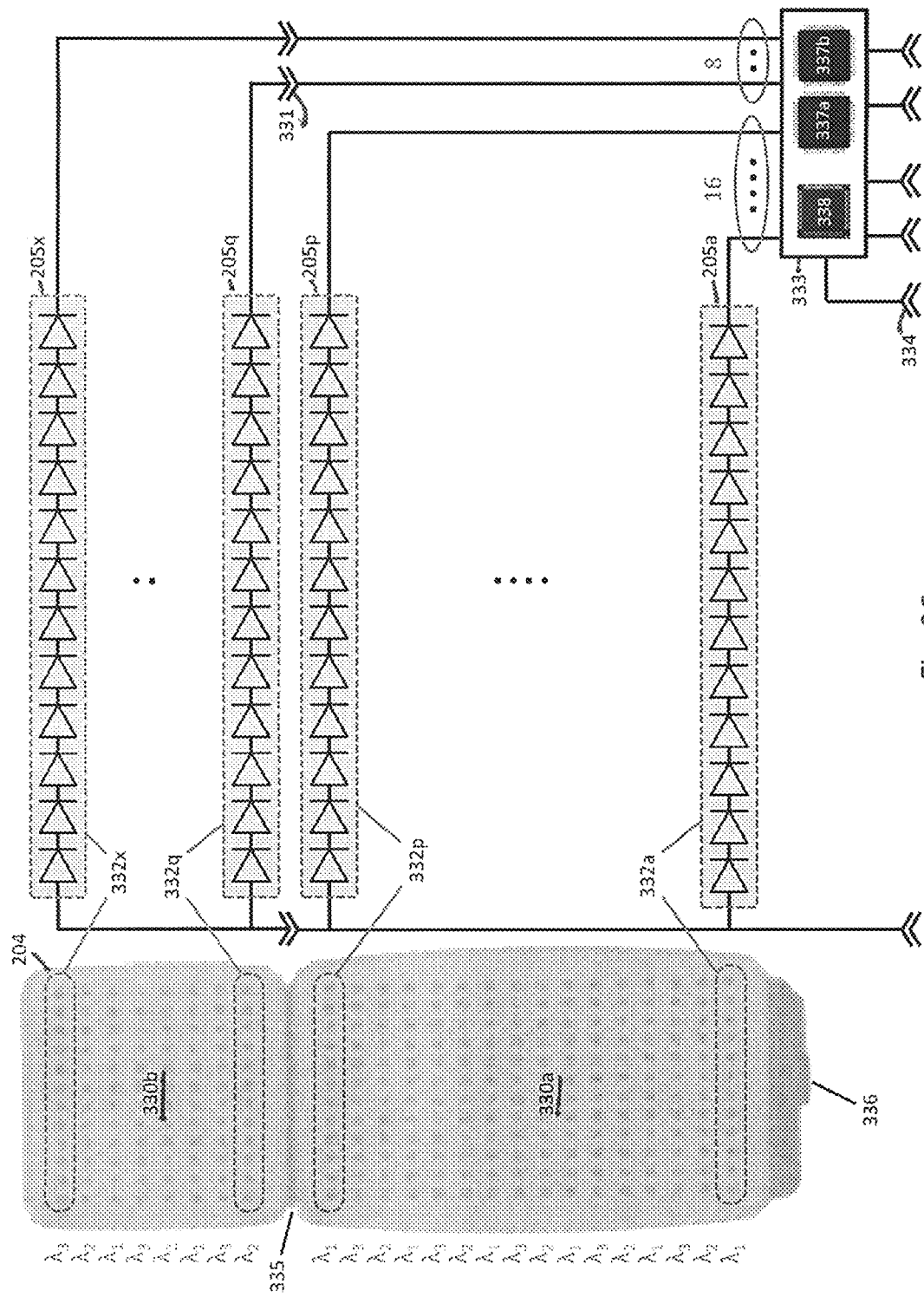
FIG. 26 is a plan view and equivalent circuit of the LED pad.

Aside from its electronic control, the disclosed phototherapy apparatus includes an aseptic flexible pad containing an array of LEDs illustrated in plan view in FIG. 26 and having an associated equivalent circuit schematic as shown. Pad 204 is formed using a material biochemically inert material such as Teflon or other non-porous non-reactive materials, and containing embedded electronic components including connectors, wires or conductive interconnects, flexible and semi-flexible PCBs (printed circuit boards), transistors, ICs, passive components (such as resistors and capacitors), and LEDs.

The pad material may be homogeneous or comprise a softer interior material with an impervious aseptic coating. To prevent biological cross contamination among patients, the exterior of the pad should be relatively non-porous to avoid trapping bacteria, viral and microbial contaminants, and should not be damaged by soap and water, phosphates, alcohol, low concentration acetic acid, commercial disinfectants, and other anti-bacterial agents. Without substantially diminishing its light output, the pad should ideally completely enclose and contain its LEDs within this bacterial barrier or coating material or otherwise form a hermetic seal with the LEDs protruding through the pad material. The pad should also preferably form a hermetic seal, bacterial and moisture barrier with any connectors or wires protruding from the pad. If absolute hermeticity is not possible, steps should be taken in manufacturing to insure the best seal possible, especially to insure delamination between the pad material and the extruding wires and components is minimized by conditions used in molding or forming the pad itself.

In one embodiment, pad 204 is divided into two pad portions, a larger pad portion 330a comprising 16 rectilinearly arranged strings of LEDs 332a through 332p and a smaller pad portion 330b comprising rectilinearly arranged 8 strings of LEDs 332q through 332x. Larger and smaller pad portions 330a and 330b are fastened together mechanically at bendable seam 335 containing an electrical connection represented by connector 331, The pad is designed to, when needed, wrap around a patient's appendage and optionally to secure the top of pad 330b to the bottom of pad 330a with mechanical fastener 336.

Mounted on a flexible or semi-flexible PCB. LED driver PCB 333 includes both passive and semiconductor components including LED driver ICs 337a and 337b, and optionally microcontroller 338. In one embodiment, PCB 333 is located within the end portion of larger pad portion 330a near fastener 336. Connector 334 electrically connects pad 204 to power and alternatively to LED driver circuitry not contained within LED driver PCB 333. Given that LED driver IC 333 is contained within larger LED pad 320a and LED strings 332q through 332x are contained within smaller pad portion 330b, the cathodes of series-connected LED strings 205q through 205x are connected to LED driver PCB 333 through electrical connector 331 while cathodes from LED strings 205a through 205p can be connected without an intervening connector.

Electrically, each string as shown contains 12 series-connected LEDs sharing a common anode and with cathodes separately connected to LED driver PCB 333. For example, LED string 332a comprises the bottommost LED string on larger pad portion 330a and has an equivalent circuit represented by 12 series-connected LEDs 205a driven by a single channel on LED driver IC 337*a* contained within LED driver PCB 333. Similarly, LED string 332*p* comprises the topmost LED string on larger pad portion 330*a* and has an equivalent circuit represented by 12 series-connected LEDs 205*p* separately driven by a different channel on LED driver IC 337*a*. On smaller pad portion 330*b* LED string 332*q* has an equivalent circuit represented by 12 series-connected LEDs 205*q* driven by a single channel on an LED driver IC 337*b* also contained within LED driver PCB 333 and connected through electrical connector 331. Similarly, LED driver IC 337*b* drives LED string 332*x* with an equivalent circuit represented by 12 series-connected LEDs 205*x*. Alternatively LED driver PCB 333 may be eliminated completely and the cathodes of all the LED strings connected directly to connector 334.

As shown in the embodiment of FIG. 26, each rectilinearly positioned LED string in the array comprises LEDs of substantially the same wavelength $\lambda$, Ideally of similar brightness, where the wavelength of the LEDs various across the pad in some regular and periodic fashion. For example, LED strings 332*a*, 332*d*, 332*g*, 332*j*, 332*m*, 332*p*, 332*s*, and 332*v* comprise LEDs of wavelength $\lambda_1$, LED strings 332*b*, 332*e*, 332*h*, 332*k*, 332*n*, 332*q*, 332*t*, and 332*w* comprise LEDs of wavelength $\lambda_2$, and LED strings 332*c*, 332*f*, 332*i*, 332*l*, 332*o*, 332*r*, 332*u*, and 332*x* comprise LEDs of wavelength $\lambda_3$.

While the LEDs of the same wavelength are shown positioned in straight lines and arranged as rows, the LEDs may be distributed in other patterns, e.g. alternating the LED wavelengths along both row and columns in more complex patterns, where the layout of any given string 332 cannot be represented as a straight line, but where the circuit connection 205 still remains a simple series connection of 12 LEDs. To facilitate a more uniform distribution of the various wavelength LEDs, a two layer flexible PCB or the use of conductive jumper may be required to electrically maintain a series connection of the same wavelength LEDs. It is important LEDs of dissimilar wavelength should not be mixed into the same series electrical connection or the ability to sequence or blend the brightness of dissimilar wavelengths of light will be lost.

To maintain flexible adjustment of the size of LED pad 204, small pad portion 330*b* can be removed from large pad portion 330*a* and electrically disconnected using connector 331 without disturbing operation of the arrays of LEDs in large pad portion 330*a*. Alternatively the pad may be designed to support a second small pad portion (not shown) electrically connected to LED driver board 333 through a second connector (not shown). In one embodiment, the second small pad portion is physically attached to the large pad portion 330*a* by a fastener at the bottom of large pad portion 330*a* or by adapting faster 336 to support both configurations. In such instances the electrical connector between the large pad portion 330*a* and the optional small pad portion containing the common anode connection and the separate cathode connections driving the additional LED strings should not interfere with the function of electrical connector 334 used to connect to power or drive electronics to pad 204.

In a second embodiment, the second small pad portion is physically attached to the large pad portion 330*a* by a fastener located at the top of large pad portion 330*a*. In such instance the common anode connection and the separate cathode connections driving the additional LED strings must be routed to LED driver PCB 333 through smaller pad portion 330*b* requiring a second electrical connector located at the top of smaller pad portion 330*b* to connect to optional small portion pad 330*c*, and requiring double the pins on connector 331 to accommodate the additional LED driver lines. For example without the ability to add optional small pad portion 330*c*, electrical connector 331 requires a minimum of 10 pins-8 connector pins for LED cathode lines 205*q* through 205*x* and another two for the common anode line and ground.

In the alternative embodiment with the expansion feature, the connections need to drive the optional second small portion pad requires 8 additional lines and to share the common anode and ground lines, increasing the number of pins needed in connector 331 by 9, i.e. from 10 connector pins to 18 connector pins. As shown, LED driver IC drives 16 LED strings from a single device. LED driver IC also includes separate outputs, the addition of the second small pad portion as an extension to LED pad 204 requires no change in the electrical design or operation of the pad, except that the open LED connections should not trigger an open LED fault in LED driver IC 337*b*. The fault setting register to avoid false open LED detect faults is user programmable in most LED driver ICs and can be controlled via microcontroller 209.

Although ground has no function in small pad portion 330*b* and the second optional small pad portion, in an alternative embodiment, the ground potential is used to bias an electrical shield throughout pad 204 to comply with industry EMC (electromagnetic compatibility) specifications for controlling unwanted electromagnetic interference (EMI) during operation, especially when high-speed clocks are employed for high bandwidth waveform synthesis. In single layer PCBs, the ground layer can be used to bias conductors in all the PCB area not used by carrying LED currents; in dual layer PCBs the second layer can be used as a ground plane, greatly diminishing the radiated noise and providing EMI shielding, or in a 3-layer PCB, the front and backside layers both be grounded acting as a Faraday cage surrounding and encasing the conductors carrying LED currents, with the only openings in the front side conductors open to accommodate mounting the LEDs. In another embodiment, a wire mesh comprising insulated wire is placed around a single layer PCB with only the LEDs protruding beyond the mesh, whereby the wire mesh is biased to ground to form a Faraday cage. The entire unit, including the PCB and wire mesh, is then molded with Teflon, whereby only LEDs protrude from pad 204.

Figure 1:
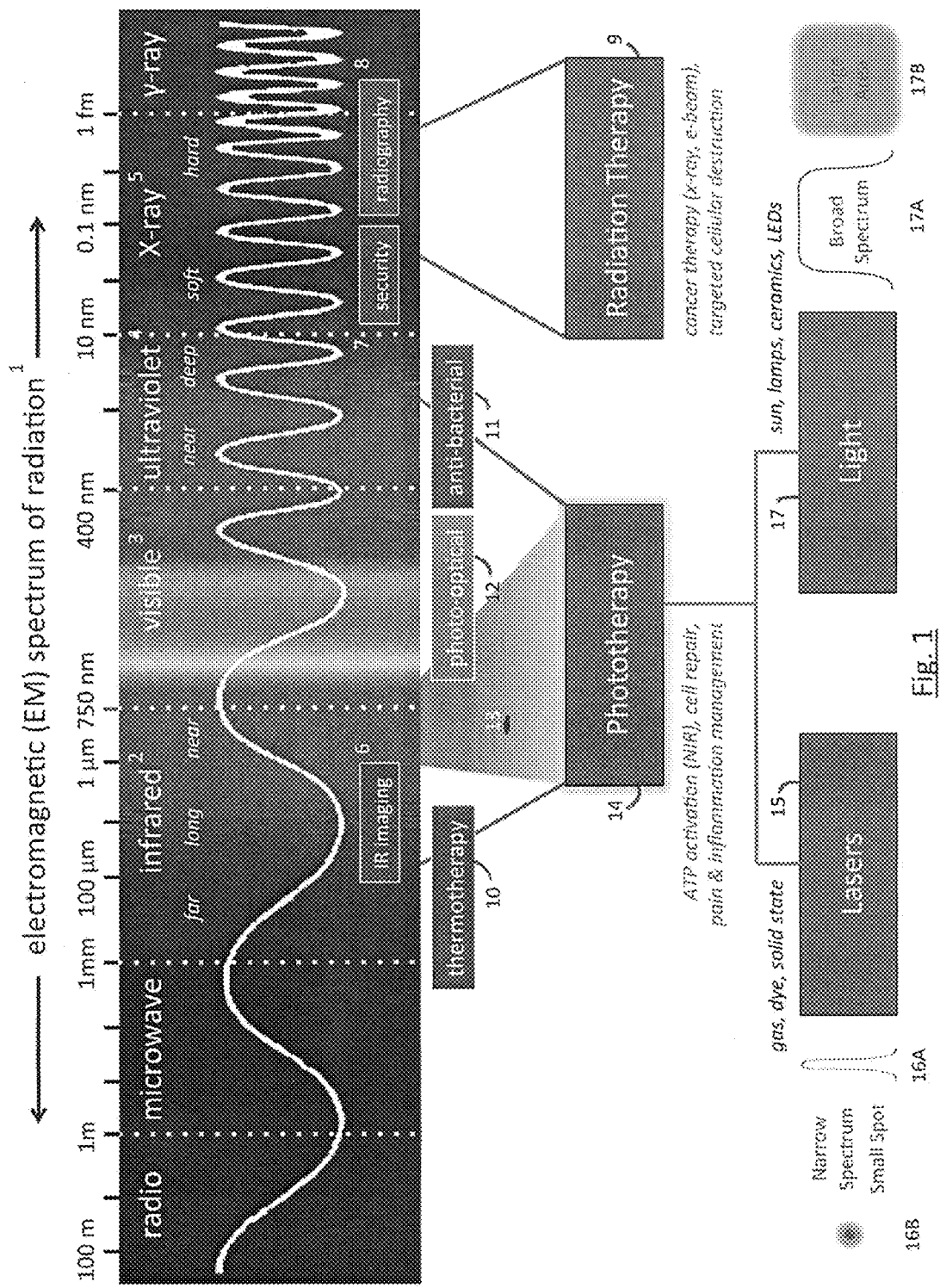
FIG. 1 is a graphical illustration of the electromagnetic spectrum of radiation, contrasting phototherapy to radiation therapy.
Figure 2:
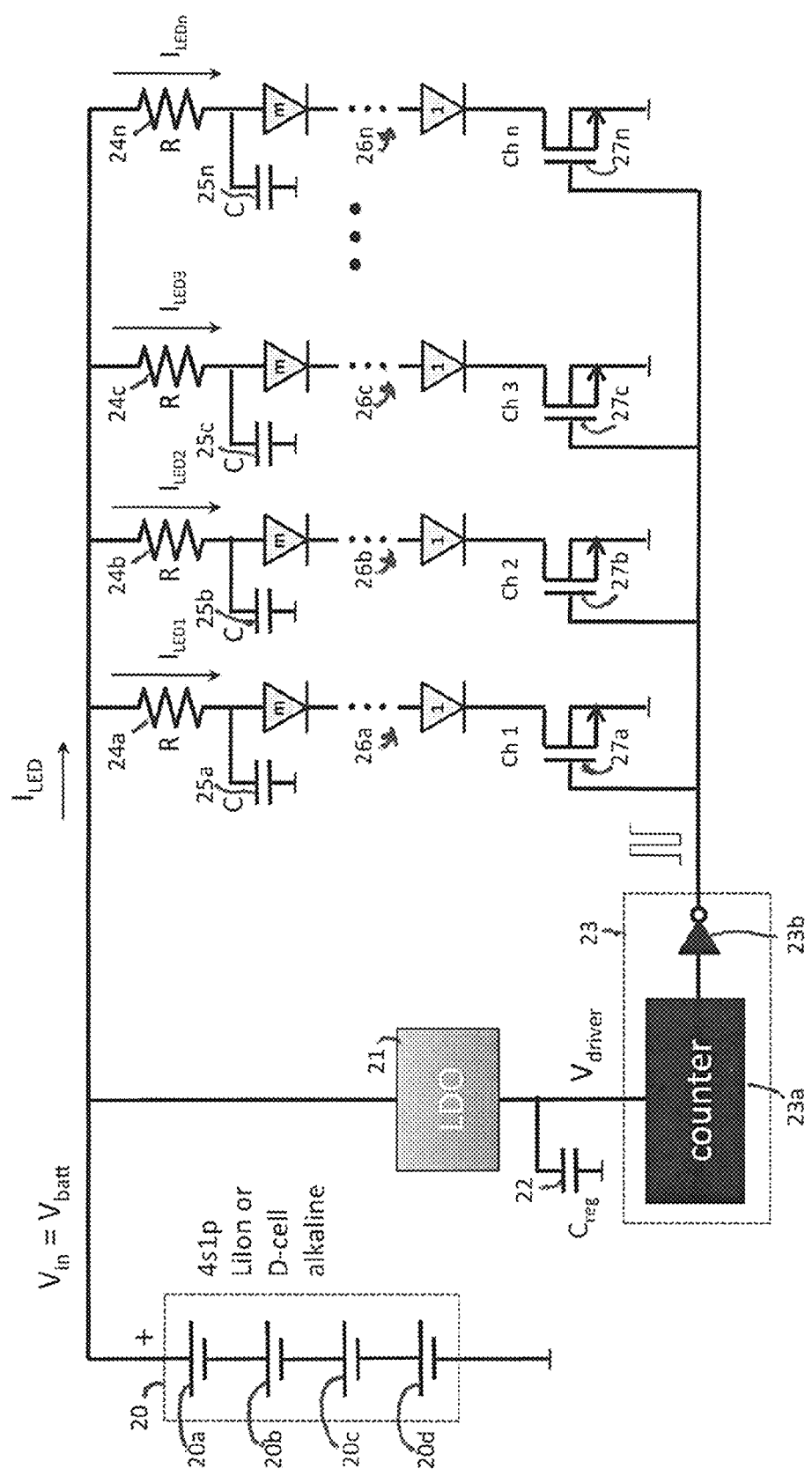
FIG. 2 is a schematic circuit diagram of a voltage-based LED driver and dimmer circuit.
Figure 3:
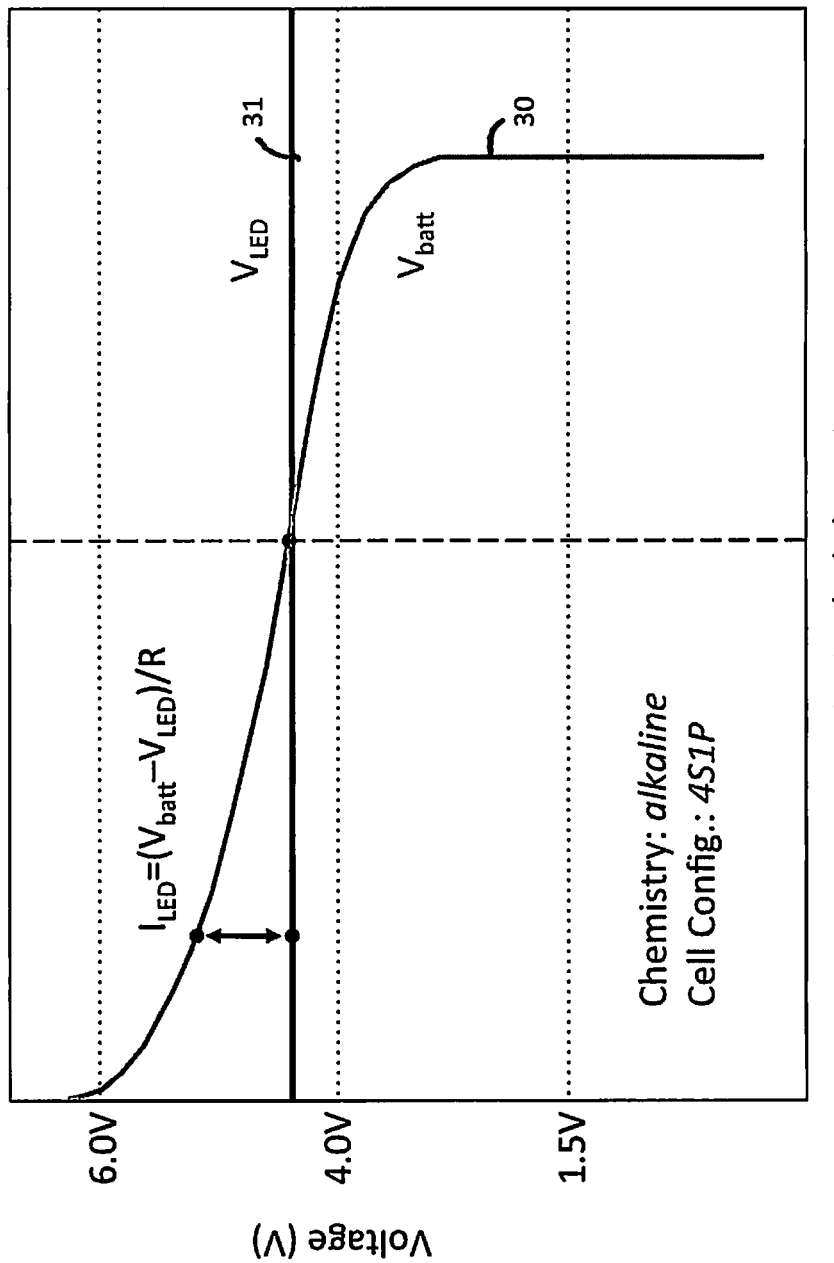
FIG. 3 is a graph illustrating the impact of battery discharge on LED current in voltage based LED drivers.
Figure 4A:
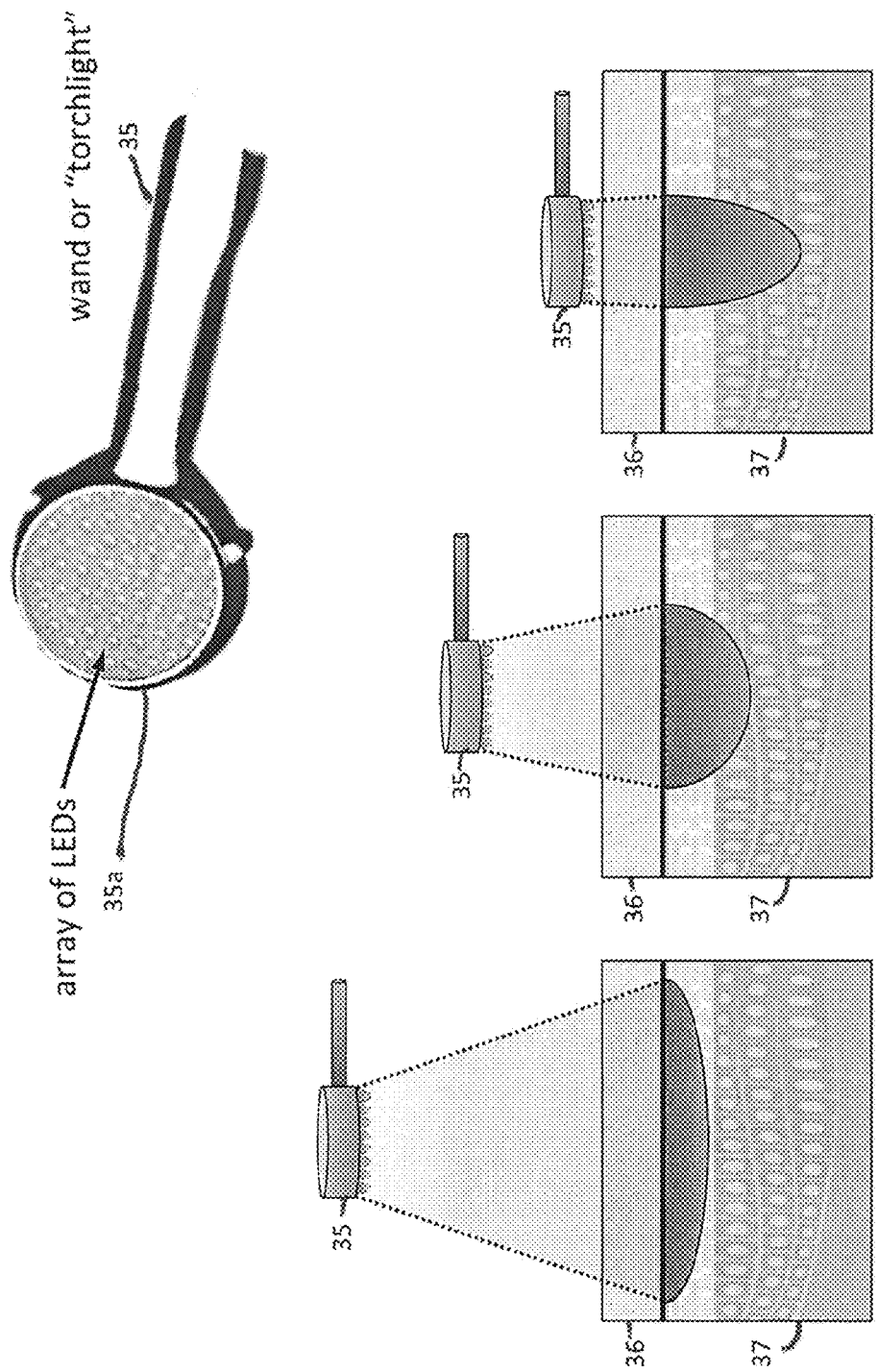
FIG. 4A is a view illustrating the problem of maintaining a consistent position and phototherapy depth with a handheld LED wand or torchlight.
Figure 4B:
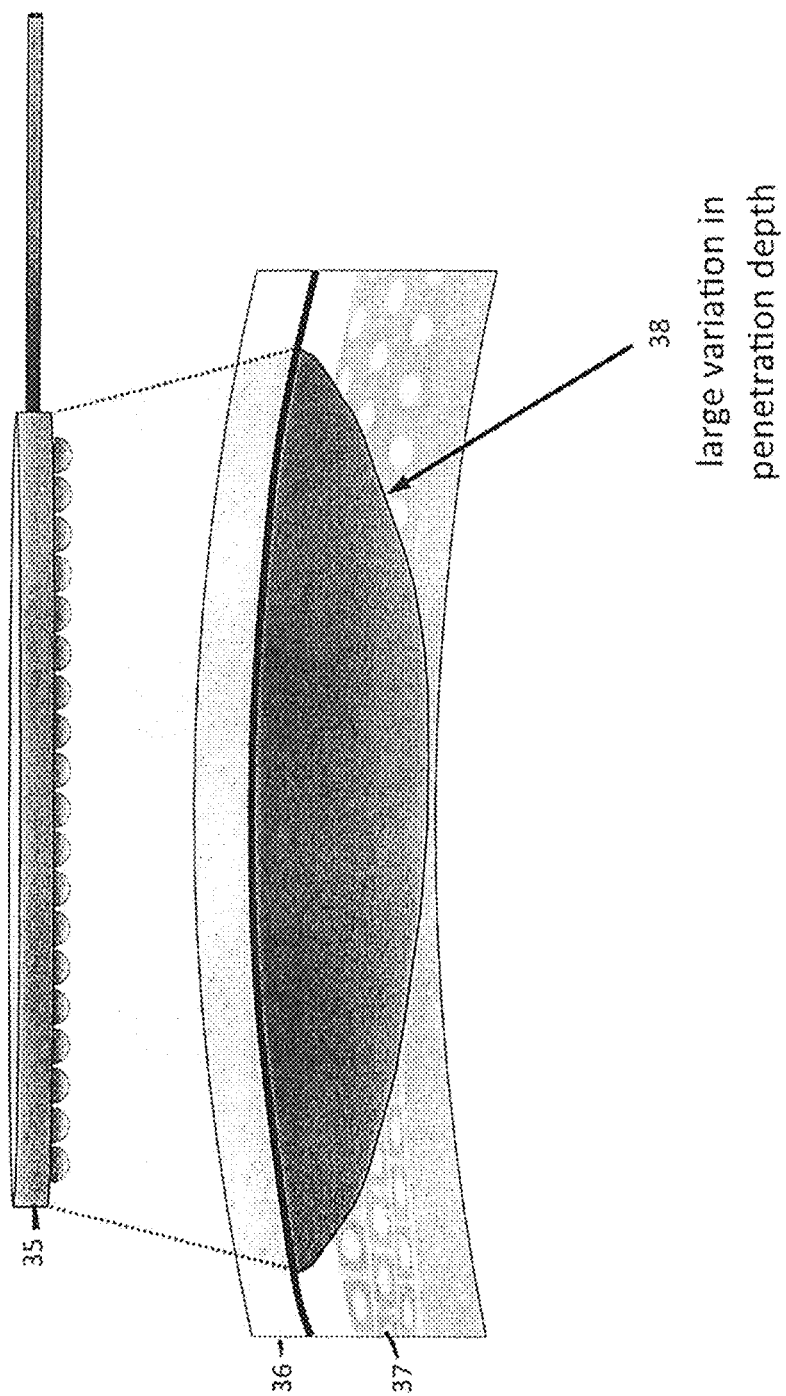
FIG. 4B is a detailed view illustrating the problem of maintaining a consistent phototherapy depth over large area with a mechanically inflexible LED array.
Figure 5B:
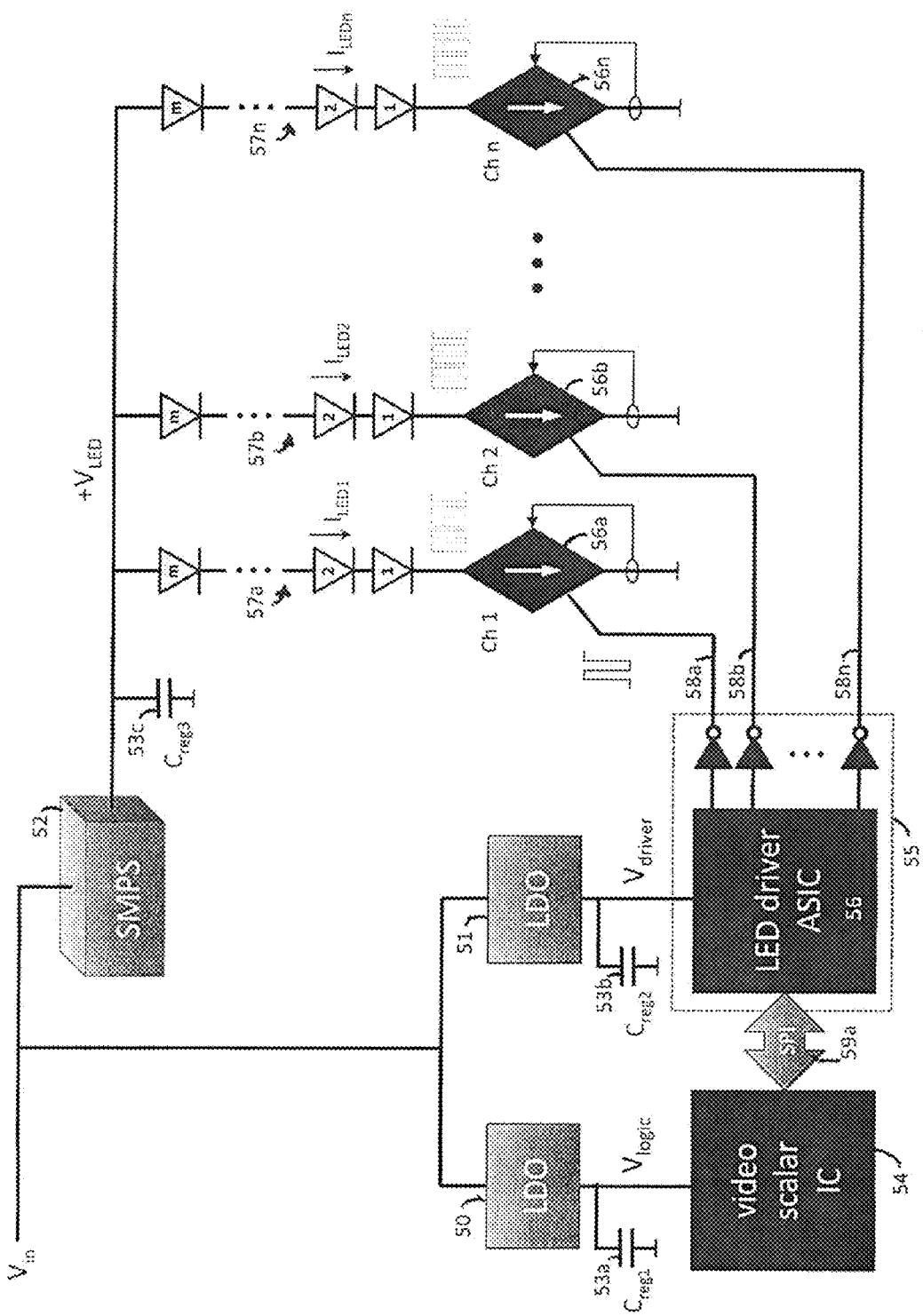
FIG. 5B is a schematic circuit diagram of constant-current LED driver of the type used as a HDTV backlight.
Figure 6A:
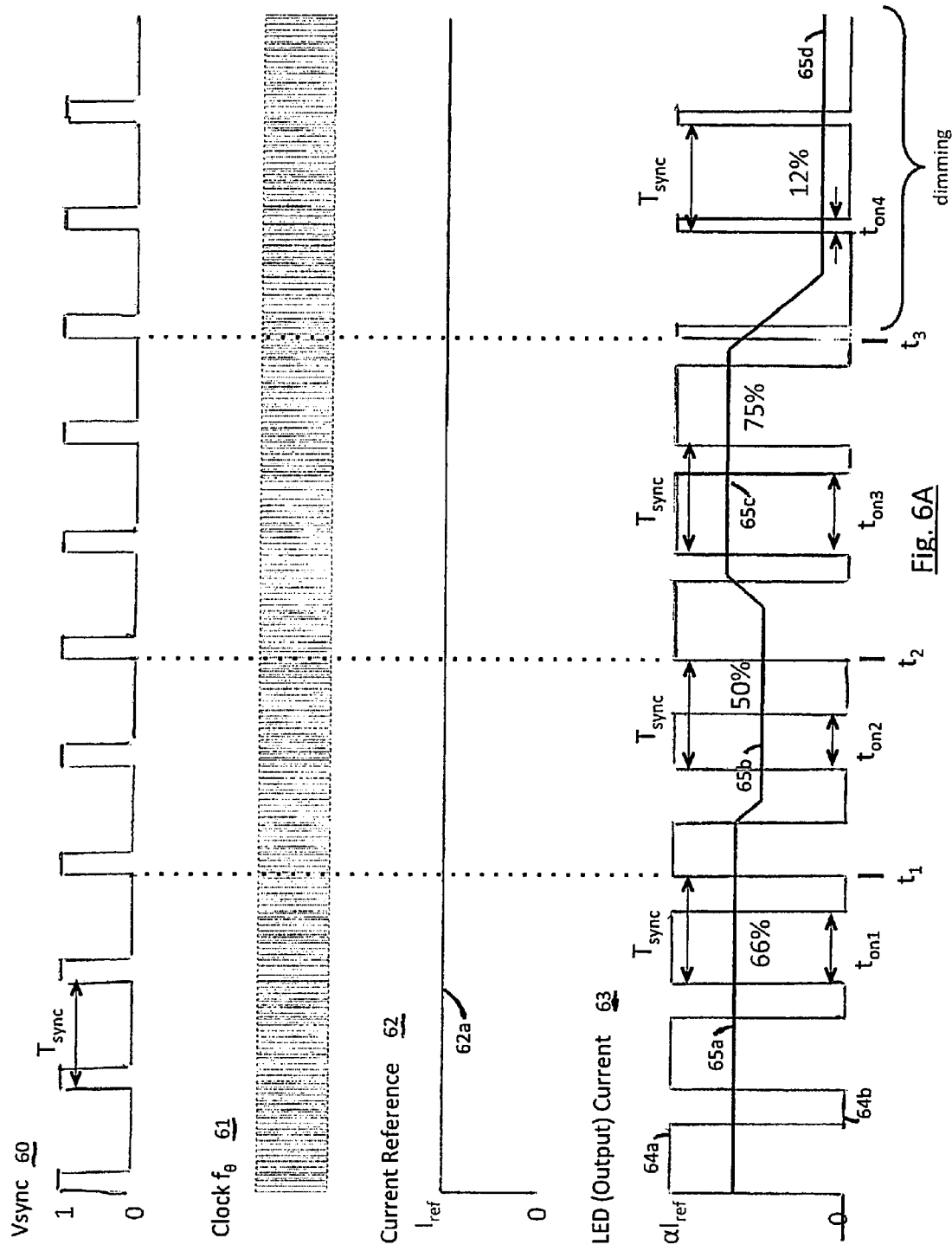
FIG. 6A is a series of graphs illustrating fixed frequency PWM backlight brightness control in a 2D-mode LED backlit HDTV.
Figure 6B:
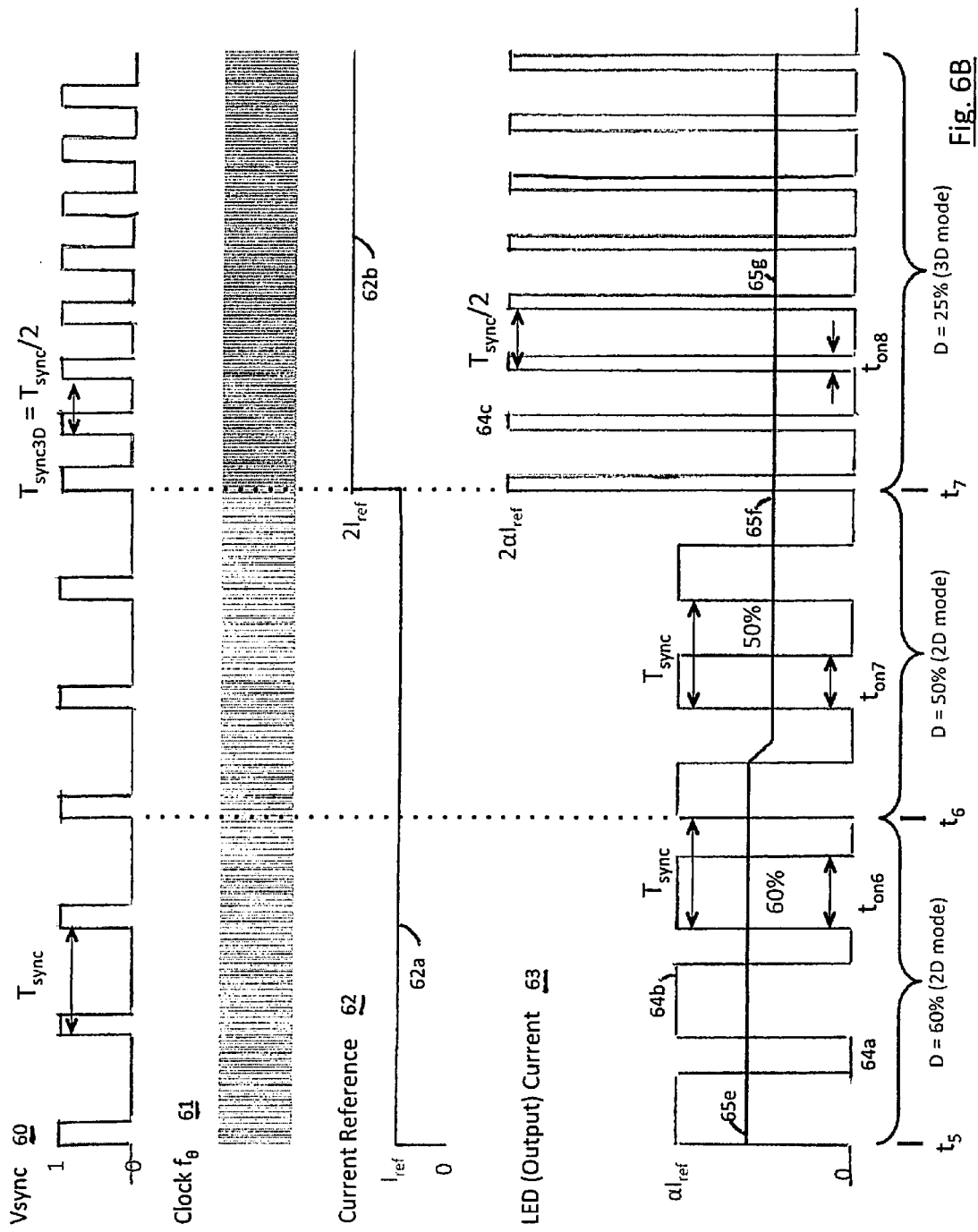
FIG. 6B is a series of graphs illustrating fixed frequency PWM backlight brightness control in a 3D-mode LED backlit HDTV.
Figure 7:
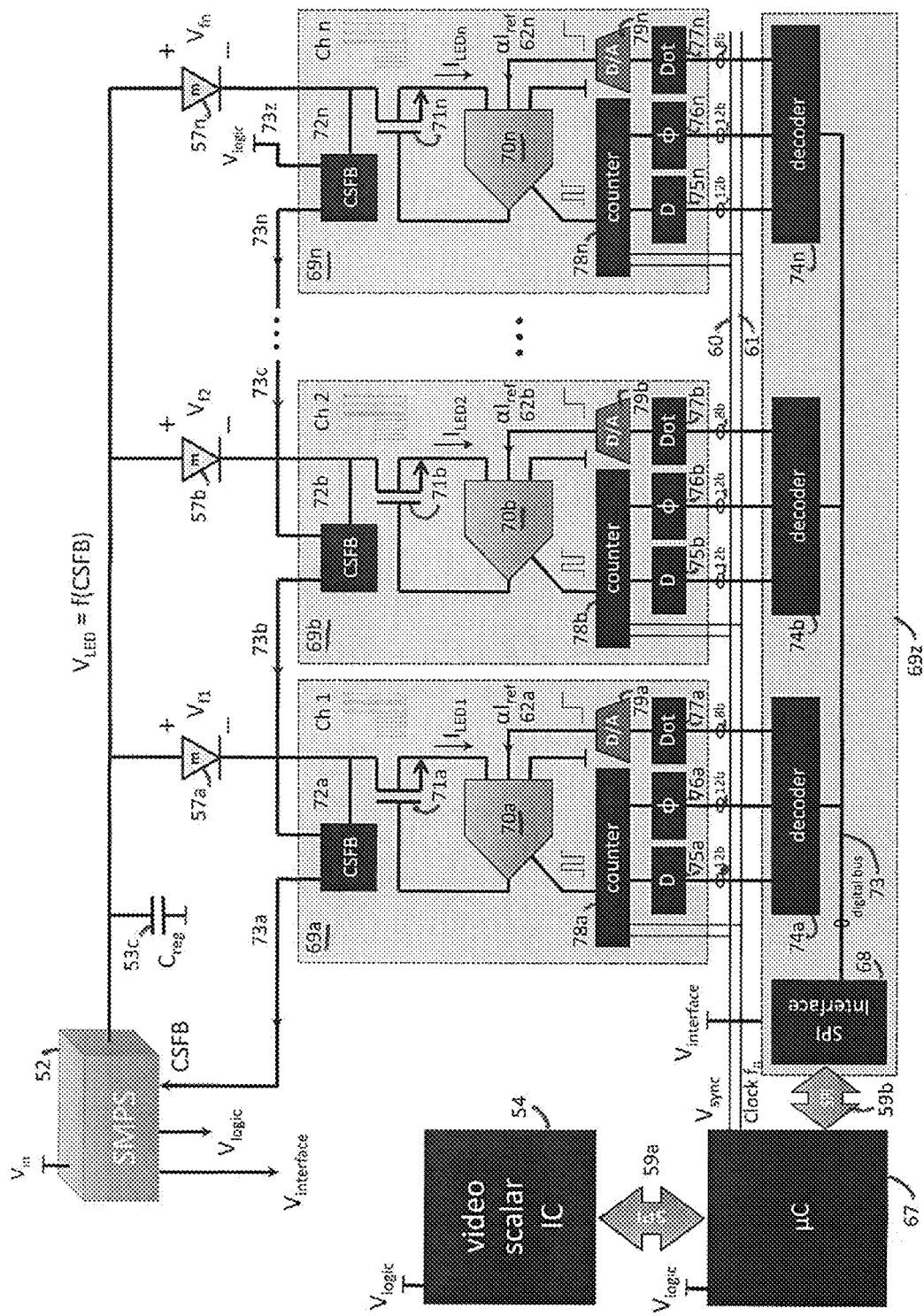
FIG. 7 is a schematic circuit diagram of an architecture for a LED backlit HDTV.
Figure 27:
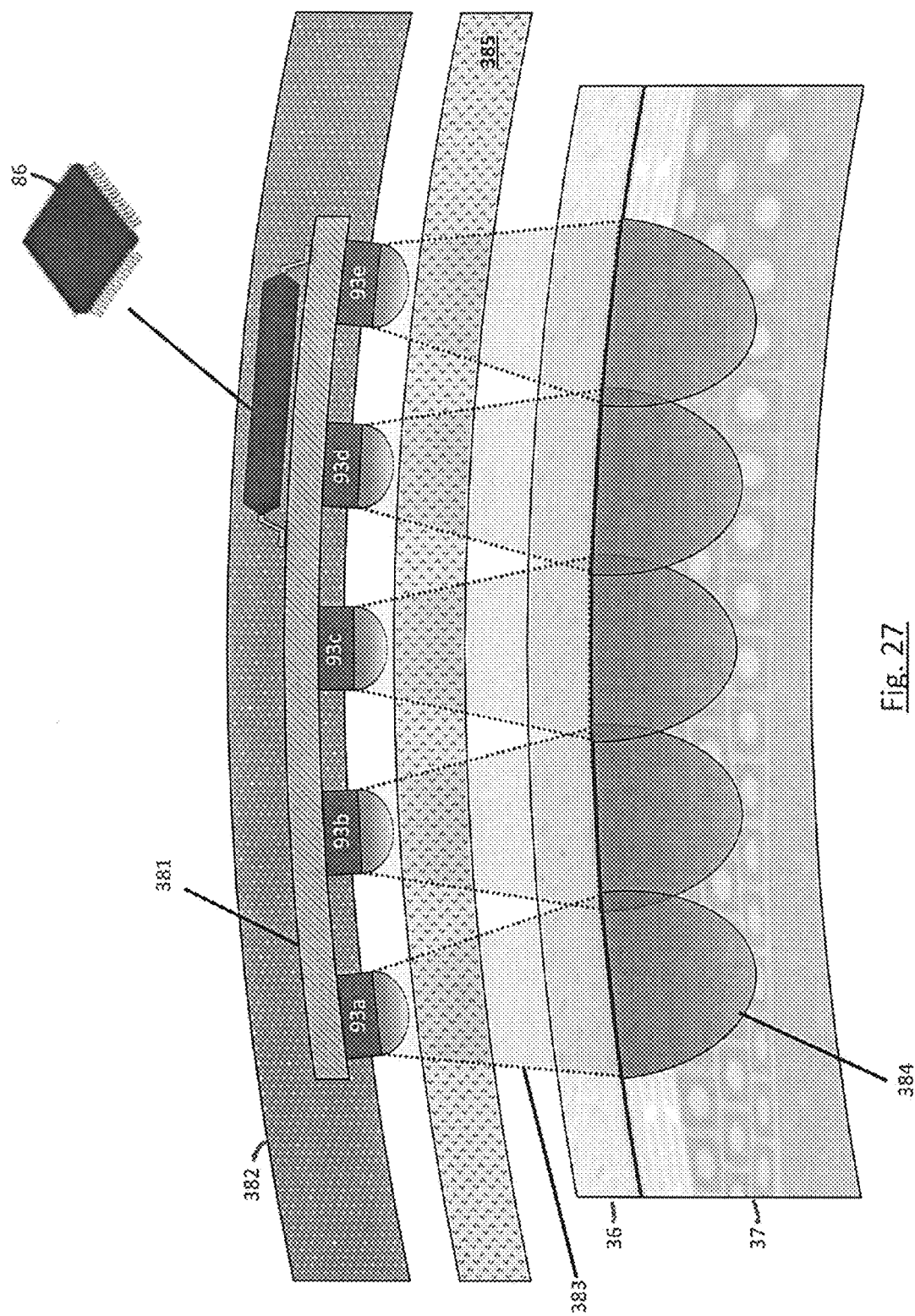
FIG. 27 is a cross-sectional view of a flexible LED pad conforming to a curved surface.

The flexibility of LED pad 204 to conform to the topographic curvature of the area receiving photoexcitation is important to avoid issues concerning poor light uniformity and varying penetration depths problematic with wands, torchlights, and stiff pads such as those illustrated in FIG. 4A and FIG. 4B. The benefit of the flexible and semi-flexible pad is shown in FIG. 27, including flexible molding 382, e.g. comprising Teflon, flexible PCB 381, and flexible aseptic barrier 385. Subdermal and epithelial tissue 37 and 36 naturally conform to the body part requiring phototherapy, especially important for the uniformly illuminating tissue on the arms, legs, or neck. By bending to conform to the curvature of the treated area, LEDs 93*a* through 93*e* are able to adjust their radiated light pattern to be nearly perpendicular to the curved surface of epithelial layer 36, resulting in a uniform brightness and depth of penetration 384 in subdermal layer 37.

Notice that LED driver IC 86 and LEDs 93*a* through 93*e* comprise relatively stiff, i.e. inflexible plastic packages incapable of significant bending. Because the surface area of the LEDs is small, minimal deformation is manifest so that no cracking or breakage results except for bending with an extremely tight radius of curvature. LED driver IC however is sufficiently large that package cracking is a concern, mitigated in part by bending of the leads under stress, whereby the leads act like a shock absorber to relieve stress from the plastic cavity. For this reason and others, LED driver IC should be packaged in leaded packages like the LQFP-packages where metallic leads extend from the package's exterior surface and bend down to the printed circuit board. Because metallic leads, typically of copper, are able to bend, they relieve stress during deformation of the LED pad. To further reduce the magnitude of stress from bending and to reduce the risk of cracking, LED driver IC is mounted on the edge of flexible PCB 381 near the pad's connectors, or alternatively on a separate stiffer PCB, again located near a pad connector where bending is limited.

In contrast, leadless packages like the QFN where a small conductive area on the underside of the package is soldered directly onto the PCB have no means to bend and are therefore unable to absorb the stress of deformation without cracking the package or fracturing its solder joint to the PCB. For this reason and because leaded packages can be assembled using low-cost wave soldering in older and cheaper PCB factories, leaded packages are preferred in the disclosed phototherapy apparatus.

Figure 28:
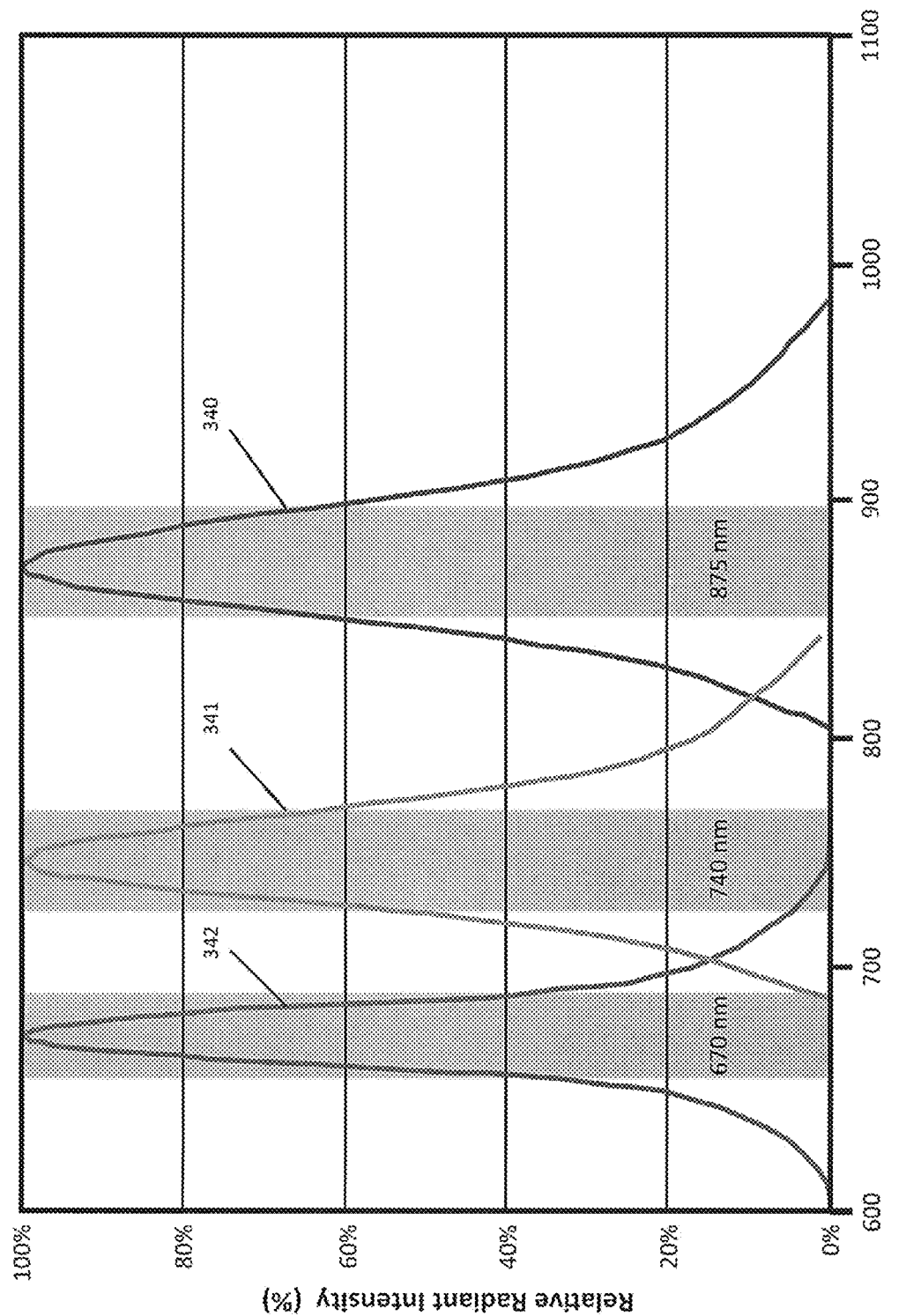
FIG. 28 is a graph of radiant intensity (normalized power output) versus wavelength LEDs of various wavelengths.

Depending on its application, an LED pad may include any number of LEDs and laser diodes configured in a variety of ways. While LED pad 204 is shown to comprise an array of three different wavelength LEDs, any number of wavelengths may be used in its construction. Instead of using an array of three types of LED wavelengths as shown, the entire pad for example may comprise an array of only a single wavelength LED, an array of two wavelengths of LEDs, or an array of four or more type of LEDs. As shown in the graph of relative radiant intensity (%), a normalized measure of an LED's optical power output, versus LED wavelength in FIG. 28, LEDs may constitute a variety of wavelengths.

The power output curve for LED 342 has a mean value of 670 nm, and a spectral variation around its mean value of approximately ±10 nm. In the electromagnetic spectrum, LED output 342 represents the lower frequency end of visible light, dominated by a deep red color. Power output curve 341 describes an LED in the near infrared spectrum, invisible to the human eye, having a nominal wavelength of 740 nm and a spectral variation around its mean value of approximately ±15 nm. Power output curve 340 describes an LED deeper in the infrared spectrum, also invisible to the human eye, having a nominal wavelength of 875 nm and a spectral variation around its mean value of approximately ±20 nm. Other LEDs with wavelengths throughout the visible spectrum and into the ultraviolet spectrum are also available as required.

The LEDs may be assembled separately into distinct packages, each with their own optical lens atop the package to better distribute the LED's light output, or may be combined into a single package as a "tri-LED" device, preferably with separate anode and cathode contacts for each of the three LEDs. It is also possible for LED pads comprising multiple LED arrays, laser diodes may in part be used in place of LEDs. As described previously, the narrow spectral bandwidth produced laser diodes reduces the observed magnitude of photobiomodulation with lasers compared to LEDs. For that reason, and because of their higher cost, their use is likely to remain restricted to specialty applications.

The total number of LEDs conducting at one time determines the average brightness, i.e. the optical power output, of the LED pad. While multiple wavelengths of LED may be illuminated simultaneously, for reasons described previously in the application, it is generally beneficial to drive only strings of LEDs having the same wavelengths at one time. Assuming that in most cases an array of only one LED wavelength will be illuminated at one time and all with the same magnitude of current $I_{LED}$, then the total optical power output of an LED pad is given by $$P_{EMR} = k[m \cdot n \cdot I_{LED}/(\# \text{ of types of LED wavelengths})]$$

For example LED pad 204 shown in FIG. 26 (including both large pad portion 330a and small pad portion 330b) comprises 24 strings of LEDs with each string constructed from the series connection of 12 LEDs. The total number of LEDs is therefore 288 or 96 LEDs in each array of any given wavelength. If the LEDs are biased at 20 mA at 100% duty factor, the LED array has an output power proportional to 96·20 mA=1.92 LED-amps. Given the LED-amps and proportionality constant k, the actual optical power output can be calculated. To determine the actual optical power output, however, requires knowing the LED optical power output at a given current, a parameter often not rated or specified on an LED's data sheet.

If, nonetheless, a higher areal power density (in W/cm$^2$) is desired, the LEDs may be driven at a higher current, or a denser array of LEDs may be used. One other choice is to replace all the rows of single LEDs with tri-LEDs. In the example of LED pad 204 comprising LED pad portions 330a and 330b, using tri-LEDs triples the areal power density but increases the number of LED driver IC channels from 24 to 72 increasing the number of 16-channel LED drivers from 2 to 5. It also increases the number of pins on connector 331 by 16, i.e. from 10 to 26 to accommodate the added wiring.

As shown, pad 204 comprises 24 rows and 12 columns, i.e. where the number of LED driver IC channels n=24, and the number of LEDs connected in series m=12. Alternatively, to increase the optical power output of the pad, the number of rows can be increased (by adding more LED driver IC channels), or the number of columns, i.e. the number of series connected LEDs m, can be increased (but by increasing the supply voltage needed to drive the LED strings. In a preferred embodiment, for safe operation, the maximum number of series connected LED should be limited so as to avoid requiring a supply voltage $+V_{LED}$ exceeding 42V, an industry recognized standard for safe low voltages and for UL approval.

LED Selection

To maximize the previously described photobiomodulation effect in phototherapy treatments of internal organs and tissue, the wavelength of light emitted from a LED must penetrate the skin, passing through the body to be absorbed by the targeted tissue of an internal organ or tissue. Numerous research laboratories have characterized the wavelength absorption data for various molecules within the human body, each contributing the spectral analysis from their specific works.

Figure 29A:
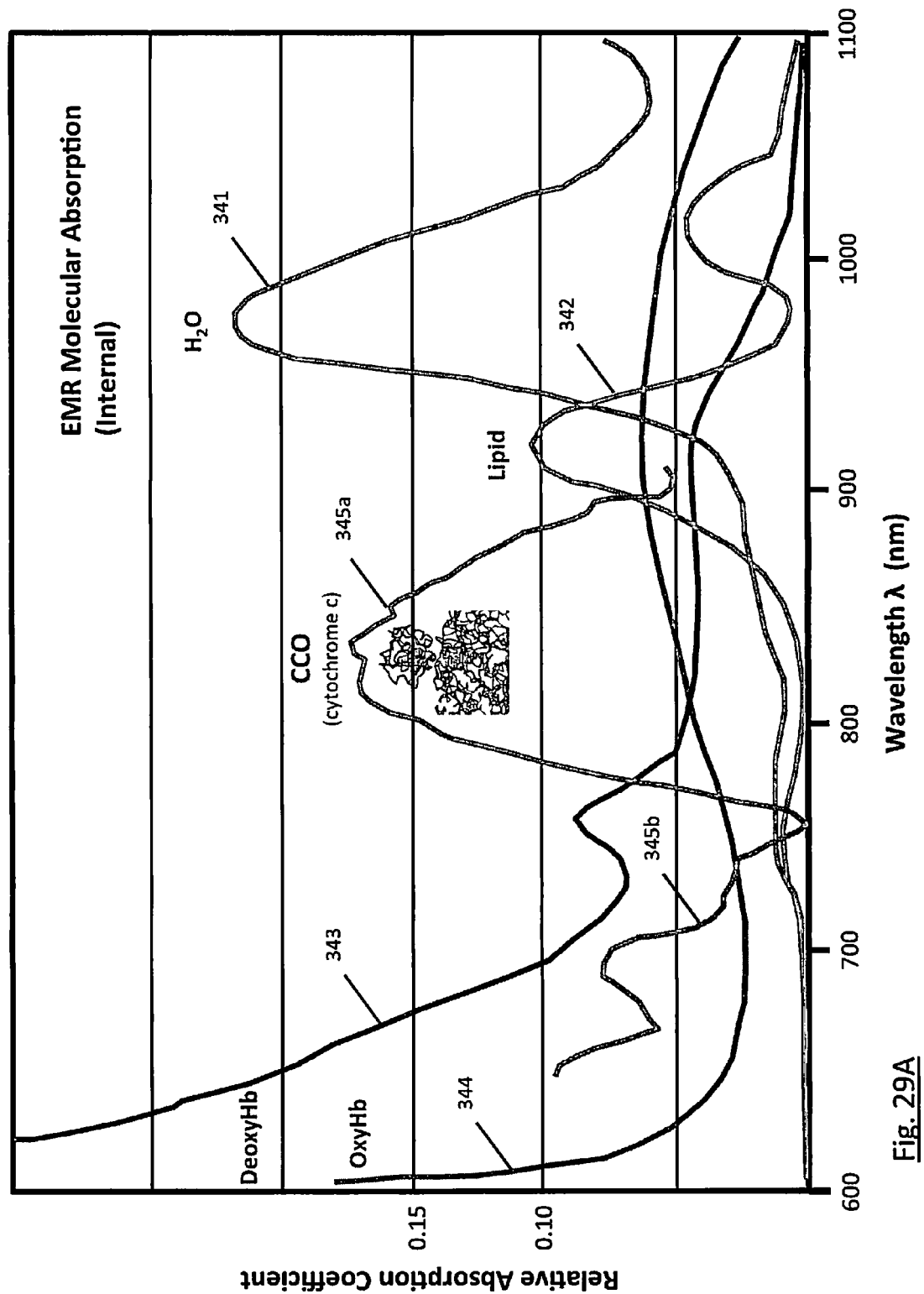
FIG. 29A is a graph of the relative absorption coefficient of various biochemicals as a function of the wavelength of incident EMR.

Collectively, the absorption spectra of various important bio-molecules are summarized in FIG. 29A. The graph, covering the range in the visible red and near infrared spectrum from 600 nm to 1100 nm, represents one of the few regions where non-ionizing EMR exhibits its greatest penetration depth in animals, mammals, and in humans. The graph illustrates in relative magnitude of absorption, the absorption spectra for water ($H_2O$) in curve 341, for lipids and fats in curve 342, for oxygenated hemoglobin (OxyHb) in curve 344, for deoxygenated hemoglobin (DeoxyHb) in curve 343. The absorption spectra of cytochrome-c oxidase (CCO), the biochemical described previously as the cellular battery charger in mitochondria, is shown by curve 345a and exhibiting a secondary absorption tail 345b.

Using a relative absorption as a basis of comparison, water 341 dominates the absorption spectra for wavelengths of 950 nm and longer, lipids and fats 342 dominate the absorption in a band of slightly shorter wavelengths ranging from 900 to 950 nm. Below 750 nm, deoxygenated hemoglobin 343 in blood in the veinous system is the dominant bio-molecular absorber, absorbing EMR with an absorption coefficient more than four times that of oxygen rich blood in the arterial system.

Figure 29B:
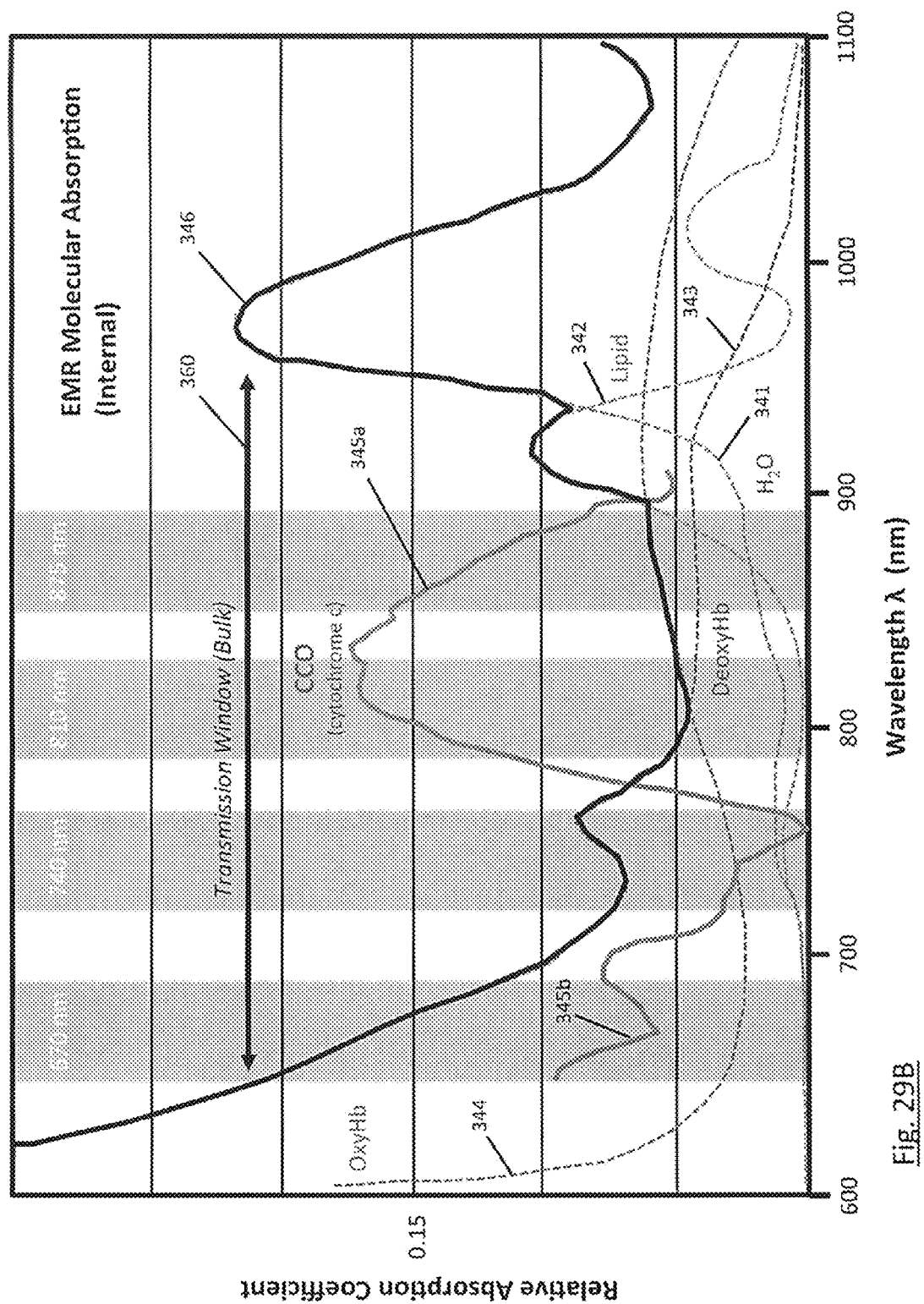
FIG. 29B is a graph of the relative absorption coefficient of internal tissues as a function of the wavelength of incident EMR.

Referring to FIG. 29B, the solid bold line 346 highlights the dominant bio-molecular absorbers in the human body, namely DeoxyHb 343 at short wavelengths in the red portion of the visible light spectrum and especially below 675 nm, and for lipids and water for longer infrared wavelengths from 900 nm to 1050 nm. At these wavelengths, the body is essentially opaque, preventing EMR from penetrating subdermal tissue to reach internal organs.

Bold line 346 clearly identifies that in between the absorption of water in the infrared spectrum and of blood in the red visible spectrum, in a band from 675 nm to 900 nm, a transmission window 360 exists where light can penetrate the skin and reach internal organs. In the middle of this transmission window, located in the range from 780 nm to 900 nm is the absorption spectrum for cytochrome-c oxidase (CCO) 345a, the dominant absorber of light in mitochondria. So existing precisely in the middle of the frequency window where light can penetrate into and reach an animal's internal organs, is the one band of frequencies where mitochondria absorb light and where photoexcitation of cytochrome-c oxidase produces energy.

Evolutionary biologists explain this fortuitous and remarkably coincidental alignment of light's transmission window in animals and the absorption spectra of CCO in mitochondria by symbiotic evolution, where mitochondria (like their present day cousin blue-green algae), were once free floating organisms living in shallow water and deriving their energy from sunlight filtered by water. The fact that water absorbs or reflects ultraviolet and most visible light but passes infrared wavelengths provides indirect evidence of why mitochondria evolved especially to absorb light at infrared wavelengths. Later, after mitochondria were incorporated into the first eukaryotic cells and ultimately in animal and mammalian cells, evolutionary biologists postulate that blood and specifically hemoglobin evolved symbiotically so as to not block mitochondria's ability to absorb infrared light. While theology offers an alternative explanation, regardless of the reason, the fact remains that CCO in mitochondria absorbs light and infrared radiation at precisely the wavelengths not blocked by water, fat and blood. Transmission window 360 therefore represents a spectral band where photobiomodulation of cells and tissue of internal organs has its greatest absorption peak.

Photoexcitation using LEDs having wavelengths in this transmission window exhibit good penetration depths unblocked by other biomolecules, and efficient absorption by CCO. Four bands of LED wavelengths are well matched to facilitating photoexcitation of mitochondrial CCO, namely 875 nm, 819 nm, 740 nm, and 670 nm. Actually the secondary absorption tail 345b of CCO is partially blocked by DeoxyHb 343, reducing the penetration of light at these wavelengths to one half or one third that of the impinging light, and in general diminishing the photoexcitation response and photobiomodulation of internal organs at shorter wavelengths.

While the photoexcitation of CCO and the resulting creation of ATP are well documented, it is not well understood at this time whether other intracellular absorption mechanisms directly stimulate photobiomodulation. It has been suggested, for example, that the catalyst hydrogen peroxide ($H_2O_2$) may be formed directly through photoexcitation. Also in FIG. 29B, another small EMR transmission window is present around 1080 nm. At this moment, no bio-molecules have been identified to absorb light at this wavelength so it remains unclear whether any photobiomodulation will be manifested by illumination in this window.

Figure 30:
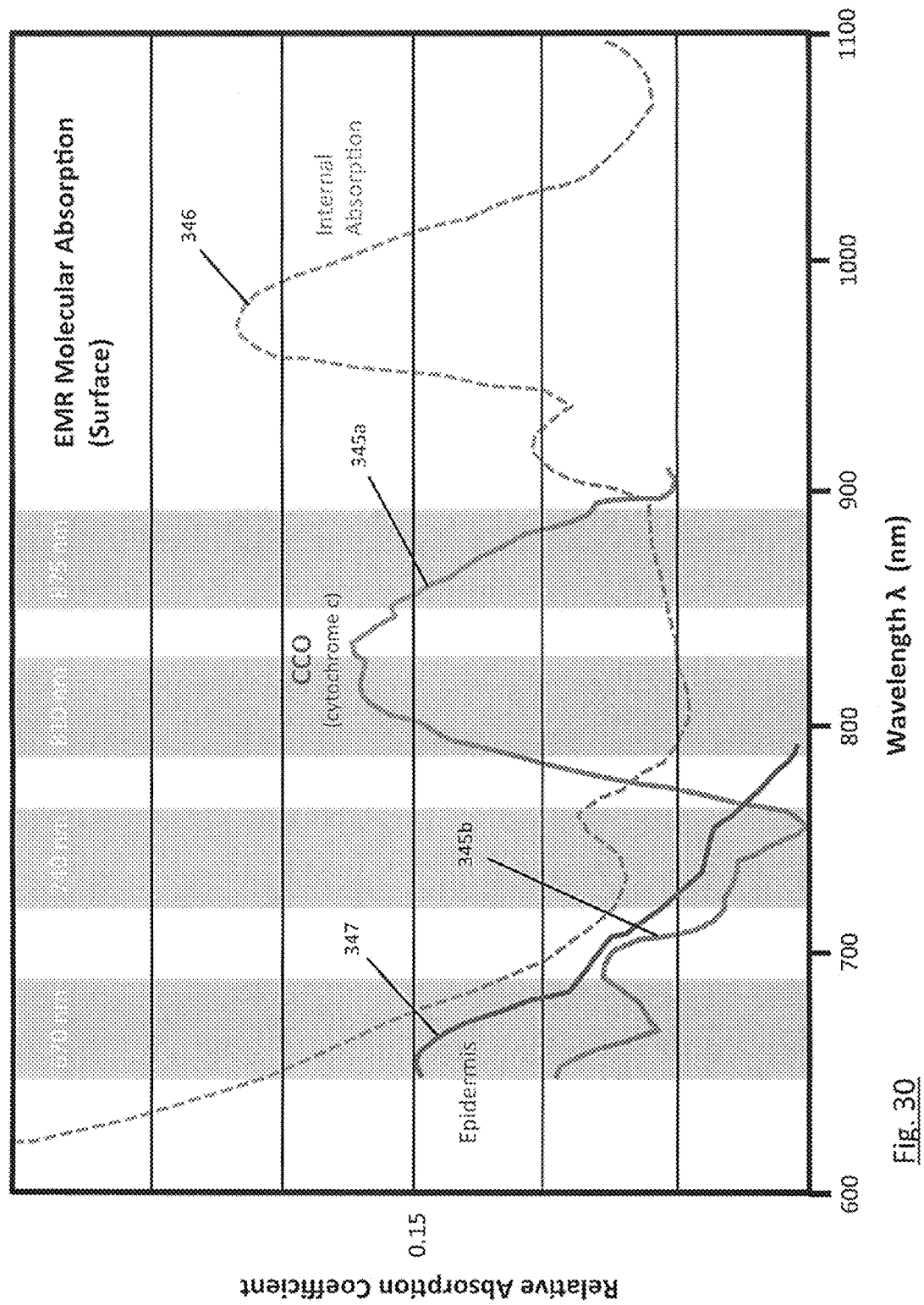
FIG. 30 is a graph of the relative absorption coefficient of surface tissues as a function of the wavelength of incident EMR.

While the opportunity for photobiomodulation and phototherapy on internal organs and subdermal tissue is restricted by the absorption spectra of intervening blood, fat, water and other bio-molecules, the photoexcitation of skin and surface layers is not. For photoexcitation on the skin's surface, the absorption spectrum 346 (shown as a dashed line) in FIG. 30 is not relevant because blood, fat and water are located beneath the affected tissue, and therefore cannot block impinging EM R. Unimpeded, EMR in the entire spectrum from 600 nm to 1100 nm (including specifically 670 nm and 740 nm LEDs) is available for the purpose of photoexcitation. Absorption of EMR on a surface, more accurately "adsorption", over this range includes light is adsorbed by CCO 345a, by CCO's secondary tail 345b, by epidermis 347, and by melanosomes (not shown). At present it remains unclear whether shorter wavelength light beyond red in the visible spectrum exhibits photobiomodulation or offers any phototherapeutic potential.

While ultraviolet light or UVL, primarily used for skin tanning, creates skin damage and can induce neoplasms (skin cancer), in low doses it offers the potential for ridding the skin's surface of viral, yeast and bacterial invaders, in essence creating a hostile environ for infections. In cases of gunshot, puncture wounds, skin lacerations, burns, and third degree bone breaks (where the skin is penetrated by bone) the use of ultraviolet LEDs in a sequential phototherapy regimen combined with red and infrared photoexcitation may assist in staving off infection while stimulating an immune response and tissue repair, at least temporarily until proper treatment in an aseptic environment can be administered.

In conclusion, analysis of EMR absorption spectra suggests that longer wavelength LEDs in the 810 nm and 875 nm exhibit the potential for greater photobiomodulation in internal organs while the entire spectrum, especially 670 nm and 740 nm LEDs are beneficial for photobiomodulation in skin and epithelial tissue. The disclosed phototherapy apparatus offers a controlled means by which to drive and control LEDs and laser diodes to maximize photobiomodulation in accordance with this disclosure.

I claim:

1. A phototherapy system comprising:
   a first light-emitting diode (LED) string, said first LED string comprising a plurality of LEDs adapted to generate electromagnetic radiation (EMR) including radiation of a first wavelength $\lambda_1$;
   a first channel driver coupled to said first LED string for controlling an electric current through said first LED string;
   a microcontroller comprising a pattern library, said pattern library storing at least one algorithm, said at least one algorithm defining a process sequence for controlling said first LED string, said algorithm specifying a frequency $f_1$ of pulses of EMR emitted by said plurality of LEDs, a duty factor of said pulses of EMR emitted by said plurality of LEDs and a magnitude of said current through said first LED string; and a pad comprising said first LED string, said first LED string being positioned in said pad so as to allow said EMR to be radiated into a living organism when said pad is positioned adjacent said living organism.

2. The phototherapy system of claim 1 wherein said algorithm further specifies a phase delay φ of said pulses of EMR emitted by said plurality of LEDs.

3. The phototherapy system of claim 1 wherein said pad comprises a second LED string, said second LED string comprising a second plurality of LEDs adapted to generate EMR including radiation of a second wavelength $\lambda_2$, said process sequence being for controlling each of said first and second LED strings.

4. The phototherapy system of claim 1 wherein said first channel driver comprises:
a $t_{on}$ register for storing data representing a length of time that said first LED string is turned on;
a counter; and
a MOSFET, said MOSFET being connected in series with said first LED string, said counter being coupled to said $t_{on}$ register, said counter being coupled to a gate terminal of said MOSFET so as to turn said MOSFET on for said length of time in response to said data stored in said $t_{on}$ register.

5. The phototherapy system of claim 1 wherein said pad is flexible such that said pad can fit snugly against a curved surface of said living organism.

6. The phototherapy system of claim 1 wherein said living organism is a human being.

7. The phototherapy system of claim 1 wherein said EMR comprises a spectral band of wavelengths comprising said first wavelength $\lambda_1$.

8. The phototherapy system of claim 1 wherein said first channel driver comprises:
a $t_{on}$ register for storing data representing a length of time that said first LED string is turned on;
a counter;
a MOSFET, said MOSFET being connected in series with said first LED string, said counter being coupled to said $t_{on}$ register, said counter being coupled to a gate terminal of said MOSFET so as to turn said MOSFET on for said length of time in response to said data stored in said $t_{on}$ register;
an $I_{LED}$ register for storing data representing a magnitude of said electric current; and
a digital-to-analog (D/A) converter, said D/A converter being coupled to said $I_{LED}$ register, said D/A converter being coupled to a gate terminal of said MOSFET so as determine said magnitude of said electric current through said first LED string in response to said data stored in said $I_{LED}$ register.

9. The phototherapy system of claim 1 wherein said microcontroller comprises a clock and timing interface coupled to a counter for generating a clock pulse to advance said counter.

10. The phototherapy system of claim 1 wherein said magnitude of said current through said first LED string specified in said algorithm is a constant magnitude.

11. A phototherapy system comprising:
a first light-emitting diode (LED) string, said first LED string comprising a plurality of LEDs adapted to generate electromagnetic radiation (EMR) including radiation of a first wavelength $\lambda_1$;

a first channel driver coupled to said first LED string for controlling an electric current through said first LED string, said first channel driver comprising:
a $t_{on}$ register for storing data representing a length of time that said first LED string is turned on;
a counter; and
a MOSFET, said MOSFET being connected in series with said first LED string, said counter being coupled to said $t_{on}$ register, said counter being coupled to a gate terminal of said MOSFET so as to turn said MOSFET on for said length of time in response to said data stored in said $t_{on}$ register;
a microcontroller comprising a pattern library, said pattern library storing at least one algorithm, said at least one algorithm defining a process sequence for controlling said first LED string; and
a pad comprising said first LED string, said first LED string being positioned in said pad so as to allow said EMR to be radiated into a living organism when said pad is positioned adjacent said living organism.

12. The phototherapy system of claim 11 wherein said microcontroller comprises a clock and timing interface coupled to said counter for generating a clock pulse to advance said counter.

13. The phototherapy system of claim 11 wherein said pad is flexible such that said pad can fit snugly against a curved surface of said living organism.

14. The phototherapy system of claim 11 wherein said EMR comprises a spectral band of wavelengths comprising said first wavelength $\lambda_1$.

15. A phototherapy system comprising:
a first light-emitting diode (LED) string, said first LED string comprising a plurality of LEDs adapted to generate electromagnetic radiation (EMR) including radiation of a first wavelength $\lambda_1$;
a first channel driver coupled to said first LED string for controlling an electric current through said first LED string, said first channel driver comprising:
an $I_{LED}$ register for storing data representing a magnitude of said electric current;
a digital-to-analog (D/A) converter; and
a MOSFET, said MOSFET being connected in series with said first LED string, said D/A converter being coupled to said $I_{LED}$ register, said D/A converter being coupled to a gate terminal of said MOSFET so as determine said magnitude of said electric current in response to said data stored in said $I_{LED}$ register;
a microcontroller comprising a pattern library, said pattern library storing at least one algorithm, said at least one algorithm defining a process sequence for controlling said first LED string; and
a pad comprising said first LED string, said first LED string being positioned in said pad so as to allow said EMR to be radiated into a living organism when said pad is positioned adjacent said living organism.

16. The phototherapy system of claim 15 wherein said first channel driver further comprises:
a $t_{on}$ register for storing data representing a length of time that said first LED string is turned on; and
a counter, said counter being coupled to said $t_{on}$ register, said counter being coupled to a gate terminal of said MOSFET so as to turn said MOSFET on for said length of time in response to said data stored in said $t_{on}$ register.

17. The phototherapy system of claim 15 wherein said first channel driver further comprises:

a $t_{on}$ register for storing data representing a length of time that said first LED string is turned on;

a counter; and a MOSFET, said MOSFET being connected in series with said first LED string, said counter being coupled to said $t_{on}$ register, said counter being coupled to a gate terminal of said MOSFET so as to turn said MOSFET on for said length of time in response to said data stored in said $t_{on}$ register.

18. The phototherapy system of claim 15 wherein said pad is flexible such that said pad can fit snugly against a curved surface of said living organism.

19. The phototherapy system of claim 15 wherein said EMR comprises a spectral band of wavelengths comprising said first wavelength $\lambda_1$.

20. The phototherapy system of claim 15 wherein said microcontroller comprises a clock and timing interface coupled to said counter for generating a clock pulse to advance said counter.

21. A phototherapy system comprising:

a first light-emitting diode (LED) string, said first LED string comprising a plurality of LEDs adapted to generate electromagnetic radiation (EMR) including radiation of a first wavelength $\lambda_1$;

a first channel driver coupled to said first LED string for controlling an electric current through said first LED string;

a microcontroller comprising a pattern library, said pattern library storing at least one algorithm, said at least one algorithm defining a process sequence for controlling said first LED string, said algorithm specifying a frequency $f_1$ of pulses of EMR emitted by said plurality of LEDs, a phase delay $\varphi$ of said pulses of EMR emitted by said plurality of LEDs and a magnitude of said current through said first LED string; and a pad comprising said first LED string, said first LED string being positioned in said pad so as to allow said EMR to be radiated into a living organism when said pad is positioned adjacent said living organism.

22. The phototherapy system of claim 21 wherein said pad comprises a second LED string, said second LED string comprising a second plurality of LEDs adapted to generate EMR including radiation of a second wavelength $\lambda_2$, said process sequence being for controlling each of said first and second LED strings.

23. The phototherapy system of claim 21 wherein said first channel driver comprises:

a $t_{on}$ register for storing data representing a length of time that said first LED string is turned on;

a counter; and a MOSFET, said MOSFET being connected in series with said first LED string, said counter being coupled to said $t_{on}$ register, said counter being coupled to a gate terminal of said MOSFET so as to turn said MOSFET on for said length of time in response to said data stored in said $t_{on}$ register.

24. The phototherapy system of claim 21 wherein said pad is flexible such that said pad can fit snugly against a curved surface of said living organism.

25. The phototherapy system of claim 21 wherein said living organism is a human being.

26. The phototherapy system of claim 21 wherein said EMR comprises a spectral band of wavelengths comprising said first wavelength $\lambda_1$.

27. The phototherapy system of claim 21 wherein said first channel driver comprises:

a $t_{on}$ register for storing data representing a length of time that said first LED string is turned on;

a counter;

a MOSFET, said MOSFET being connected in series with said first LED string, said counter being coupled to said $t_{on}$ register, said counter being coupled to a gate terminal of said MOSFET so as to turn said MOSFET on for said length of time in response to said data stored in said $t_{on}$ register;

an $I_{LED}$ register for storing data representing a magnitude of said electric current; and a digital-to-analog (D/A) converter, said D/A converter being coupled to said $I_{LED}$ register, said D/A converter being coupled to a gate terminal of said MOSFET so as determine said magnitude of said electric current through said first LED string in response to said data stored in said $I_{LED}$ register.

28. The phototherapy system of claim 21 wherein said microcontroller comprises a clock and timing interface coupled to a counter for generating a clock pulse to advance said counter.

29. The phototherapy system of claim 21 wherein said magnitude of said current through said first LED string specified in said algorithm is a constant magnitude.

30. A phototherapy system comprising:

a first light-emitting diode (LED) string, said first LED string comprising a plurality of LEDs adapted to generate electromagnetic radiation (EMR) including radiation of a first wavelength $\lambda_1$;

a first channel driver coupled to said first LED string for controlling an electric current through said first LED string, said first channel driver comprising:

a $t_{on}$ register for storing data representing a length of time that said first LED string is turned on;

a counter; and a MOSFET, said MOSFET being connected in series with said first LED string, said counter being coupled to said $t_{on}$ register, said counter being coupled to a gate terminal of said MOSFET so as to turn said MOSFET on for said length of time in response to said data stored in said $t_{on}$ register;

a microcontroller comprising a pattern library, said pattern library storing at least one algorithm, said at least one algorithm defining a process sequence for controlling said first LED string, said algorithm specifying a frequency $f_1$ of pulses of EMR emitted by said plurality of LEDs and a magnitude of said current through said first LED string; and a pad comprising said first LED string, said first LED string being positioned in said pad so as to allow said EMR to be radiated into a living organism when said pad is positioned adjacent said living organism.

31. The phototherapy system of claim 30 wherein said pad comprises a second LED string, said second LED string comprising a second plurality of LEDs adapted to generate EMR including radiation of a second wavelength $\lambda_2$, said process sequence being for controlling each of said first and second LED strings.

32. The phototherapy system of claim 30 wherein said pad is flexible such that said pad can fit snugly against a curved surface of said living organism.

33. The phototherapy system of claim 30 wherein said living organism is a human being.

34. The phototherapy system of claim 30 wherein said EMR comprises a spectral band of wavelengths comprising said first wavelength $\lambda_1$.

35. The phototherapy system of claim 30 wherein said first channel driver further comprises:
- an $I_{LED}$ register for storing data representing a magnitude of said electric current; and
- a digital-to-analog (D/A) converter, said D/A converter being coupled to said $I_{LED}$ register, said D/A converter being coupled to a gate terminal of said MOSFET so as determine said magnitude of said electric current through said first LED string in response to said data stored in said $I_{LED}$ register.

36. The phototherapy system of claim 30 wherein said microcontroller comprises a clock and timing interface coupled to a counter for generating a clock pulse to advance said counter.

37. The phototherapy system of claim 30 wherein said magnitude of said current through said first LED string specified in said algorithm is a constant magnitude.

38. A phototherapy system comprising:
- a first light-emitting diode (LED) string, said first LED string comprising a plurality of LEDs adapted to generate electromagnetic radiation (EMR) including radiation of a first wavelength $\lambda_1$;
- a first channel driver coupled to said first LED string for controlling an electric current through said first LED string, said first channel driver comprising:
  - a $t_{on}$ register for storing data representing a length of time that said first LED string is turned on;
  - a counter;
  - a MOSFET, said MOSFET being connected in series with said first LED string, said counter being coupled to said $t_{on}$ register, said counter being coupled to a gate terminal of said MOSFET so as to turn said MOSFET on for said length of time in response to said data stored in said $t_{on}$ register;
  - an $I_{LED}$ register for storing data representing a magnitude of said electric current; and
  - a digital-to-analog (D/A) converter, said D/A converter being coupled to said $I_{LED}$ register, said D/A converter being coupled to a gate terminal of said MOSFET so as determine said magnitude of said electric current through said first LED string in response to said data stored in said $I_{LED}$ register;
- a microcontroller comprising a pattern library, said pattern library storing at least one algorithm, said at least one algorithm defining a process sequence for controlling said first LED string, said algorithm specifying a frequency $f_1$ of pulses of EMR emitted by said plurality of LEDs and a magnitude of said current through said first LED string; and
- a pad comprising said first LED string, said first LED string being positioned in said pad so as to allow said EMR to be radiated into a living organism when said pad is positioned adjacent said living organism.

39. The phototherapy system of claim 38 wherein said pad comprises a second LED string, said second LED string comprising a second plurality of LEDs adapted to generate EMR including radiation of a second wavelength $\lambda_2$, said process sequence being for controlling each of said first and second LED strings.

40. The phototherapy system of claim 38 wherein said pad is flexible such that said pad can fit snugly against a curved surface of said living organism.

41. The phototherapy system of claim 38 wherein said living organism is a human being.

42. The phototherapy system of claim 38 wherein said EMR comprises a spectral band of wavelengths comprising said first wavelength $\lambda_1$.

43. The phototherapy system of claim 38 wherein said microcontroller comprises a clock and timing interface coupled to a counter for generating a clock pulse to advance said counter.

44. The phototherapy system of claim 38 wherein said magnitude of said current through said first LED string specified in said algorithm is a constant magnitude.

45. A phototherapy system comprising:
- a first light-emitting diode (LED) string, said first LED string comprising a plurality of LEDs adapted to generate electromagnetic radiation (EMR) including radiation of a first wavelength $\lambda_1$;
- a first channel driver coupled to said first LED string for controlling an electric current through said first LED string;
- a microcontroller comprising:
  - a pattern library, said pattern library storing at least one algorithm, said at least one algorithm defining a process sequence for controlling said first LED string, said algorithm specifying a frequency $f_1$ of pulses of EMR emitted by said plurality of LEDs and a magnitude of said current through said first LED string; and
  - a clock and timing interface coupled to a counter for generating a clock pulse to advance said counter; and
- a pad comprising said first LED string, said first LED string being positioned in said pad so as to allow said EMR to be radiated into a living organism when said pad is positioned adjacent said living organism.

46. The phototherapy system of claim 45 wherein said pad comprises a second LED string, said second LED string comprising a second plurality of LEDs adapted to generate EMR including radiation of a second wavelength $\lambda_2$, said process sequence being for controlling each of said first and second LED strings.

47. The phototherapy system of claim 45 wherein said pad is flexible such that said pad can fit snugly against a curved surface of said living organism.

48. The phototherapy system of claim 45 wherein said living organism is a human being.

49. The phototherapy system of claim 45 wherein said EMR comprises a spectral band of wavelengths comprising said first wavelength $\lambda_1$.

50. The phototherapy system of claim 45 wherein said magnitude of said current through said first LED string specified in said algorithm is a constant magnitude.

* * * * *